(12) United States Patent
Berryman et al.

(10) Patent No.: US 6,509,335 B1
(45) Date of Patent: Jan. 21, 2003

(54) BENZOXAZINOES/BENZOTHIAZINONES AS SERINE PROTEASE INHIBITORS

(75) Inventors: Kent Alan Berryman, Gunnison, CO (US); Dennis Michael Downing, Ann Arbor, MI (US); Danette Andrea Dudley, Ann Arbor, MI (US); Jeremy John Edmunds, Ypsilanti, MI (US); Lakshmi Sourirajan Narasimhan, Canton, MI (US); Stephen Taras Rapundalo, Ann Arbor, MI (US)

(73) Assignee: Warner-Lambert Company, Ann Arbor, MI (US)

( * ) Notice: Subject to any disclaimer, the term of this patent is extended or adjusted under 35 U.S.C. 154(b) by 0 days.

(21) Appl. No.: 09/622,265

(22) PCT Filed: Dec. 15, 1998

(86) PCT No.: PCT/US98/26708

§ 371 (c)(1),
(2), (4) Date: Aug. 14, 2000

(87) PCT Pub. No.: WO99/50257

PCT Pub. Date: Oct. 7, 1999

Related U.S. Application Data
(60) Provisional application No. 60/080,142, filed on Mar. 31, 1998.

(51) Int. Cl.$^7$ .................. A61K 31/535; A61K 31/54; C07D 265/36; C07D 279/16

(52) U.S. Cl. ................. 514/230.5; 514/224.2; 514/225.2; 514/225.5; 514/225.8; 514/226.2; 514/52; 514/105

(58) Field of Search ............ 514/224.2, 230.5; 544/52, 105

(56) References Cited

U.S. PATENT DOCUMENTS

| | | | |
|---|---|---|---|
| 3,401,166 A | 9/1968 | Krapcao et al. | 260/243 |
| 4,786,635 A | * 11/1988 | Iwa et al. | 514/224 |

FOREIGN PATENT DOCUMENTS

| | | |
|---|---|---|
| DE | 2 044 530 | 9/1970 |
| EP | 0 116 368 A1 | 8/1984 |
| EP | 0 237 573 A1 | 7/1986 |
| FR | 2 079 223 | 11/1970 |
| FR | 2 111 728 | 10/1971 |
| FR | 2 332 756 | 6/1977 |
| FR | 2332756 | * 6/1977 |
| JP | 60-166674 | 8/1985 |
| JP | 1-272524 | 10/1989 |
| JP | 3-118380 | 5/1991 |
| JP | 9227561 | * 9/1997 |
| JP | 9-227561 | 9/1997 |
| WO | WO 96/07648 | 3/1996 |
| WO | WO 98/21186 | 5/1998 |
| WO | WO 98/50372 | 11/1998 |

OTHER PUBLICATIONS

Genzginci et al., "Synthesis..2–Arylindene–2H–1, 4–Benzoxazin–3(H)–ones", IL Farnaco, 52/4, 255–6(1997).*

Kunitada, et al., Factor Xa Inhibitors, Current Pharma. Design, 2:531–542 (1996).

JP 031,183,080(A) MicroPatent PatSearch English Abstract, Compound Having Condensed Hetero Ring, Published May 20, 1991.

JP 031,183,080(A) Derwent Information Ltd. English Abstract (2002), New Fused Heterocyclic Compounds–As Centrally Acting Muscle Relaxants For Treating Cerebral Palsy, etc., Published May 20, 1991.

JP 09,227,561(A) MicroPatent PatSearch English Abstract, Xanthine Derivative, Published Sep. 2, 1997.

JP 09,227,561(A) Derwent Information Ltd. English Abstract (2002), New Xanthine Derivatives Are Inhibitors of Transcription Factor NF kappa–B—Useful For Treating e.g. Inflammatory, Auto–immune and Viral Diseases, Published Sep. 2, 1997.

JP 01,272,524(A) MicroPatent PatSearch English Abstract, Chemotherapeutic For Cancer, Published Oct. 31, 1989.

JP 01,272,524(A) Derwent Information Ltd. English Abstract (2002), Cancer Chemo–Therapeutic Compositions, Published Oct. 31, 1989.

JP 60,166,674(A) MicroPatent Pat Search English Abstract, Benzothiazine Derivative, Published Aug. 29, 1985.

JP 60,166,674(A) Derwent Information Ltd. English Abstract (2002), New Benzothiazine Derivatives and Salts, Published Aug. 29, 1985.

FR 2,223,756 Derwent Information Ltd. English Abstract (2002), Antiinflamatory (2)–arylmethyl–(4)–aminoalkyl–(1, 4)–benzoxazinones–prepd. e.g. by reducing (2)–arylmethylene compounds, Published Jun. 24, 1977.

DE 2,044,530 and FR 2,079,223 Derwent Information Ltd. English Abstract (2002), Basically Subst. 1,4–benzoxazin–3–one derivatives, Published Sep. 9, 1970 and Nov. 9, 1970, respectively.

FR 2,111,728 Derwent Information Ltd. English Abstract (2002), Benzo(xa or thia)zinones and indolinones–useful as cns depressants and antibacterials, Published Oct. 20, 1971.

(List continued on next page.)

*Primary Examiner*—Richard L. Raymond
(74) *Attorney, Agent, or Firm*—Cynthia M. Bott; Heidi M. Berven; Charles W. Ashbrook

(57) ABSTRACT

This invention discloses benzoxazinone and benzothiazinone compounds which display inhibitory effects on serine proteases such as factor Xa, thrombin, and/or factor VIIa. The invention also discloses pharmaceutically acceptable salts of the compounds, pharmaceutically acceptable compositions comprising the compounds or their salts, and methods of using them as therapeutic agents for treating or preventing disease states in mammals characterized by abnornal thrombosis.

28 Claims, No Drawings

OTHER PUBLICATIONS

Lapatto, R., et al., "X–Ray Structure of Antistasin at 1.9 A Resolution and its Modelled Complex with Blood Coagulation Factor Xa", *EMBO J.*, 1997, vol. 16, No. 17, pp. 5151–5161.

Mellott M., et al., "Enhancement of Recombinant Tissue Plasminogen Activator–induced Reperfusion by Recombinant Tick Anticoagulant Peptide, A Selective Factor Xa Inhibitor, in a Canine Model of Femoral Arterial Thrombosis", *Fibrinolysis*, 1993, vol. 7, pp. 195–202.

Lynch, J. Jr., et al., "Primary Prevention of Coronary Arterial Thrombosis with the Factor Xa Inhibitor rTAP in a Canine Electrolytic Injury Model", *Thromb. Heaemostasis*, 1995, vol. 74, No. 2, pp. 640–645.

Schaffer, L. et al., "Antithrombotic Efficacy of Recombinant Tick Anticoagulant Peptide", *Circulation*, vol. 84, No. 4, 1991, pp. 1741–1748.

Fioravanti, C., et al., "Antithrombotic Activity of Recombinant Tick and Heparin in a Rabbit Model of Venous Thrombosis", *Thromb. Res.*, 1993, vol. 71, pp. 317–324.

Wong, P., et al., "Antithrombotic Actions of Selective Inhibitors of Blood Coagulation Factor Xa in Rat Models of Thrombosis," *Thromb. Res.*, 1996, vol. 83, No. 2, pp. 117–126.

Edmunds, J., et al., "Chapter 6: Thrombin and Factor Xa Inhibition", *Annual Reports of Medicinal Chemistry*, 1996, pp. 51–60.

Moriyama, Y., et al., "Absorption Characteristics of Azasetron from Rectal and Oral Routes in Rabbits", *Biol. Pharm. Bull*, 1997, vol. 20, No. 6, pp. 701–703.

Gezginci, H., et al., "Synthesis of New 2–Arylindene–2H–1, 4–Benzoxazin–3(4H)–Ones", *Il Farmaco*, 1997, vol. 52, No. 4, pp. 255–256.

Sastry, C. V., et al., "Synthesis of 6–(1,4,5,6–tetrahydro–6–oxo–3–pyridazinyl)–2H–1,4–benzoxazin–3(4H)–ones as as Possible Cardiotonic Agents", *Indian J. Chem*, 1989, vol. 28B, pp. 882–884.

Bornschein, I., et al., "Massenspektrometrie von 2–Phenyl–4–[Beta–dimethylaminoathyl]–6–methyl–2.3–dihydro–1.4–benzoxazin–3–on („AR17 048") und seinen Metaboliten, *Pharmazie*, 1977, vol. 32, No. 11, pp. 695–697.

Bornschein, I., et al., "Biotransformation von 2–Phenyl–4–[Beta–dimethylaminoathyl]–6–methyl–2.3–dihydro–1.4–benzoxazin–3–on („AR17 048") einem potentiellen Antirheumaticum", *Pharmazie*, 1977, vol. 32, No. 11, pp. 587–592.

Fujita, M., et al., Synthesis and Ca2 Antagonistic Activity of 2–[2–[(aminoalkyl)oxy]–5–methoxyphenyl]–3, 4–dihydro–4–methyl–3–oxo–2H–1,4–benzothiazines, *J. Med. Chem.*, 1990., vol. 33, pp. 1898–1905.

Shridhar, D. R., et al., Synthesis & Anthelmintic Activity of Some New 6– & 7–Isothiocyanato–2H–1, 4–benzoxa(thia)zin–3(4h)–ones & Benzoxa(thia)zin–3(4H)–thiones, *Indian J. Chem*, 1985, vol. 24B, pp. 1263–1267.

Thuillier G., et al., Synthese et activite pharmacologique de dihydro–2,3 benzoxazine–1, 4 ones–3 substituees en position 4, *Eur. J. Med. Chem. –Chim. Ther.*, 1975, vol. 10, No. 1, pp. 37–42.

PCT International Search Report, PCT/US98/26708, 1998.

\* cited by examiner

BENZOXAZINOES/BENZOTHIAZINONES AS SERINE PROTEASE INHIBITORS

This application is a 371 of PCT/US98/26708, filed Dec. 15, 1998 and claims benefit of U.S. Provisional Application No. 60/080,142, filed Mar. 31, 1998.

FIELD OF THE INVENTION

In one aspect, this invention discloses benzoxazinone and benzothiazinone compounds which display inhibitory effects on serine proteases such as factor Xa, thrombin, and/or factor VIIa. The invention also discloses pharmaceutically acceptable salts of the compounds, pharmaceutically acceptable compositions comprising the compounds or their salts, and methods of using them as therapeutic agents for treating or preventing disease states in mammals characterized by abnormal thrombosis.

BACKGROUND OF THE INVENTION

In economically developed countries, cardiovascular disease still represents a major cause of mortality. In particular, abnormal coagulation and inappropriate thrombus formation within blood vessels precipitates many acute cardiovascular disease states. While it has long been recognized that a variety of plasma proteins such as fibrinogen, serine proteases. and cellular receptors are involved in hemostasis, it is the abnormal regulation that has emerged as important contributing factors to cardiovascular disease. Thrombin can be considered the key or principal regulatory enzyme in the coagulation cascade; it serves a pluralistic role as both a positive and negative feedback regulator in normal hemostasis. However, in some pathologic conditions, the former is amplified through catalytic activation of cofactors required for thrombin generation such as factor Xa. Factor Xa, as part of the prothrombinase complex composed of nonenzymatic cofactor Va, calcium ions, and a phospholipid membrane surface regulates the generation of thrombin from its zymogen prothrombin. Furthermore, the location of the prothrombinase complex at the convergence of both the intrinsic and extrinsic coagulation pathways suggests that inhibition of factor Xa, and hence thrombin generation, may be a viable approach to limiting the procoagulant activity of thrombin.

Indeed, ample evidence exists for the role of factor Xa inhibitors as anticoagulants. Antistasin, a potent inhibitor of blood coagulation factor Xa from the Mexican leech: Haementeria officinalis, displays antithrombotic activity in various models of arterial and venous thrombosis (Lapatto et al., Embo. J., 1997:5151–5161). Other protein or polypeptide factor Xa inhibitors include recombinant tick anticoagulant peptide (rTAP), which is known to accelerate the recombinant tissue plasminogen activator mediated clot lysis and prevent acute reocclusion in the dog, hence indicating factor Xa inhibitors may be useful as an adjunct to thrombolytic therapy (Mellott et al., Fibrinolysis, 1993:195–202). Furthermore, in a canine coronary artery electrolytic lesion model, rTAP was demonstrated to reduce thrombus mass and time to occlusion in the absence of dramatic hemodynamic or hemostatic changes indicating the primary role for factor Xa in the process of arterial thrombosis (Lynch et al., Thromb. Haemostasis, 1995:640–645; Schaffer et al., Circulation, 1991:1741–1748). On the venous side, rTAP was also demonstrated to reduce fibrin deposition in a rabbit model of venous thrombosis while having little affect on systemic hemostatic parameters (Fioravanti et al., Thromb. Res., 1993:317–324). In addition to these relatively high molecular weight proteins that are not suitable as oral antithrombotic agents, there also exist examples of low molecular weight factor Xa inhibitors. In particular Dx9065a, a low molecular weight synthetic factor Xa inhibitor, has also shown antithrombotic potential in various experimental thrombosis rat models. In both arteriovenous shunt and venous stasis models, inhibition of thrombus formation was achieved at doses that had little effect on APTT, indicating that DX9065a is effective in preventing thrombosis and hence has therapeutic antithrombotic potential (Wong et al., Thromb. Res., 1996:117–126).

The majority of factor Xa inhibitors known to date have been previously summarized in two reviews (Edmunds et al., Annual Reports in Medicinal Chemistry, 1996:51 and Kunitada and Nagahara, Curr. Pharm. Des., 1996:531–542). However, it is readily apparent that there still exists a need for more effective agents that regulate factor Xa proteolytic activity.

Some benzoxazinones and benzothiazinones have been reported and these compounds have displayed marked pharmacological activity:

Moriyama et al., Biol. Pharm. Bull, 1997:701–703;
Gezginci et al., Farmaco, 1997:255–256;
Sastry et al., Indian J. Chem., Sect. B, 1989:882–884;
U.S. Pat. No. 6,807,18;
Bornschein et al., Pharmazie, 1977:695–697 and Pfeifer et al., Pharmazie, 1977:587–592;
Japanese Application 60166674;
European Application 116368;
Japanese Application 01272524;
U.S. Pat. No. 4,786,635;
Fujita M. et al., J. Med Chem., 1990:1898;
Japanese Application 03118380;
Japanese Application 09227561;
Shridhar et al., Indian J. Chem., Sect. B, 1985;24B(12):1263–1267;
Bornschein et al., Pharmazie, 1977;32(11):695–697 and 1977;32(10):587–592;
Thuillier et al., Eur. J Med Chem.—Chim. Ther., 1975;10 (1):37–42;
German Patent 2044530; and
U.S. Pat. No. 3,401,166.

None of the above articles set forth above, however, disclose or suggest compounds set forth herein that are inhibitors of serine proteases involved in the blood coagulation cascade.

SUMMARY OF THE INVENTION

One object of the present invention is to provide serine protease inhibitors that display inhibitory activity towards enzymes involved in the coagulation cascade and principally the target enzymes, factor Xa, thrombin, and factor VIIa.

A further object of the present invention is to provide serine protease inhibitors that display inhibitory activity towards the target enzyme factor Xa and are provided for in a pharmacologically acceptable state.

Still a further object of the present invention is to provide for the use of these factor Xa inhibitors and formulations thereof as anticoagulant and factor Xa inhibitory agents.

Yet a further object of the present invention is to provide for the use of these factor Xa inhibitors and formulations thereof for therapeutic treatment of various thrombotic maladies.

A further object of the present invention is a process for the synthesis of these low molecular weight thrombin inhibitors. The enzyme inhibitors of the present invention are encompassed by the structure of general Formula 1 set forth below.

The present invention meets these objectives and provides for novel compounds that display antithrombotic activity. More specifically, the present invention provides for novel compounds that display antithrombotic activity via the inhibition of factor Xa as reflected in Formula 1, or pharmaceutically acceptable salts or prodrug forms thereof. The present invention also provides pharmaceutically acceptable compositions comprising the novel compounds or their salts or prodrug forms, and methods of using them as therapeutic agents for treating or preventing disease states in mammals characterized by abnormal thrombosis.

Thus in a first embodiment, the present invention provides novel compounds of Formula 1:

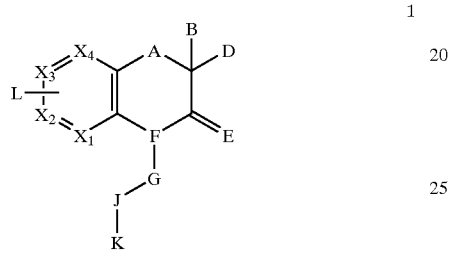

1 or stereoisomers or pharmaceutically acceptable salt forms or prodrugs thereof, wherein:

A is selected from O, S, S(=O), S(=O)(=O), OCH$_2$, CH$_2$O, SCH$_2$, S(=O)CH$_2$, S(=O)(=O)CH$_2$, CH$_2$S, CH$_2$S(=O), CH$_2$S(=O)(=O);

B is selected from hydrogen, cycloalkyl, heteroalkyl, cycloalkylalkyl, heteroalkylalkyl, aryl, arylalkyl, heterocycle, heterocycloalkyl, each optionally substituted with $R_1$ and $R_2$;

D is selected from H, (C$_{3-20}$)alkyl, cycloalkyl, heteroalkyl, cycloalkylalkyl, heteroalkylalkyl, aryl, arylalkyl, heterocycle, heterocycloalkyl, each optionally substituted with $R_1$ and $R_2$;

E is absent or selected from O, S, NH;

F is selected from N, NCH$_2$, CH$_2$N;

G is absent or selected from alkyl, alkyl interrupted by one or more heteroatoms, cycloalkyl, cycloalkyl interrupted by one or more heteroatoms;

J is absent or selected from aryl or heterocycle each optionally substituted with $R_1$ and $R_2$;

K is absent or selected from an alkyl, alkyl interrupted by one or more heteroatoms, cycloalkyl interrupted by one or more heteroatoms, cycloalkylalkyl interrupted by one or more heteroatoms, each optionally substituted with $R_1$ and $R_2$;

L is selected from H, chlorine, fluorine, bromine, iodine, OH, O(alkyl), amine, alkyl, fluoroalkyl, amide, NO$_2$, SH, S(O)$_n$(alkyl), SO$_3$H, SO$_3$alkyl, nitrile aldehyde, ketone, acid, ester, urea, Oalkylamide, Oalkylester, Oalkylacid, Nalkylacid, alkylamine, alkylamide, alkylketone, alkylacid, alkylester, alkylurea, Nalkylamide, Nalkylester, NC(=O)alkyl, NC(=O)aryl, NC(=O)cycloalkyl, NC(=O)cycloalkylalkyl, NC(=O) alkylaryl, $R_1$, $R_2$;

$R_1$ is selected from H, amine, alkylamine, amide, C(=NH)NHNH$_2$, alkylC(=NH)NHNH$_2$, C(=NH)NHOH, alkylC(=NH)NHOH, NHC(=NH)NH$_2$, alkylNHC(=NH)NH$_2$, C(=S)NH$_2$, alkylC(=S)NH$_2$, C(=NH)alkyl, alkylC(=NH)alkyl, C(=NR$_3$)N(R$_4$)(R$_5$), alkylC(=NR$_3$)N(R$_4$)(R$_5$);

$R_2$ is selected from H, chlorine, fluorine, bromine, iodine, OH, Oalkyl, amine, alkylaldehyde, alkylamide, alkylester, alkylketone, alkylacid, Oalkylamide. Oalkylacid, Oalkylester, aninealkylacid, aminealkylamide, aminealkylester, NC(=O)alkyl, NC(=O)aryl, NC(=O)cycloalkyl, NC(=O)alkylaryl, alkylamine, amide, aldehyde, ester, ketone, NO$_2$, SH, S(O)$_n$(C$_{1-10}$alkyl), SO$_3$H, SO$_3$alkyl, CHO, acid, alkyl, C(=NH)alkyl, C(=NH)NHNH$_2$, alkylC(=NH)NHNH$_2$, C(=NH)NHOH, alkylC(=NH)NHOH, NHC(=NH)NH$_2$, alkylNHC(=NH)NH$_2$, C(=S)NH$_2$, alkylC(=S)NH$_2$, alkylC(=NH)alkyl, C(=NR$_3$)N(R$_4$)(R$_5$), alkylC(=NR$_3$)N(R$_4$)(R$_5$);

$R_3$, $R_4$, and $R_5$ are a hydrogen atom, alkyl group having 1 to 4 carbon atoms optionally interrupted by a heteroatom, or $R_4$ and $R_5$ are bonded to form —(CH$_2$)$_p$—W—(CH$_2$)$_q$—, wherein p and q are an integer of 2 or 3, a certain position on the methylene chain is unsubstituted or substituted by an alkyl group having 1 to 4 carbon atoms, W is a direct bond, —CH$_2$—, —O—, —N(R$_6$)—, or —S(O)$_r$— wherein $R_6$ is H or alkyl, and r is 0 or 1 or 2;

n is selected from 0, 1, 2;

$X_1$ is C or N;

$X_2$ is C or N;

$X_3$ is C or N; and $X_4$ is C or N.

Preferred compounds according to this invention have the Formula 2:

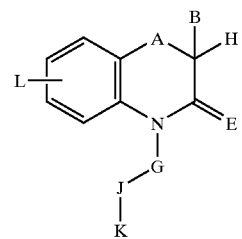

2 or stereoisomers or pharmaceutically acceptable salts, esters, amides, or prodrugs thereof, wherein A, B, E, G, J, K, and L are defined as above.

Another preferred group of compounds have the Formula 3:

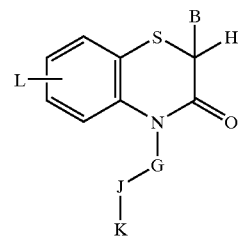

3 or stereoisomers or pharmaceutically acceptable salts, esters, amides, or prodrugs thereof, wherein B, G, J, K, and L are defined as above.

Another preferred group of compounds have the Formula 4:

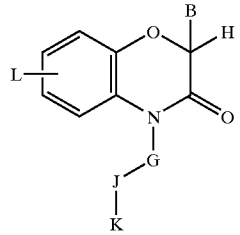

or stereoisomers or pharmaceutically acceptable salts, esters, amides, or prodrugs thereof, wherein B, G, J, K, and L are defined as above.

Even more preferred compounds have the Formula 5:

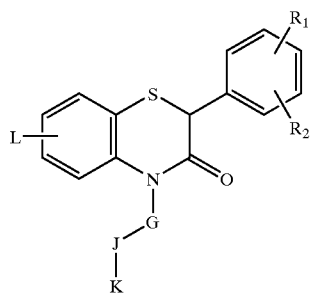

or stereoisomers or pharmaceutically acceptable salts, esters, amides, or prodrugs thereof, wherein $R_1$, $R_2$, G, J, K, and L are as defined above.

Another more preferred group of compounds have the Formula 6:

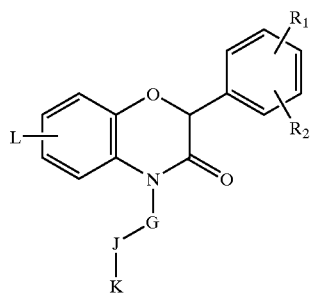

or stereoisomers or pharmaceutically acceptable salts, esters, amides, or prodrugs thereof, wherein $R_1$, $R_2$, G, J, K, and L are as defined above.

The most preferred compounds provided by this invention are compounds of Formulas 7 and 8:

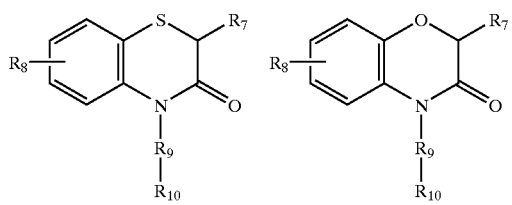

or stereoisomers or pharmaceutically acceptable salts, esters, amides, or prodrugs thereof, wherein $R_7$ is (3-amidino)phenyl, (3-hydroxy)phenyl, [3-hydroxylamino(imino)methyl]-phenyl, [3-hydrazino(imino)methyl]-phenyl, (3-aminomethyl)phenyl, (3-amino)phenyl, (3-methylamino)phenyl, (3-dimethylamino)phenyl, (5-amidino-2-hydroxy)phenyl, (1-amidino)piperid-3-yl, (5-amidino-2-methoxy)phenyl, (1-amidino)pyrrolid-3-yl, (5-amidino)thien-2-yl, (5-amidino)furan-2-yl, (5-amidino)-1,3-oxazol-2-yl, (2-amidino)-1,3-oxazol-5-yl, 1H-pyrazol-5-yl, tetrahydro- 1H-pyrazol-3-yl, (1-amidino)tetrahydro-1H-pyrazol-3-yl, (2-amidino)-1H-imidazol-4-yl, (2-amino)-1H-imidazol-4-yl, (5-amidino)-1H-imidazol-2-yl, (5-amino)-1H-imidazol-2-yl, pyridin-3-yl, (4-amino)pyridin-3-yl, (4-dimethylamino)pyridin-3-yl, (6-amino)pyridin-2-yl, (6-amidino)pyridin-2-yl, (2-amino)pyridin-4-yl, (2-amidino)pyridin-4-yl, (2-amidino)pyrimid-4-yl, (2-amino)pyrimidin4-yl, (4-amidino)pyrimid-2-yl, (4-amino)pyrimidin-2-yl, (6-amidino)pyrazin-2-yl, (6-amino)pyrazin-2-yl, (4-amidino)-1,3,5-triazin-2-yl, (4-amino)-1,3,5-triazin-2-yl, (3-amidino)-1,2,4-triazin-5-yl, (3-amino)-1,2,4-triazin-5-yl, (3-amidino)benzyl, (3-amino)benzyl, (3-aminomethyl)benzyl, (1-amidino)piperid-3-ylmethyl, (1-amidino)pyrrolid-3-ylmethyl, (5-amidino)thien-2-ylmethyl, (5-amidino)furan-2-ylmethyl, (5-amidino)oxazol-2-ylmethyl, (2-amidino)imidazol-5-ylmethyl, (5-amidino)imidazol-2-ylmethyl, (6-amidino)pyridin-2-ylmethyl, (6-amino)pyridin-2-ylmethyl, (2-amidino)pyrimidin-4-ylmethyl, (2-amino)pyrimidin-4-ylmethyl, (4-amidino)pyrimidin-2-ylmethyl, (4-amino)pyrimidin-2-ylmethyl, (6-amidino)pyrazin-2-ylmethyl, (6-amino)pyrazin-2-ylmethyl, 3-aminocyclohexyl, 3-amidinocyclohexyl, 3-aminocyclohexylmethyl, 3-amidinocyclohexylmethyl, 3-aminocyclopentyl, 3-amidinocyclopentyl, 3-aminocyclopentylmethyl, and 3-amidinocyclopentylmethyl;

$R_8$ is Br, I, $C_2H_5$, H, Cl, F, SH, SMe, $CF_3$, $CH_3$, $CO_2H$, $CO_2Me$, CN, $C(=NH)NH_2$, $C(=NH)NHOH$, $C(=NH)NHNH_2$, $C(=O)NH_2$, $CH_2OH$, $CH_2NH_2$, $NO_2$, OH, OMe, $OCH_2Ph$, $OCH_2CO_2H$, $O(CH_2)_2CO_2H$, $O(CH_2)_3CO_2H$, $NHCH_2CO_2H$, $NH(CH_2)_2CO_2H$, $NH(CH_2)_3CO_2H$, $OCH_2CH_2OH$, $OCH_2$(1H-tetrazol-5-yl), $NH_2$, NHButyl, $NMe_2$, NHPh, $NHCH_2Ph$, $NHC(=O)Me$, $NHC(=O)$c-Hexyl, $NHC(=O)CH_2$c-Hexyl, $NHC(=O)Ph$. $NHC(=O)CH_2Ph$, $NHS(=O)_2Me$, $NHS(=O)_2$c-Hexyl, $NHS(=O)_2CH_2$C-Hexyl, $NHS(=O)_2Ph$, and $NHS(=O)_2CH_2Ph$;

$R_9$ is $(CH_2)_5$, $(CH_2)_4$, $(CH_2)_6$, $CH_2C(=O)NHCH_2CH_2$, $CH_2CH_2NHC(=O)CH_2$, $(CH_2)_2NH(CH_2)_2$, $(CH_2)_2O(CH_2)_2$, $C_6H_4$, $CH_2C_6H_4$, $C_6H_4CH_2$, $C_6H_{10}$, $CH_2C_6H_{10}$, $C_6H_{10}CH_2$, $C_5H_8$, $CH_2C_5H_8$, $C_5H_8CH_2$, and $CH_2CH=CHCH_2CH_2$; and $R_{10}$ is piperidinyl, 2,6-dimethylpiperidinyl, 2,2,6,6-tetrainethyl-piperidinyl-4-one, 2,2,6,6-tetramethyl piperidinyl, (2-carboxy)piperidinyl, (3-carboxy)piperidinyl, (4-carboxy)piperidinyl, 3,5-dimethylpiperidinyl, (4-hydroxy)piperidinyl, (2-imino)piperidinyl, piperidin-4-one-yl, (2-dimethylaminomethyl)-piperidinyl, (4-dimethylamino)-piperidinyl, (4-sulphonyloxy)-piperidinyl, (2-phenyl)piperidinyl, 2,5-dimethylpyrrolidinyl, pyrrolidinyl, (2-carboxy)pyrrolidinyl, (3-N-acetyl-N-methyl)pyrrolidinyl, (3-amino)pyrrolidinyl, (2,5-bis-methoxymethyl)-pyrrolidinyl, 2-hydroxymethyl-pyrrolidinyl, 2-hydroxymethyl-5-methyl-pyrrolidinyl, diisopropylamino, diethylamino, methylamino, 1-methyl-4,5-dihydro-1H-imidazol-2-yl, 2,5-dimethyl-1H-1-imidazolyl, morpholinyl, 2,6-dimethylmorpholinyl, piperazinyl, 2,6-dimethylpiperazinyl, 1H-pyrazolyl, tetrahydro-1H-pyrazolyl, and 2,5-dimethyltetrahydro-1H-1-pyrazolyl.

In one embodiment of Formulas 7 and 8, $R_8$, $R_9$, and $R_{10}$ are as above and $R_7$ is (2-hydroxy, 5-amidino)phenyl. In another embodiment of Formulas 7 and 8, $R_7$, $R_9$, and $R_{10}$ are as above and $R_8$ is H. In another embodiment of Formulas 7 and 8, $R_7$, $R_8$, and $R_{10}$ are as above and $R_9$ is $(CH_2)_5$. In another embodiment of Formulas 7 and 8, $R_7$, $R_8$, and $R_{10}$ is 2,6-dimethylpiperidinyl. In another embodiment of Formulas 7 and 8, $R_7$ is as defined above and $R_8$ is H, $R_9$ is $(CH_2)_5$ and $R_{10}$ is 2,6-dimethylpiperidinyl. In another embodiment of Formulas 7 and 8, $R_7$ is as defined above and $R_8$ is H, $R_9$ is $(CH_2)_5$ and $R_{10}$ is 2,5-dimethylpyrrolidinyl.

Representative compounds of the present invention include:

3-(4-5-[(2R,6S)-2,6-dimethyltetrahydro-1(2H)-pyridinyl]pentyl-3-oxo-3,4-dihydro-2H-1,4-benzothiazin-2-yl)-4-methoxybenzenecarboximidamide;

3-(4-5-[(2R,6S)-2,6-Dimethyltetrahydro-1(2H)-pyridinyl]pentyl-3-oxo-3,4-dihydro-2H-1,4-benzothiazin-2-yl)benzenecarboximidamide:

4-5-[(2R,6S)-2,6-Dimethyltetrahydro-1(2H)-pyridinyl]pentyl-2-(3-hydroxyphenyl)-2H-1,4-benzothiazin-3(4H)-one;

3-(4-5-[(2R,6S)-2,6-Dimethyltetrahydro-1(2H)-pyridinyl]pentyl-3-oxo-3,4-dihydro-2H-1,4-benzothiazin-2-yl)-N-hydroxybenzenecarboximidamide;

3-(4-5-[(2R,6S)-2,6-Dimethyltetrahydro-1(2H)-pyridinyl]pentyl-3-oxo-3,4-dihydro-2H-1,4-benzothiazin-2-yl)-N-hydroxybenzenecarboximidamide;

3-(4-5-[(2R,6S)-2,6-Dimethyltetrahydro-1(2H)-pyridinyl]pentyl-3-oxo-3,4-dihydro-2H-1,4-benzothiazin-2-yl)benzenecarboximidohydrazide;

2-[3-(Aminomethyl)phenyl]-4-5-[(2R,6S)-2,6-dimethyltetrahydro-1(2H)-pyridinyl]pentyl-2H-1,4-benzothiazin-3(4H)-one;

2-(3-Aminophenyl)-4-5-[(2R,6S)-2,6-dimethyltetrahydro-1(2H)-pyridinyl]pentyl-2H-1,4-benzothiazin-3(41)-one;

4-5-[(2R,6S)-2,6-Dimethyltetrahydro-1(2H)-pyridinyl]pentyl-2-[3-(methylamino)phenyl]-2H-1,4-benzothiazin-3(4H)-one;

2-[3-(Dimethylamino)phenyl]-4-5-[(2R,6S)-2,6-dimethyltetrahydro-1(2H)-pyridinyl]pentyl-2H-1,4-benzothiazin-3(4H)-one;

3-(4-5-[(2R,6S)-2,6-Dimethyltetrahydro-1(2H)-pyridinyl]pentyl-3-oxo-3,4-dihydro-2H-1,4-benzothiazin-2-yl)-4-hydroxybenzenecarboximidamide;

3-(4-5-[(2R,6S)-2,6-Dimethyltetrahydro-1(2H)-pyridinyl]pentyl-3-oxo-3,4-dihydro-2H-1,4-benzothiazin-2-yl)tetrahydro-1(2H)-pyridinecarboximidamide;

3-(4-5-[(2R,6S)-2,6-Dimethyltetrahydro-1(2H)-pyridinyl]pentyl-3-oxo-3,4-dihydro-2H-1,4-benzothiazin-2-yl)-1-pyrrolidinecarboximidamide;

5-(4-5-[(2R,6S)-2,6-Dimethyltetrahydro-1(2H)-pyridinyl]pentyl-3-oxo-3,4-dihydro-2H-1,4-benzothiazin-2-yl)-2-thiophenecarboximidamide;

5-(4-5-[(2R,6S)-2,6-Dimethyltetrahydro-1(2H)-pyridinyl]pentyl-3-oxo-3,4-dihydro-2H-1,4-benzothiazin-2-yl)-2-furancarboximidamide;

2-(4-5-[(2R,6S)-2,6-Dimethyltetrahydro-1(2H)-pyridinyl]pentyl-3-oxo-3,4-dihydro-2H-1,4-benzothiazin-2-yl)-1,3-oxazole-5-carboximidamide;

5-(4-5-[(2R,6S)-2,6-Dimethyltetrahydro-1(2H)-pyridinyl]pentyl-3-oxo-3,4-dihydro-2H-1,4-benzothiazin-2-yl)-1,3-oxazole-2-carboximidamide;

4-5-[(2R,6S)-2,6-Dimethyltetrahydro-1(2H)-pyridinyl]pentyl-2-(1H-pyrazol-5-yl)-2H-1,4-benzothiazin-3(4H)-one;

5-(4-5-[(2R,6S)-2,6-Dimethyltetrahydro-1(2H)-pyridinyl]pentyl-3-oxo-3,4-dihydro-2H-1,4-benzothiazin-2-yl)-1-pyrazolidinecarboximidamide;

4-(4-5-[(2R,6S)-2,6-Dimethyltetrahydro-1(2H)-pyridinyl]pentyl-3-oxo-3,4-dihydro-2H-1,4-benzothiazin-2-yl)-1H-imidazole-2-carboximidamide;

2-(2-Amino-1H-imidazol-4-yl)-4-5-[(2R,6S)-2,6-dimethyltetrahydro-1(2H)-pyridinyl]pentyl-2H-1,4-benzothiazin-3(4H)-one;

2-(4-5-[(2R,6S)-2,6-Dimethyltetrahydro-1(2H)-pyridinyl]pentyl-3-oxo-3,4-dihydro-2H-1,4-benzothiazin-2-yl)-1H-imidazole-5-carboximidamide;

2-(5-Amino-1H-imidazol-2-yl)-4-5-[(2R,6S)-2,6-dimethyltetrahydro-1(2H)-pyridinyl]pentyl-2H-1,4-benzothiazin-3(4H)-one;

4-5-[(2R,6S)-2,6-Dimethyltetrahydro-1(2H)-pyridinyl]pentyl-2-(3-pyridinyl)-2H-1,4-benzothiazin-3(4H)-one;

2-(4-Amino-3-pyridinyl)-4-5-[(2R,6S)-2,6-dimethyltetrahydro-1(2H)-pyridinyl]pentyl-2H-1,4-benzothiazin-3(4H)-one;

2-[4-(Dimethylamino)-3-pyridinyl]-4-5-[(2R,6S)-2,6-dimethyltetrahydro-1(2H)-pyridinyl]pentyl-2H-1,4-benzothiazin-3(4H)-one;

2-(6-Amino-2-pyridinyl)-4-5-[(2R,6S)-2,6-dimethyltetrahydro-1(2H)-pyridinyl]pentyl-2H-1,4-benzothiazin-3(4H)-one;

6-(4-5-[(2R,6S)-2,6-Dimethyltetrahydro-1(2H)-pyridinyl]pentyl-3-oxo-3,4-dihydro-2H-1,4-benzothiazin-2-yl)-2-pyridinecarboximidamide;

2-(2-Amino4-pyridinyl)-4-5-[(2R,6S)-2,6-dimethyltetrahydro-1(2H)-pyridinyl]pentyl-2H-1,4-benzothiazin-3(4H)-one;

4-(4-5-[(2R,6S)-2,6-Dimethyltetrahydro-1(2H)-pyridinyl]pentyl-3-oxo-3,4-dihydro-2H-1,4-benzothiazin-2-yl)-2-pyridinecarboximidamide;

4-(4-5-[(2R,6S)-2,6-Dimethyltetrahydro-1(2H)-pyridinyl]pentyl-3-oxo-3,4-dihydro-2H-1,4-benzothiazin-2-yl)-2-pyrimidinecarboximidamide;

2-(2-Amino-4-pyrimidinyl)4-5-[(2R,6S)-2,6-dimethyltetrahydro-1(2H)-pyridinyl]pentyl-2H-1,4-benzothiazin-3(4H)-one;

2-(4-5-[(2R,6S)-2,6-Dimethyltetrahydro-1(2H)-pyridinyl]pentyl-3-oxo-3,4-dihydro-2H-1,4-benzothiazin-2-yl)-4-pyrimidinecarboximidamide;

2-(4-Amino-2-pyrimidinyl)-4-5-[(2R,6S)-2,6-dimethyltetrahydro-1(2H)-pyridinyl]pentyl-2H-1,4-benzothiazin-3(4H)-one;

6-(4-5-[(2R,6S)-2,6-Dimethyltetrahydro-1(2H)-pyridinyl]pentyl-3-oxo-3,4-dihydro-2H-1,4-benzothiazin-2-yl)-2-pyrazinecarboximidamide;

2-(6-Amino-2-pyrazinyl)-4-5-[(2R,6S)-2,6-dimethyltetrahydro-1(2H)-pyridinyl]pentyl-2H-1,4-benzothiazin-3(4H)-one;

4-(4-5-[(2R,6S)-2,6-Dimethyltetrahydro-1(2H)-pyridinyl]pentyl-3-oxo-3,4-dihydro-2H-1,4-benzothiazin-2-yl)-1,3,5-triazine-2-carboximidamide;

2-(4-Amino-1,3,5-triazin-2-yl)-4-5-[(2R,6S)-2,6-dimethyltetrahydro-1(2H)-pyridinyl]pentyl-2H-1,4-benzothiazin-3(4H)-one;

5-(4-5-[(2R,6S)-2,6-Dimethyltetrahydro-1(2H)-pyridinyl]pentyl-3-oxo-3,4-dihydro-2H-1,4-benzothiazin-2-yl)-1,2,4-triazine-3-carboximidamide;

2-(3-Amino-1,2,4-triazin-5-yl)-4-5-[(2R,6S)-2,6-dimethyltetrahydro-1(2H)-pyridinyl]pentyl-2H-1,4-benzothiazin-3(4H)-one;

3-[(4-5-[(2R,6S)-2,6-Dimethyltetrahydro-1(2H)-pyridinyl]pentyl-3-oxo-3,4-dihydro-2H-1,4-benzothiazin-2-yl)methyl]benzenecarboximidamide;

2-(3-Aminobenzyl)-4-5-[(2R,6S)-2,6-dimethyltetrahydro-1(2H)-pyridinyl]pentyl-2H-1,4-benzothiazin-3(4H)-one;

2-[3-(Aminomethyl)benzyl]-4-5-[(2R,6S)-2,6-dimethyltetrahydro-1(2H)-pyridinyl]pentyl-2H-1,4-benzothiazin-3(41)-one;

3-[(4-5-[(2R,6S)-2,6-Dimethyltetrahydro-1(2H)-pyridinyl]pentyl-3-oxo-3,4-dihydro-2H-1,4-benzothiazin-2-yl)methyl]tetrahydro-1(2H)-pyridinecarboximidamide;

3-[(4-5-[(2R,6S)-2,6-Dimethyltetrahydro-1(2H)-pyridinyl]pentyl-3-oxo-3,4-dihydro-2H-1,4-benzothiazin-2-yl)methyl]-1-pyrrolidinecarboximidamide;

5-[(4-5-[(2R,6S)-2,6-Dimethyltetrahydro-1(2H)-pyridinyl]pentyl-3-oxo-3,4-dihydro-2H-1,4-benzothiazin-2-yl)methyl]-2-thiophenecarboximidamide;

5-[(4-5-[(2R,6S)-2,6-Dimethyltetrahydro-1(2H)-pyridinyl]pentyl-3-oxo-3,4-dihydro-2H-1,4-benzothiazin-2-yl)methyl]-2-furancarboximidamide;

2-[(4-5-[(2R,6S)-2,6-Dimethyltetrahydro-1(2H)-pyridinyl]pentyl-3-oxo-3,4-dihydro-2H-1,4-benzothiazin-2-yl)methyl]-1,3-oxazole-5-carboximidamide;

5-[(4-5-[(2R,6S)-2,6-Dimethyltetrahydro-1(2H)-pyridinyl]pentyl-3-oxo-3,4-dihydro-2H-1,4-benzothiazin-2-yl)methyl]-1H-imidazole-2-carboximidamide;

2-[(4-5-[(2R,6S)-2,6-Dimethyltetrahydro-1(2H)-pyridinyl]pentyl-3-oxo-3,4-dihydro-2H-1,4-benzothiazin-2-yl)methyl]-1H-imidazole-5-carboximidamide;

6-[(4-5-[(2R,6S)-2,6-Dimethyltetrahydro-1(2H)-pyridinyl]pentyl-3-oxo-3,4-dihydro-2H-1,4-benzothiazin-2-yl)methyl]-2-pyridinecarboximidamide;

2-[(6-Amino-2-pyridinyl)methyl]-4-5-[(2R,6S)-2,6-dimethyltetrahydro-1(2H)-pyridinyl]pentyl-2H-1,4-benzothiazin-3(4H)-one;

4-[(4-5-[(2R,6S)-2,6-Dimethyltetrahydro-1(2H)-pyridinyl]pentyl-3-oxo-3,4-dihydro-2H-1,4-benzothiazin-2-yl)methyl]-2-pyrimidinecarboximidamide;

2-[(2-Amino-4-pyrimidinyl)methyl]4-5-[(2R,6S)-2,6-dimethyltetrahydro-1(2H)-pyridinyl]pentyl-2H-1,4-benzothiazin-3(4H)-one;

2-[(4-5-[(2R,6S)-2,6-Dimethyltetrahydro-1(2H)-pyridinyl]pentyl-3-oxo-3,4-dihydro-2H-1,4-benzothiazin-2-yl)methyl]-4-pyrimidinecarboximidamide;

2-[(4-Amino-2-pyrimidinyl)methyl]-4-5-[(2R,6S)-2,6-dimethyltetrahydro-1(2H)-pyridinyl]pentyl-2H-1,4-benzothiazin-3(4H)-one;

6-[(4-5-[(2R,6S)-2,6-Dimethyltetrahydro-1(2H)-pyridinyl]pentyl-3-oxo-3,4-dihydro-2H-1,4-benzothiazin-2-yl)methyl]-2-pyrazinecarboximidamide;

2-[(6-Amino-2-pyrazinyl)methyl]4-5-[(2R,6S)-2,6-dimethyltetrahydro-1(2H)-pyridinyl]pentyl-2H-1,4-benzothiazin-3(4H)-one;

2-(3-Aminocyclohexyl)-4-5-[(2R,6S)-2,6-dimethyltetrahydro-1(2H)-pyridinyl]pentyl-2H-1,4-benzothiazin-3(4H)-one;

3-(4-5-[(2R,69)-2,6-Dimethyltetrahydro-1(2H)-pyridinyl]pentyl-3-oxo-3,4-dihydro-2H-1,4-benzothiazin-2-yl)cyclohexanecarboximidamide;

2-[(3-Aminocyclohexyl)methyl]-4-5-[(2R,6S)-2,6-dimethyltetrahydro-1(2H)-pyridinyl]pentyl-2H-1,4-benzothiazin-3(4H)-one;

3-[(4-5-[(2R,6S)-2,6-Dimethyltetrahydro-1(2H)-pyridinyl]pentyl-3-oxo-3,4-dihydro-2H-1,4-benzothiazin-2-yl)methyl] cyclohexanecarboximidamide;

2-(3-Aminocyclopentyl)-4-5-[(2R,6S)-2,6-dimethyltetrahydro-1(2H)-pyridinyl]pentyl-2H-1,4-benzothiazin-3(4H)-one;

3-(4-5-[(2R,6S)-2,6-Dimethyltetrahydro-1(2H)-pyridinyl]pentyl-3-oxo-3,4-dihydro-2H-1,4-benzothiazin-2-yl)cyclopentanecarboximidamide;

2-[(3-Aminocyclopentyl)methyl]-4-5-[(2R,6S)-2,6-dimethyltetrahydro-1(2H)-pyridinyl]pentyl-2H-1,4-benzothiazin-3(4H)-one;

3-[(4-5-[(2R,6S)-2,6-Dimethyltetrahydro-1(2H)-pyridinyl]pentyl-3-oxo-3,4-dihydro-2H-1,4-benzothiazin-2-yl)methyl] cyclopentanecarboximidamide;

3-(4-4-[(2R,6S)-2,6-Dimethyltetrahydro-1(2H)-pyridinyl]butyl-3-oxo-3,4-dihydro-2H-1,4-benzothiazin-2-yl)benzenecarboximidamide;

3-(4-6-[(2R,6S)-2,6-Dimethyltetrahydro-1(2H)-pyridinyl]hexyl-3-oxo-3,4-dihydro-2H-1,4-benzothiazin-2-yl)benzenecarboximidamide;

2-(2-3-[Amino(imino)methyl]phenyl-3-oxo-2,3-dihydro-4H-1,4-benzothiazin-4-yl)-N-2-[(2R,6S)-2,6-dimethyltetrahydro-1(2H)-pyridinyl]ethylacetamide;

3-(2-3-[Amino(imino)methyl]phenyl-3-oxo-2,3-dihydro-4H-1,4-benzothiazin-4-yl)-N-[(2R,6S)-2,6-dimethyltetrahydro-1(2H)-pyridinyl]methylpropanamide;

3-4-[2-(2-[(2R,6S)-2,6-Dimethyltetrahydro-1(2H)-pyridinyl]ethylamino)ethyl]-3-oxo-3,4-dihydro-2H-1,4-benzothiazin-2-ylbenzenecarboximidamide;

3-[4-(2-2-[(2R,6S)-2,6-Dimethyltetrahydro-1(2H)-pyridinyl]ethoxyethyl)-3-oxo-3,4-dihydro-2H-1,4-benzothiazin-2-yl]benzenecarboximidamide;

3-(4-4-[(2R,6S)-2,6-Dimethyltetrahydro-1(2H)-pyridinyl]phenyl-3-oxo-3,4-dihydro-2H-1,4-benzothiazin-2-yl)benzenecarboximidamide;

3-(4-4-[(2R,6S)-2,6-Dimethyl tetrahydro-1(2H)-pyridinyl]benzyl-3-oxo-3,4-dihydro-2H-1,4-benzothiazin-2-yl)benzenecarboximidamide;

3-[4-(4-[(2R,6S)-2,6-Dimethyltetrahydro-1(2H)-pyridinyl]methylphenyl)-3-oxo-3,4-dihydro-2H-1,4-benzothiazin-2-yl]benzenecarboximidamide.

3-(4-4-[(2R,6S)-2,6-Dimethyltetrahydro-1(2H)-pyridinyl]cyclohexyl-3-oxo-3,4-dihydro-2H-1,4-benzothiazin-2-yl)benzenecarboximidamide;

3-[4-(4-[(2R,6S)-2,6-Dimethyltetrahydro-1(2H)-pyridinyl]cyclohexylmethyl)-3-oxo-3,4-dihydro-2H-1,4-benzothiazin-2-yl]benzenecarboximidamide;

3-[4-(4-[(2R,6S)-2,6-Dimethyltetrahydro-1(2H)-pyridinyl]methylcyclohexyl)-3-oxo-3,4-dihydro-2H-1,4-benzothiazin-2-yl]benzenecarboximidamide;

3-(4-3-[(2R,6S)-2,6-Dimethyltetrahydro-1(2H)-pyridinyl]cyclopentyl-3-oxo-3,4-dihydro-2H-1,4-benzothiazin-2-yl)benzenecarboximidamide;

3-[4-(3-[(2R,6S)-2,6-Dimethyltetrahydro-1(2H)-pyridinyl]cyclopentylmethyl)-3-oxo-3,4-dihydro-2H-1,4-benzothiazin-2-yl]benzenecarboximidamide;

3-[4-(3-[(2R,6S)-2,6-Dimethyltetrahydro-1(2H)-pyridinyl]methylcyclopentyl)-3-oxo-3,4-dihydro-2H-1,4-benzothiazin-2-yl]benzenecarboximidamide;

3-(4-(E)-5-[(2R,6S)-2,6-Dimethyltetrahydro-1(2H)-pyridinyl]-2-pentenyl-3-oxo-3,4-dihydro-2H-1,4-benzothiazin-2-yl)benzenecarboximidamide;

3-[3-Oxo-4-(5-piperidinopentyl)-3,4-dihydro-2H-1,4-benzothiazin-2-yl]benzenecarboximidamide;

3-3-Oxo-4-[5-(2,2,6,6-tetramethylpiperidino)pentyl]-3,4-dihydro-2H-1,4-benzothiazin-2-ylbenzenecarboximidamide;

1-[5-(2-3-[Amino(imino)methyl]phenyl-3-oxo-2,3-dihydro-4H-1,4-benzothiazin-4-yl)pentyl]-2-piperidinecatboxylic acid;

1-[5-(2-3-[Amino(imino)methyl]phenyl-3-oxo-2,3-dihydro-4H-1,4-benzothiazin-4-yl)pentyl]-3-piperidinecarboxylic acid;

1-[5-(2-3-[Amino(imino)methyl]phenyl-3-oxo-2,3-dihydro-4H-1,4-benzothiazin-4-yl)pentyl]-4-piperidinecarboxylic acid;

3-4-[5-(3,5-Dimethylpiperidino)pentyl]-3-oxo-3,4-dihydro-2H-1,4-benzothiazin-2-ylbenzenecarboximidamide;

3-4-[5-(4-Hydroxypiperidino)pentyl]-3-oxo-3,4-dihydro-2H-1,4-benzothiazin-2-ylbenzenecarboximidamide;

3-4-[5-(2-Iminopiperidino)pentyl]-3-oxo-3,4-dihydro-2H-1,4-benzothiazin-2-ylbenzenecarboximidamide;

3-3-Oxo-4-[5-(4-oxopiperidino)pentyl]-3,4-dihydro-2H-1,4-benzothiazin-2-ylbenzenecarboximidamide;

3-[4-(5-2-[(Dimethylamino)methyl]piperidinopentyl)-3-oxo-3,4-dihydro-2H-1,4-benzothiazin-2-yl]benzenecarboximidainide;

3-(4-5-[4-(Dimethylamino)piperidino]pentyl-3-oxo-3,4-dihydro-2H-1,4-benzothiazin-2-yl)benzenecarboximidamide;

1-[5-(2-3-[Amino(imino)methyl]phenyl-3-oxo-2,3-dihydro-4H-1,4-benzothiazin-4-yl)pentyl]-4-piperidinesulfonic acid;

3-3-Oxo-4-[5-(2-phenylpiperidino)pentyl]-3,4-dihydro-2H-1,4-benzothiazin-2-ylbenzenecarboximidamide;

3-4-[5-(2,5-Dimethyl-1-pyrrolidinyl)pentyl]-3-oxo-3,4-dihydro-2H-1,4-benzothiazin-2-ylbenzenecarboximidamide;

3-3-Oxo-4-[5-(1-pyrrolidinyl)pentyl]-3,4-dihydro-2H-1,4-benzothiazin-2-ylbenzenecarboximidamide;

1-[5-(2-3-[Amino(imino)methyl]phenyl-3-oxo-2,3-dihydro-4H-1,4-benzothiazin-4-yl)pentyl]-2-pyrrolidinecarboxylic acid;

N-1-[5-(2-3-[Amino(imino)methyl]phenyl-3-oxo-2,3-dihydro-4H-1,4-benzothiazin-4-yl)pentyl]tetrahydro-1H-pyrrol-3-yl-N-methylacetamide;

3-4-[5-(3-Amino-1-pyrrolidinyl)pentyl]-3-oxo-3,4-dihydro-2H-1,4-benzothiazin-2-ylbenzenecarboximidamide;

3-(4-5-[2,5-Bis(methoxymethyl)-1-pyrrolidinyl]pentyl-3-oxo-3,4-dihydro-2H-1,4-benzothiazin-2-yl)benzenecarboximidamide;

3-(4-5-[2-(Hydroxymethyl)-1-pyrrolidinyl]pentyl-3-oxo-3,4-dihydro-2H-1,4-benzothiazin-2-yl)benzenecarboximidamide;

3-(4-5-[2-(Hydroxymethyl)-5-methyl-1-pyrrolidinyl]pentyl-3-oxo-3,4-dihydro-2H-1,4-benzothiazin-2-yl)benzenecarboximidamide;

3-4-[5-(Diisopropylamino)pentyl]-3-oxo-3,4-dihydro-2H-1,4-benzothiazin-2-ylbenzenecarboximidamide;

3-4-[5-(Diethylamino)pentyl]-3-oxo-3,4-dihydro-2H-1,4-benzothiazin-2-ylbenzenecarboximidamide;

3-4-[5-(Methylamino)pentyl]-3-oxo-3,4-dihydro-2H-1,4-benzothiazin-2-ylbenzenecarboximidamide;

3-4-[5-(1-Methyl-1H-imidazol-2-yl)pentyl]-3-oxo-3,4-dihydro-2H-1,4-benzothiazin-2-ylbenzenecarboximidamide;

3-4-[5-(2,5-Dimethyl-1H-imidazol-1-yl)pentyl]-3-oxo-3,4-dihydro-2H-1,4-benzothiazin-2-ylbenzenecarboximidamide;

3-[4-(5-Morpholinopentyl)-3-oxo-3,4-dihydro-2H-1,4-benzothiazin-2-yl]benzenecarboximidamide;

3-4-[5-(3,5-Dimethylmorpholino)pentyl]-3-oxo-3,4-dihydro-2H-1,4-benzothiazin-2-ylbenzenecarboximidamide;

3-[3-Oxo-4-(5-piperazinopentyl)-3,4-dihydro-2H-1,4-benzothiazin-2-yl]benzenecarboximidamide;

3-4-[5-(2,6-Dimethylpiperazino)pentyl]-3-oxo-3,4-dihydro-2H-1,4-benzothiazin-2-ylbenzenecarboximidamide;

3-3-Oxo-4-[5-(1H-pyrazol-1-yl)pentyl]-3,4-dihydro-2H-1,4-benzothiazin-2-ylbenzenecarboximidamide;

3-[3-Oxo-4-(5-tetrahydro-1H-pyrazol-1-ylpentyl)-3,4-dihydro-2H-1,4-benzothiazin-2-yl]benzenecarboximidamide;

3-4-[5-(2,5-Dimethyltetrahydro-1H-pyrazol-1-yl)pentyl]-3-oxo-3,4-dihydro-2H-1,4-benzothiazin-2-ylbenzenecarboximidamide;

3-(6-Chloro-4-5-[(2R,6S)-2,6-dimethyltetrahydro-1(2H)-pyridinyl]pentyl-3-oxo-3,4-dihydro-2H-1,4-benzothiazin-2-yl)benzenecarboximidamide;

3-(4-5-[(2R,6S)-2,6-Dimethyltetrahydro-1(2H)-pyridinyl]pentyl-6-fluoro-3-oxo-3,4-dihydro-2H-1,4-benzothiazin-2-yl)benzenecarboximidamide;

3-(4-5-[(2R,6S)-2,6-Dimethyltetrahydro-1(2H)-pyridinyl]pentyl-3-oxo-6-sulfanyl-3,4-dihydro-2H-1,4-benzothiazin-2-yl)benzenecarboximidamide;

3-[4-5-[(2R,6S)-2,6-Dimethyltetrahydro-1(2H)-pyridinyl]pentyl-6-(methylsulfanyl)-3-oxo-3,4-dihydro-2H-1,4-benzothiazin-2-yl]benzenecarboximidamide;

3-[4-5-[(2R,6S)-2,6-Dimethyltetrahydro-1(2H)-pyridinyl]pentyl-3-oxo-6-(trifluoromethyl)-3,4- dihydro-2H-1,4-benzothiazin-2-yl]
benzenecarboximidamide;

3-(4-5-[(2R,6S)-2,6-Dimethyltetrahydro-1(2H)-pyridinyl]pentyl-6-methyl-3-oxo-3,4-dihydro-2H-1,4-benzothiazin-2-yl)benzenecarboximidamide;

2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazine-6-carboxylic acid;

Methyl 2-3-[amino(imino)methyl]phenyl-4-5-[(2R,6S)-2,6-dimethyltetrahydro-1(2H)-pyridinyl]pentyl-3-oxo-3,4-dihydro-2H-1,4-benzothiazine-6-carboxylate;

3-(6-Cyano-4-5-[(2R,6S)-2,6-dimethyltetrahydro-1(2H)-pyridinyl]pentyl-3-oxo-3,4-dihydro-2H-1,4-benzothiazin-2-yl)benzenecarboximidamide;

2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazine-6-carboximidamide;

2-3-[amino(imino)methyl]phenyl-4-5-[(2R,6S)-2,6-dimethyltetrahydro-1(2H)-pyridinyl]pentyl-N-hydroxy-3-oxo-3,4-dihydro-2H-1,4-benzothiazine-6-carboximidamide;

3-4-5-[(2R,6S)-2,6-Dimethyltetrahydro-1(2H)-pyridinyl]pentyl-6-[hydrazino(imino)methyl]-3-oxo-3,4-dihydro-2H-1,4-benzothiazin-2-ylbenzenecarboximidamide;

2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazine-6-carboxamide;

3-[4-5-[(2R,6S)-2,6-Dimethyltetrahydro-1(2H)-pyridinyl]pentyl-6-(hydroxymethyl)-3-oxo-3,4-dihydro-2H-1,4-benzothiazin-2-yl]benzenecarboximidamide;

3-(6-(Aminomethyl)-4-5-[(2R,6S)-2,6-dimethyltetrahydro-1(2H)-pyridinyl]pentyl-3-oxo-3,4-dihydro-2H-1,4-benzothiazin-2-yl)benzenecarboximidamide;

3-(4-5-[(2R,6S)-2,6-Dimethyltetrahydro-1(2H)-pyridinyl]pentyl-6-nitro-3-oxo-3,4-dihydro-2H-1,4-benzothiazin-2-yl)benzenecarboximidamide;

3-(4-5-[(2R,6S)-2,6-Dimethyltetrahydro-1(2H)-pyridinyl]pentyl-6-hydroxy-3-oxo-3,4-dihydro-2H-1,4-benzothiazin-2-yl)benzenecarboximidamide;

3-(4-5-[(2R,6S)-2,6-Dimethyltetrahydro-1(2H)-pyridinyl]pentyl-6-methoxy-3-oxo-3,4-dihydro-2H-1,4-benzothiazin-2-yl)benzenecarboximidamide;

3-(6-(Benzyloxy)4-5-[(2R,6S)-2,6-dimethyltetrahydro-1(2H)-pyridinyl]pentyl-3-oxo-3,4-dihydro-2H-1,4-benzothiazin-2-yl)benzenecarboximidamide;

2-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazin-6-yl)oxy]acetic acid;

3-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazin-6-yl)oxy]propanoic acid;

4-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazin-6-yl)oxy]butanoic acid;

2-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazin-6-yl)amino]acetic acid;

3-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazin-6-yl)amino]propanoic acid;

4-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazin-6-yl)amino]butanoic acid;

3-[4-5-[(2R,6S)-2,6-Dimethyltetrahydro-1(2H)-pyridinyl]pentyl-6-(2-hydroxyethoxy)-3-oxo-3,4-dihydro-2H-1,4-benzothiazin-2-yl]benzenecarboximidamide;

3-[4-5-[(2R,6S)-2,6-Dimethyltetrahydro-1(2H)-pyridinyl]pentyl-3-oxo-6-(2H-1,2,3,4-tetraazol-5-ylmethoxy)-3,4-dihydro-2H-1,4-benzothiazin-2-yl]benzenecarboximidamide;

3-(6-Amino4-5-[(2R,6S)-2,6-dimethyltetrahydro-1(2H)-pyridinyl]pentyl-3-oxo-3,4-dihydro-2H-1,4-benzothiazin-2-yl)benzenecarboximidamide;

3-(6-(Butylamino)-4-5-[(2R,6S)-2,6-dimethyltetrahydro-1(2H)-pyridinyl]pentyl-3-oxo-3,4-dihydro-2H-1,4-benzothiazin-2-yl)benzenecarboximidamide;

3-(6-(Dimethylamino)-4-5-[(2R,6S)-2,6-dimethyltetrahydro-1(2H)-pyridinyl]pentyl-3-oxo-3,4-dihydro-2H-1,4-benzothiazin-2-yl)benzenecarboximidamide;

3-(6-Anilino-4-5-[(2R,6S)-2,6-dimethyltetrahydro-1(2H)-pyridinyl]pentyl-3-oxo-3,4-dihydro-2H-1,4-benzothiazin-2-yl)benzenecarboximidamide;

3-(6-(Benzylamino)-4-5-[(2R,6S)-2,6-dimethyltetrahydro-1(2H)-pyridinyl]pentyl-3-oxo-3,4-dihydro-2H-1,4-benzothiazin-2-yl)benzenecarboximidamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazin-6-yl)acetamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazin-6-yl)cyclohexanecarboxamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazin-6-yl)-2-cyclohexylacetamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazin-6-yl)benzenecarboxamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzothiazin-6-yl)-2-phenylacetamide;

3-4-5-[(2R,6S)-2,6-Dimethyltetrahydro-1(2H)-pyridinyl]pentyl-6-[(methylsulfonyl)amino]-3-oxo-3,4-dihydro-2H-1,4-benzothiazin-2-ylbenzenecarboximidamide;

3-(6-[(Cyclohexylsulfonyl)amino]-4-5-[(2R,6S)-2,6-dimethyltetrahydro-1(2H)-pyridinyl]pentyl-3-oxo-3,4-dihydro-2H-1,4-benzothiazin-2-yl)benzenecarboximidamide;

3-(6-[(Cyclohexylmethyl)sulfonyl]amino-4-5-[(2R,6S)-2,6-dimethyltetrahydro-1(2H)-pyridinyl]pentyl-3-oxo-3,4-dihydro-2H-1,4-benzothiazin-2-yl)benzenecarboximidamide;

3-4-5-[(2R,6S)-2,6-Dimethyltetrahydro-1(2H)-pyridinyl]pentyl-3-oxo-6-[(phenylsulfonyl)amino]-3,4-dihydro-2H-1,4-benzothiazin-2-ylbenzenecarboximidamide;

3-(6-[(Benzylsulfonyl)amino]-4-5-[(2R,6S)-2,6-dimethyltetrahydro-1(2H)-pyridinyl]pentyl-3-oxo-3,4- dihydro-2H-1,4-benzothiazin-2-yl)
benzenecarboximidamide;

3-(4-5-[(2R,6S)-2,6-dimethyltetrahydro-1(2H)-pyridinyl]
pentyl-3-oxo-3,4-dihydro-2H-1,4-benzoxazin-2-yl)-4-
methoxybenzenecarboximidamide;

3-(4-5-[(2R,6S)-2,6-Dimethyltetrahydro-1(2H)-
pyridinyl]pentyl-3-oxo-3,4-dihydro-2H-1,4-
benzoxazin-2-yl)benzenecarboximidamide;

4-5-[(2R,6S)-2,6-Dimethyltetrahydro-1(2H)-pyridinyl]
pentyl-2-(3-hydroxyphenyl)-2H-1,4-benzoxazin-3
(4H)-one;

3-(4-5-[(2R,6S)-2,6-Dimethyltetrahydro-1(2H)-
pyridinyl]pentyl-3-oxo-3,4-dihydro-2H-1,4-
benzoxazin-2-yl)-N-
hydroxybenzenecarboximidamide;

3-(4-5-[(2R,6S)-2,6-Dimethyltetrahydro-1(2H)-
pyridinyl]pentyl-3-oxo-3,4-dihydro-2H-1,4-
benzoxazin-2-yl)benzenecarboximidohydrazide;

2-[3-(Aminomethyl)phenyl]-4-5-[(2R,6S)-2,6-
dimethyltetrahydro-1(2H)-pyridinyl]pentyl-2H-1,4-
benzoxazin-3(4H)-one;

2-(3-Aminophenyl)-4-5-[(2R,6S)-2,6-
dimethyltetrahydro-1(2H)-pyridinyl]pentyl-2H-1,4-
benzoxazin-3(4H)-one;

4-5-[(2R,6S)-2,6-Dimethyltetrahydro-1(2H)-pyridinyl]
pentyl-2-[3-(methylamino)phenyl]-2H-1,4-
benzoxazin-3(4H)-one;

2-[3-(Dimethylamino)phenyl]-4-5-[(2R,6S)-2,6-
dimethyltetrahydro-1(2H)-pyridinyl]pentyl-2H-1,4-
benzoxazin-3(4H)-one;

3-(4-5-[(2R,6S)-2,6-Dimethyltetrahydro-1(2H)-
pyridinyl]pentyl-3-oxo-3,4-dihydro-2H-1,4-
benzoxazin-2-yl)-4-hydroxybenzenecarboximidamide;

3-(4-5-[(2R,6S)-2,6-Dimethyltetrahydro-1(2H)-
pyridinyl]pentyl-3-oxo-3,4-dihydro-2H-1,4-
benzoxazin-2-yl)tetrahydro-1(2H)-
pyridinecarboximidamide;

3-(4-5-[(2R,6S)-2,6-Dimethyltetrahydro-1(2H)-
pyridinyl]pentyl-3-oxo-3,4-dihydro-2H-1,4-
benzoxazin-2-yl)-1-pyrrolidinecarboximidamide;

5-(4-5-[(2R,6S)-2,6-Dimethyltetrahydro-1(2H)-
pyridinyl]pentyl-3-oxo-3,4-dihydro-2H-1,4-
benzoxazin-2-yl)-2-thiophenecarboximidamide;

5-(4-5-[(2R,6S)-2,6-Dimethyltetrahydro-1(2H)-
pyridinyl]pentyl-3-oxo-3,4-dihydro-2H-1,4-
benzoxazin-2-yl)-2-furancarboximidamide;

2-(4-5-[(2R,6S)-2,6-Dimethyltetrahydro-1(2H)-
pyridinyl]pentyl-3-oxo-3,4-dihydro-2H-1,4-
benzoxazin-2-yl)-1,3-oxazole-5-carboximidamide;

5-(4-5-[(2R,6S)-2,6-Dimethyltetrahydro-1(2H)-
pyridinyl]pentyl-3-oxo-3,4-dihydro-2H-1,4-
benzoxazin-2-yl)-1,3-oxazole-2-carboximidamide;

4-5-[(2R,6S)-2,6-Dimethyltetrahydro-1(2H)-pyridinyl]
pentyl-2-(1H-pyrazol-5-yl)-2H-1,4-benzoxazin-3(4H)-
one;

4-5-[(2R,6S)-2,6-Dimethyltetrahydro-1(2H)-pyridinyl]
pentyl-2-tetrahydro-1H-pyrazol-3-yl-2H-1,4-
benzoxazin-3(4H)-one;

5-(4-5-[(2R,6S)-2,6-Dimethyltetrahydro-1(2H)-
pyridinyl]pentyl-3-oxo-3,4-dihydro-2H-1,4-
benzoxazin-2-yl)-1-pyrazolidinecarboximidamide;

4-(4-5-[(2R,6S)-2,6-Dimethyltetrahydro-1(2H)-
pyridinyl]pentyl-3-oxo-3,4-dihydro-2H-1,4-
benzoxazin-2-yl)-1H-imidazole-2-carboximidamide;

2-(2-Amino-1H-imidazol-4-yl)-4-5-[(2R,6S)-2,6-
dimethyltetrahydro-1(2H)-pyridinyl]pentyl-2H-1,4-
benzoxazin-3(4H)-one;

2-(4-5-[(2R,6S)-2,6-Dimethyltetrahydro-1(2H)-
pyridinyl]pentyl-3-oxo-3,4-dihydro-2H-1,4-
benzoxazin-2-yl)-1H-imidazole-5-carboximidamide;

2-(5-Amino-1H-imidazol-2-yl)-4-5-[(2R,6S)-2,6-
dimethyltetrahydro-1(2H)-pyridinyl]pentyl-2H-1,4-
benzoxazin-3(4H)-one;

4-5-[(2R,6S)-2,6-Dimethyltetrahydro-1(2H)-pyridinyl]
pentyl-2-(3-pyridinyl)-2H-1,4-benzoxazin-3(4H)-one;

2-(4-Amino-3-pyridinyl)-4-5-[(2R,6S)-2,6-
dimethyltetrahydro-1(2H-pyridinyl]pentyl-2H-1,4-
benzoxazin-3(4H)-one;

2-[4-(Dimethylamino)-3-pyridinyl]-4-5-[(2R,6S)-2,6-
dimethyltetrahydro-1(2H)-pyridinyl]pentyl-2H-1,4-
benzoxazin-3(4H)-one;

2-(6-Amino-2-pyridinyl)-4-5-[(2R,6S)-2,6-
dimethyltetrahydro-1(2H-pyridinyl]pentyl-2H-1,4-
benzoxazin-3(4H)-one;

6-(4-5-[(2R,6S)-2,6-Dimethyltetrahydro-1(2H1)-
pyridinyl]pentyl-3-oxo-3,4-dihydro-2H-1,4-
benzoxazin-2-yl)-2-pyridinecarboximidamide;

2-(2-Amino-4-pyridinyl)-4-5-[(2R,6S)-2,6-
dimethyltetrahydro-1(2H)-pyridinyl]pentyl-2H-1,4-
benzoxazin-3(4H)-one;

4-(4-5-[(2R,6S)-2,6-Dimethyltetrahydro-1(2H)-
pyridinyl]pentyl-3-oxo-3,4-dihydro-2H-1,4-
benzoxazin-2-yl)-2-pyridinecarboximidamide;

4-(4-5-[(2R,6S)-2,6-Dimethyltetrahydro-1(2H)-
pyridinyl]pentyl-3-oxo-3,4-dihydro-2H-1,4-
benzoxazin-2-yl)-2-pyrimidinecarboximidamide;

2-(2-Amino-4-pyrimidinyl)-4-5-[(2R,6S)-2,6-
dimethyltetrahydro-1(2H)-pyridinyl]pentyl-2H-1,4-
benzoxazin-3(4H)-one;

2-(4-5-[(2R,6S)-2,6-Dimethyltetrahydro-1(2H)-
pyridinyl]pentyl-3-oxo-3,4-dihydro-2H-1,4-
benzoxazin-2-yl)-4-pyrimidinecarboximidamide;

2-(4-Amino-2-pyrimidinyl)-4-5-[(2R,6S)-2,6-
dimethyltetrahydro-1(2H)-pyridinyl]pentyl-2H-1,4-
benzoxazin-3(4H)-one;

6-(4-5-[(2R,6S)-2,6-Dimethyltetrahydro-1(2H)-
pyridinyl]pentyl-3-oxo-3,4-dihydro-2H-1,4-
benzoxazin-2-yl)-2-pyrazinecarboximidamide;

2-(6-Amino-2-pyrazinyl)-4-5-[(2R,6S)-2,6-
dimethyltetrahydro-1(2H)-pyridinyl]pentyl-2H-1,4-
benzoxazin-3(4H)-one;

4-(4-5-[(2R,6S)-2,6-Dimethyltetrahydro-1(2H)-
pyridinyl]pentyl-3-oxo-3,4-dihydro-2H-1,4-
benzoxazin-2-yl)-1,3,5-triazine-2-carboximidamide;

2-(4-Amino-1,3,5-triazin-2-yl)-4-5-[(2R,6S)-2,6-
dimethyltetrahydro-1(2H)-pyridinyl]pentyl-2H-1,4-
benzoxazin-3(4H)-one;

5-(4-5-[(2R,6S)-2,6-Dimethyltetrahydro-1(2H)-
pyridinyl]pentyl-3-oxo-3,4-dihydro-2H-1,4-
benzoxazin-2-yl)-1,2,4-triazine-3-carboximidamide;

2-(3-Amino-1,2,4-triazin-5-yl)-4-5-[(2R,6S)-2,6-
dimethyltetrahydro-1(2H)-pyridinyl]pentyl-2H-1,4-
benzoxazin-3(4H)-one;

3-[(4-5-[(2R,6S)-2,6-Dimethyltetrahydro-1(2H)-
pyridinyl]pentyl-3-oxo-3,4-dihydro-2H-1,4-
benzoxazin-2-yl)methyl]benzenecarboximidamide;

2-(3-Aminobenzyl)-4-5-[(2R,6S)-2,6-
dimethyltetrahydro-1(2H)-pyridinyl]pentyl-2H-1,4-
benzoxazin-3(4H)-one;

2-[3-(Aminomethyl)benzyl]-4-5-[(2R,6S)-2,6-dimethyltetrahydro-1(2H)-pyridinyl]pentyl-2H-1,4-benzoxazin-3(4H)-one;

3-[(4-5-[(2R,6S)-2,6-Dimethyltetrahydro-1(2H)-pyridinyl]pentyl-3-oxo-3,4-dihydro-2H-1,4-benzoxazin-2-yl)methyl]tetrahydro-1(2H)-pyridinecarboximidamide;

3-[(4-5-[(2R,6S)-2,6-dimethyltetrahydro-1(2H)-pyridinyl]pentyl-3-oxo-3,4-dihydro-2H-1,4-benzoxazin-2-yl)methyl]-1-pyrrolidinecarboximidamide;

5-[(4-5-[(2R,6S)-2,6-Dimethyltetrahydro-1(2H)-pyridinyl]pentyl-3-oxo-3,4-dihydro-2H-1,4-benzoxazin-2-yl)methyl]-2-thiophenecarboximidamide;

5-[(4-5-[(2R,6S)-2,6-Dimethyltetrahydro-1(2H)-pyridinyl]pentyl-3-oxo-3,4-dihydro-2H-1,4-benzoxazin-2-yl)methyl]-2-furancarboximidamide;

2-[(4-5-[(2R,6S)-2,6-Dimethyltetrahydro-1(2H)-pyridinyl]pentyl-3-oxo-3,4-dihydro-2H-1,4-benzoxazin-2-yl)methyl]-1,3-oxazole-5-carboximidamide;

5-[(4-5-[(2R,6S)-2,6-Dimethyltetrahydro-1(2H)-pyridinyl]pentyl-3-oxo-3,4-dihydro-2H-1,4-benzoxazin-2-yl)methyl]-1H-imidazole-2-carboximidamide;

2-[(4-5-[(2R,6S)-2,6-Dimethyltetrahydro-1(2H)-pyridinyl]pentyl-3-oxo-3,4-dihydro-2H-1,4-benzoxazin-2-yl)methyl]-1H-imidazole-5-carboximidamide;

6-[(4-5-[(2R,6S)-2,6-Dimethyltetrahydro-1(2H)-pyridinyl]pentyl-3-oxo-3,4-dihydro-2H-1,4-benzoxazin-2-yl)methyl]-2-pyridinecarboximidamide;

2-[(6-Amino-2-pyridinyl)methyl]-4-5-[(2R,6S)-2,6-dimethyltetrahydro-1(2H)-pyridinyl]pentyl-2H-1,4-benzoxazin-3(4H)-one;

4-[(4-5-[(2R,6S)-2,6-Dimethyltetrahydro-1(2H)-pyridinyl]pentyl-3-oxo-3,4-dihydro-2H-1,4-benzoxazin-2-yl)methyl]-2-pyrimidinecarboximidamide;

2-[(2-Amino-4-pyrimidinyl)methyl]-4-5-[(2R,6S)-2,6-dimethyltetrahydro-1(2H)-pyridinyl]pentyl-2H-1,4-benzoxazin-3(4H)-one;

2-[(4-5-[(2R,6S)-2,6-Dimethyltetrahydro-1(2H)-pyridinyl]pentyl-3-oxo-3,4-dihydro-2H-1,4-benzoxazin-2-yl)methyl]-4-pyrimidinecarboximidamide;

2-[(4-Amino-2-pyrimidinyl)methyl]-4-5-[(2R,6S)-2,6-dimethyltetrahydro-1(2H)-pyridinyl]pentyl-2H-1,4-benzoxazin-3(4H)-one;

6-[(4-5-[(2R,6S)-2,6-Dimethyltetrahydro-1(2H)-pyridinyl]pentyl-3-oxo-3,4-dihydro-2H-1,4-benzoxazin-2-yl)methyl]-2-pyrazinecarboximidamide;

2-[(6-Amino-2-pyrazinyl)methyl]-4-5-[(2R,6S)-2,6-dimethyltetrahydro-1(2H)-pyridinyl]pentyl-2H-1,4-benzoxazin-3(4H)-one;

2-(3-Aminocyclohexyl)-4-5-[(2R,6S)-2,6-dimethyltetrahydro-1(2H)-pyridinyl]pentyl-2H-1,4-benzoxazin-3(4H)-one;

3-(4-5-[(2R,6S)-2,6-Dimethyltetrahydro-1(2H)-pyridinyl]pentyl-3-oxo-3,4-dihydro-2H-1,4-benzoxazin-2-yl)cyclohexanecarboximidamide;

2-[(3-Aminocyclohexyl)methyl]-4-5-[(2R,6S)-2,6-dimethyltetrahydro-1(2H)-pyridinyl]pentyl-2H-1,4-benzoxazin-3(4H)-one;

3-[(4-5-[(2R,6S)-2,6-Dimethyltetrahydro-1(2H)-pyridinyl]pentyl-3-oxo-3,4-dihydro-2H-1,4-benzoxazin-2-yl)methyl]cyclohexanecarboximidamide;

2-(3-Aminocyclopentyl)-4-5-[(2R,6S)-2,6-dimethyltetrahydro-1(2H)-pyridinyl]pentyl-2H-1,4-benzoxazin-3(4H)-one;

3-(4-5-[(2R,6S)-2,6-Dimethyltetrahydro-1(2H)-pyridinyl]pentyl-3-oxo-3,4-dihydro-2H-1,4-benzoxazin-2-yl)cyclopentanecarboximidamide;

2-[(3-Aminocyclopentyl)methyl]-4-5-[(2R,6S)-2,6-dimethyltetrahydro-1(2H)-pyridinyl]pentyl-2H-1,4-benzoxazin-3(4H)-one;

3-[(4-5-[(2R,6S)-2,6-Dimethyltetrahydro-1(2H)-pyridinyl]pentyl-3-oxo-3,4-dihydro-2H-1,4-benzoxazin-2-yl)methyl]cyclopentanecarboximidamide;

3-(4-4-[(2R,6S)-2,6-Dimethyltetrahydro-1(2h)-pyridinyl]butyl-3-oxo-3,4-dihydro-2H-1,4-benzoxazin-2-yl)benzenecarboximidamide;

3-(4-6-[(2R,6S)-2,6-Dimethyltetrahydro-1(2H)-pyridinyl]hexyl-3-oxo-3,4-dihydro-2H-1,4-benzoxazin-2-yl)benzenecarboximidamide;

2-(2-3-[Amino(imino)methyl]phenyl-3-oxo-2,3-dihydro-4H-1,4-benzoxazin-4-yl)-N-2-[(2R,6S)-2,6-dimethyltetrahydro-1(2H)-pyridinyl]ethylacetamide;

3-(2-3-[Amino(imino)methyl]phenyl-3-oxo-2,3-dihydro-4H-1,4-benzoxazin-4-yl)-N-[(2R,6S)-2,6-dimethyltetrahydro-1(2H)-pyridinyl]methylpropanamide;

3-4-[2-(2-[(2R,6S)-2,6-Dimethyltetrahydro-1(2H)-pyridinyl]ethylamino)ethyl]-3-oxo-3,4-dihydro-2H-1,4-benzoxazin-2-ylbenzenecarboximidamide;

3-[4-(2-2-[(2R,6S)-2,6-Dimethyltetrahydro-1(2H)-pyridinyl]ethoxyethyl)-3-oxo-3,4-dihydro-2H-1,4-benzoxazin-2-yl]benzenecarboximidamide;

3-(4-4-[(2R,6S)-2,6-Dimethyltetrahydro-1(2H)-pyridinyl]phenyl-3-oxo-3,4-dihydro-2H-1,4-benzoxazin-2-yl)benzenecarboximidamide;

3-(4-4-[(2R,6S)-2,6-Dimethyltetrahydro-1(2H)-pyridinyl]benzyl-3-oxo-3,4-dihydro-2H-1,4-benzoxazin-2-yl)benzenecarboximidamide;

3-[4-(4-[(2R,6S)-2,6-Dimethyltetrahydro-1(2H)-pyridinyl]methylphenyl)-3-oxo-3,4-dihydro-2H-1,4-benzoxazin-2-yl]benzenecarboximidamide;

3-(4-4-[(2R,6S)-2,6-Dimethyltetrahydro-1(2H)-pyridinyl]cyclohexyl-3-oxo-3,4-dihydro-2H-1,4-benzoxazin-2-yl)benzenecarboximidamide;

3-[4-(4-[(2R,6S)-2,6-Dimethyltetrahydro-1(2H)-pyridinyl]cyclohexylmethyl)-3-oxo-3,4-dihydro-2H-1,4-benzoxazin-2-yl]benzenecarboximidamide;

3-[4-(4-[(2R,6S)-2,6-Dimethyltetrahydro-1(2H)-pyridinyl]methylcyclohexyl)-3-oxo-3,4-dihydro-2H-1,4-benzoxazin-2-yl]benzenecarboximidamide;

3-(4-3-[(2R,6S)-2,6-Dimethyltetrahydro-1(2H)-pyridinyl]cyclopentyl-3-oxo-3,4-dihydro-2H-1,4-benzoxazin-2-yl)benzenecarboximidamide;

3-[4-(3-[(2R,6S)-2,6-Dimethyltetrahydro-1(2H)-pyridinyl]cyclopentylmethyl)-3-oxo-3,4-dihydro-2H-1,4-benzoxazin-2-yl]benzenecarboximidamide;

3-[4-(3-[(2R,6S)-2,6-Dimethvltetrahydro-1(2H)-pyridinyl]methylcyclopentyl)-3-oxo-3,4-dihydro-2H-1,4-benzoxazin-2-yl]benzenecarboximidamide;

3-(4-(E)-5-[(2R,6S)-2,6-Dimethyltetrahydro-1(2H)-pyridinyl]-2-pentenyl-3-oxo-3,4-dihydro-2H-1,4-benzoxazin-2-yl)benzenecarboximidamide;

3-[3-Oxo-4-(5-piperidinopentyl)-3,4-dihydro-2H-1,4-benzoxazin-2-yl]benzenecarboximidamide;

3-3-Oxo-4-[5-(2,2,6,6-tetramethylpiperidino)pentyl]-3,4-dihydro-2H-1,4-benzoxazin-2-ylbenzenecarboximidamide;

1-[5-(2-3-[Amino(imino)methyl]phenyl-3-oxo-2,3-dihydro4H-1,4-benzoxazin-4-yl)pentyl]-2-piperidinecarboxylic acid;

1-[5-(2-3-[Amino(imino)methyl]phenyl-3-oxo-2,3-dihydro-4H-1,4-benzoxazin-4-yl)pentyl]-3-piperidinecarboxylic acid;

1-[5-(2-3-[Amino(imino)methyl]phenyl-3-oxo-2,3-dihydro-4H-1,4-benzoxazin-4-yl)pentyl]-4-piperidinecarboxylic acid;

3-4-[5-(3,5-Dimethylpiperidino)pentyl]-3-oxo-3,4-dihydro-2H-1,4-benzoxazin-2-ylbenzenecarboximidamide;

3-4-[5-(4-Hydroxypiperidino)pentyl]-3-oxo-3,4-dihydro-2H-1,4-benzoxazin-2-ylbenzenecarboximidamide;

3-4-[5-(2-Iminopiperidino)pentyl]-3-oxo-3,4-dihydro-2H-1,4-benzoxazin-2-ylbenzenecarboximidamide;

3-3-Oxo-4-[5-(4-oxopiperidino)pentyl]-3,4-dihydro-2H-1,4-benzoxazin-2-ylbenzenecarboximidamide;

3-[4-(5-2-[(Dimethylamino)methyl]piperidinopentyl)-3-oxo-3,4-dihydro-2H-1,4-benzoxazin-2-yl]benzenecarboximidamide;

3-(4-5-[4-(Dimethylamino)piperidino]pentyl-3-oxo-3,4-dihydro-2H-1,4-benzoxazin-2-yl)benzenecarboximidamide;

1-[5-(2-3-[Amino(imino)methyl]phenyl-3-oxo-2,3-dihydro-4H-1,4-benzoxazin-4-yl)pentyl]-4-piperidinesulfonic acid;

3-3-Oxo-4-[5-(2-phenylpiperidino)pentyl]-3,4-dihydro-2H-1,4-benzoxazin-2-ylbenzenecarboximidamide;

3-4-[5-(2,5-Dimethyl-1-pyrrolidinyl)pentyl]-3-oxo-3,4-dihydro-2H-1,4-benzoxazin-2-ylbenzenecarboximidamide;

3-3-Oxo-4-[5-(1-pyrrolidinyl)pentyl]-3,4-dihydro-2H-1,4-benzoxazin-2-ylbenzenecarboximidamide;

1-[5-(2-3-[Amino(imino)methyl]phenyl-3-oxo-2,3-dihydro-4H-1,4-benzoxazin-4-yl)pentyl]-2-pyrrolidinecarboxylic acid;

N-1-[5-(2-3-[Amino(imino)methyl]phenyl-3-oxo-2,3-dihydro-4H-1,4-benzoxazin-4-yl)pentyl]tetrahydro-1H-pyrrol-3-yl-N-methylacetamide;

3-4-[5-(3-Amino-1-pyrrolidinyl)pentyl]-3-oxo-3,4-dihydro-2H-1,4-benzoxazin-2-ylbenzenecarboximidamide;

3-(4-5-[2,5-Bis(methoxymethyl)-1-pyrrolidinyl]pentyl-3-oxo-3,4-dihydro-2H-1,4-benzoxazin-2-yl)benzenecarboximidamide;

3-(4-5-[2-(Hydroxymethyl)-1-pyrrolidinyl]pentyl-3-oxo-3,4-dihydro-2H-1,4-benzoxazin-2-yl)benzenecarboximidamide;

3-(4-5-[2-(Hydroxymethyl)-5-methyl-1-pyrrolidinyl]pentyl-3-oxo-3,4-dihydro-2H-1,4-benzoxazin-2-yl)benzenecarboximidamide;

3-4-[5-(Diisopropylamino)pentyl]-3-oxo-3,4-dihydro-2H-1,4-benzoxazin-2-ylbenzenecarboximidamide;

3-4-[5-(Diethylamino)pentyl]-3-oxo-3,4-dihydro-2H-1,4-benzoxazin-2-ylbenzenecarboximidamide;

3-4-[5-(Methylamino)pentyl]-3-oxo-3,4-dihydro-2H-1,4-benzoxazin-2-ylbenzenecarboximidamide;

3-4-[5-(1-Methyl-1H-imidazol-2-yl)pentyl]-3-oxo-3,4-dihydro-2H-1,4-benzoxazin-2-ylbenzenecarboximidamide;

3-4-[5-(2,5-Dimethyl-1H-imidazol-1-yl)pentyl]-3-oxo-3,4-dihydro-2H-1,4-benzoxazin-2-ylbenzenecarboximidamide;

3-[4-(5-Morpholinopentyl)-3-oxo-3,4-dihydro-2H-1,4-benzoxazin-2-yl]benzenecarboximidamide;

3-4-[5-(3,5-Dimethylmorpholino)pentyl]-3-oxo-3,4-dihydro-2H-1,4-benzoxazin-2-ylbenzenecarboximidamide;

3-[3-Oxo-4-(5-piperazinopentyl)-3,4-dihydro-2H-1,4-benzoxazin-2-yl]benzenecarboximidamide;

3-4-[5-(2,6-Dimethylpiperazino)pentyl]-3-oxo-3,4-dihydro-2H-1,4-benzoxazin-2-ylbenzenecarboximidamide;

3-3-Oxo-4-[5-(1H-pyrazol-1-yl)pentyl]-3,4-dihydro-2H-1,4-benzoxazin-2-ylbenzenecarboximidamide;

3-[3-Oxo-4-(5-tetrahydro-1H-pyrazol-1-ylpentyl)-3,4-dihydro-2H-1,4-benzoxazin-2-yl]benzenecarboximidamide;

3-4-[5-(2,5-Dimethyltetrahydro-1H-pyrazol-1-yl)pentyl]-3-oxo-3,4-dihydro-2H-1,4-benzoxazin-2-ylbenzenecarboximidamide;

3-(6-Chloro-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(4-5-[(2R,6S)-2,6-Dimethyltetrahydro-1(2H)-pyridinyl]pentyl-6-fluoro-3-oxo-3,4-dihydro-2H-1,4-benzoxazin-2-yl)benzenecarboximidamide;

3-(4-5-[(2R,6S)-2,6-Dimethyltetrahydro-1(2H)-pyridinyl]pentyl-3-oxo-6-sulfanyl-3,4-dihydro-2H-1,4-benzoxazin-2-yl)benzenecarboximidamide;

3-[4-5-[(2R,6S)-26-Dimethyltetrahydro-1(2H)-pyridinyl]pentyl-6-(methylsulfanyl)-3-oxo-3,4-dihydro-2H-1,4-benzoxazin-2-yl]benzenecarboximidarmide;

3-[4-5-[(2R,6S)-2,6-Dimethyltetrahydro-1(2H)-pyridinyl]pentyl-3-oxo-6-(trifluoromethyl)-3,4-dihydro-2H-1,4-benzoxazin-2-yl]benzenecarboximidamide;

3-(4-5-[(2R,6S)-2,6-Dimethyltetrahydro-1(2H)-pyridinyl]pentyl-6-methyl-3-oxo-3,4-dihydro-2H-1,4-benzoxazin-2-yl)benzenecarboximidamide;

2-3-[Amino(imino)methyl]phenyl-4-5-[(2R,6S)-2.6-dimethyltetrahydro-1(2H)-pyridinyl]pentyl-3-oxo-3,4-dihydro-2H-1,4-benzoxazine-6-carboxylic acid;

Methyl 2-3-[amino(imino)methyl]phenyl-4-5-[(2R,6S)-2,6-dimethyltetrahydro-1(2H)-pyridinyl]pentyl-3-oxo-3,4-dihydro-2H-1,4-benzoxazine-6-carboxylate;

3-(6-Cyano-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

2-3-[Amino(imino)methyl]phenyl4-5-[(2R,6S)-2,6-dimethyltetrahydro-1(2H)-pyridinyl]pentyl-3-oxo-3,4-dihydro-2H-1,4-benzoxazine-6-carboximidamide;

2-3-[Amino(imino)methyl]phenyl-4-5-[(2R,6S)-2,6-dimethyltetrahydro-1(2H)-pyridinyl]pentyl-N-hydroxy-3-oxo-3,4-dihydro-2H-1,4-benzoxazine-6-carboximidamide;

3-4-5-[(2R,6S)-2,6-Dimethyltetrahydro-1(2H)-pyridinyl]pentyl-6-[hydrazino(imino)methyl]-3-oxo-3,4-dihydro-2H-1,4-benzoxazin-2-ylbenzenecarboximidamide;

2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazine-6-carboxamide;

3-[4-5-[(2R,6S)-2,6-Dimethyltetrahydro-1(2H)-pyridinyl]pentyl-6-(hydroxymethyl)-3-oxo-3,4-dihydro-2H-1,4-benzoxazin-2-yl]benzenecarboximidamide;

3-(6-(Aminomethyl)-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(4-5-[(2R,6S)-2,6-Dimethyltetrahydro-1(2H)-pyridinyl]pentyl-6-nitro-3-oxo-3,4-dihydro-2H-1,4-benzoxazin-2-yl)benzenecarboximidamide;

3-(4-5-[(2R,6S)-2,6-Dimethyltetrahydro-1(2h)-pyridinyl]pentyl-6-hydroxy-3-oxo-3,4-dihydro-2H-1,4-benzoxazin-2-yl)benzenecarboximidamide;

3-(4-5-[(2R,6S)-2,6-Dimethyltetrahydro-1(2H)-pyridinyl]pentyl-6-methoxy-3-oxo-3,4-dihydro-2H-1,4-benzoxazin-2-yl)benzenecarboximidamide;

3-(6-(Benzyloxy)-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

2-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)oxy]acetic acid 3-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)oxy]propanoic acid;

4-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)oxy]butanoic acid;

2-[(2-3-[Amino(imino)methyl]phenyl4-5-[(2R,6S)-2,6-dimethyltetrahydro-1(2H)-pyridinyl]pentyl-3-oxo-3,4-dihydro-2H-1,4-benzoxazin-6-yl)amino]acetic acid;

3-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)amino]propanoic acid;

4-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)amino]butanoic acid;

3-[4-5-[(2R,6S)-2,6-Dimethyltetrahydro-1(2H)-pyridinyl]pentyl-6-(2-hydroxyethoxy)-3-oxo-3,4-dihydro-2H-1,4-benzoxazin-2-yl]benzenecarboximidamide;

3-[4-5-[(2R,6S)-2,6-Dimethyltetrahydro-1(2H)-pyridinyl]pentyl-3-oxo-6-(2H-1,2,3,4-tetraazol-5-ylmethoxy)-3,4-dihydro-2H-1,4-benzoxazin-2-yl]benzenecarboximidamide;

3-(6-Amino4-5-[(2R,6S)-2.6-dimethyltetrahydro-1(2H)-pyridinyl]pentyl-3-oxo-3,4-dihydro-2H-1,4-benzoxazin-2-yl)benzenecarboximidamide;

3-(6-(Butylamino)-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(6-(Dimethylamino)-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(6-Anilino-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(6-(Benzylamino)-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)acetamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)cyclohexanecarboxamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)-2-cyclohexylacetamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)benzenecarboxamide;

N-(2-3-[Amino(imino)methyl]phenyl4-5-[(2R,6S)-2,6-dimethyltetrahydro-1(2H)-pyridinyl]pentyl-3-oxo-3,4-dihydro-2H-1,4-benzoxazin-6-yl)-2-phenylacetamide;

3-4-5-[(2R,6S)-2,6-Dimethyltetrahydro-1(2H)-pyridinyl]pentyl-6-[(methylsulfonyl)amino]-3-oxo-3,4-dihydro-2H-1,4-benzoxazin-2-ylbenzenecarboximidamide;

3-(6-[(Cyclohexylsulfonyl)amino]-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(6-[(Cyclohexylmethyl)sulfonyl]amino-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-4-5-[(2R,6S)-2,6-Dimethyltetrahydro-1(2H)-pyridinyl]pentyl-3-oxo-6-[(phenyisulfonyl)amino]-3,4-dihydro-2H-1,4-benzoxazin-2-ylbenzenecarboximidamide;

3-(6-[(Benzylsulfonyl)amino]-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

2H-1,4-Benzoxazin-3(4H)-one, 4-[3-(2,6-dimethyl-1-piperidinyl)propyl]-2-phenyl-;

4-[5-(2,5-Dimethyl-pyrrolidin-1-yl)-pentyl]-2-phenyl-4H-benzo[1,4]oxazin-3-one;

2H-1,4-Benzoxazin-3(4H)-one, 4-[5-[bis(1-methylethyl)amino]pentyl]-2-phenyl-;

2H-1,4-Benzoxazin-3(4H)-one, 4-[3-(2,5-dimethyl-1-pyrrolidinyl)propyl]-2-phenyl-;

2H-1,4-Benzoxazin-3(4H)-one, 4-[3-[bis(1-methylethyl)amino]propyl]-2-phenyl-;

4-[5-(2,6-Dimethyl -piperidin-1-yl)-pentyl]-2-phenyl-4H-benzo[1,4]oxazin-3-one; 4-(5-Diethylamino-pentyl)-2-phenyl-4H-benzo[1,4]oxazin-3-one;

2-Phenyl-4-(5-pyrrolidin-1-yl-pentyl)-4H-benzo[1,4]oxazin-3-one;

2-[5-(3-Oxo-2-phenyl-2,3-dihydro-benzo[1,4]oxazin-4-yl)-pentyl]-isoindole-1,3-dione;

4-(5-Imidazol-1-yl-pentyl)-2-phenyl-4H-benzo[1,4]oxazin-3-one;

2-(4-Chloro-phenyl)-4-[5-(2,6-dimethyl-piperidin-1-yl)-pentyl]-4H-benzo[1,4]oxazin-3-one;

2-(2-Chloro-phenyl)-4-[5-(2,5-dimethyl-pyrrolidin-1-yl)-pentyl]-4H-benzo[1,4]oxazin-3-one;

2-(2-Chloro-phenyl)-4-[5-(2,6-dimethyl-piperidin-1-yl)-pentyl]-4H-benzo[1,4]oxazin-3-one;

5-(3-Oxo-2-phenyl-2,3-dihydro-benzo[1,4]oxazin-4-yl)-pentanamidine;

2-Phenyl-4-(5-piperidin-1-yl-pentyl)-4H-benzo[1,4]oxazin-3-one;

2-(4-Chloro-phenyl)-4-[5-(2,5-dimethyl-pyrrolidin-1-yl)-pentyl]-4H-benzo[1,4]oxazin-3-one;

2-Phenyl4-(5-pyrrolidin-1-yl-pentyl)-4H-benzo[1,4]oxazin-3-one; compound with trifluoro-acetic acid;

3-(3-Oxo-2-phenyl-2,3-dihydro-benzo[1,4]oxazin-4-ylmethyl)-benzonitrile;

4-[6-(2,5-Dimethyl-pyrrolidin-1-yl)-hexyl]-2-phenyl-4H-benzo[1,4]oxazin-3-one;

3-(3-Oxo-2-phenyl-2,3-dihydro-benzo[1,4]oxazin-4-ylmethyl)-benzamidine;

2-Naphthalen-2-yl-4-(5-piperidin-1-yl-pentyl)-4H-benzo[1,4]oxazin-3-one;

4-(5-Amino-pentyl)-2-phenyl-4H-benzo[1,4]oxazin-3-one;

4-[5-(2,6-Dimethyl-piperidin-1-yl)-pentyl]-2-phenyl-4H-benzo[1,4]oxazin-3-one;

6-Methyl-2-phenyl-4-(5-piperidin-1-yl-pentyl)-4H-benzo[1,4]oxazin-3-one;

7-Methoxy-2-phenyl-4-(5-piperidin-1-yl-pentyl)-4H-benzo[1,4]oxazin-3-one;

8-Chloro-2-phenyl-4-(5-piperidin-1-yl-pentyl)-4H-benzo[1,4]oxazin-3-one;

3-Oxo-2-phenyl-4-(5-piperidin-1-yl-pentyl)-3,4-dihydro-2H-benzo[1,4]oxazine-6-carbonitrile;

4-(3-Oxo-2-phenyl-2,3-dihydro-benzo[1,4]oxazin-4-ylmethyl)-benzamidine;

1-[5-(3-Oxo-2-phenyl-2,3-dihydro-benzo[1,4]oxazin-4-yl)-pentyl]-piperidine-2,6-dione;

3-(3-Oxo-2-phenyl-2,3-dihydro-benzo[1,4]oxazin-4-yl)-propionitrile;

4-(3-Oxo-2-phenyl-2,3-dihydro-benzo[1,4]oxazin-4-yl)-butyronitrile;

5-(3-Oxo-2-phenyl-2,3-dihydro-benzo[1,4]oxazin-4-yl)-pentanenitrile;

N-[3-(3-Oxo-2-phenyl-2,3-dihydro-benzo[1,4]oxazin-4-yl)-propyl]-guanidine;

N-[5-(3-Oxo-2-phenyl-2,3-dihydro-benzo[1,4]oxazin-4-yl)-pentyl]-guanidine;

4-(3-Oxo-2-phenyl-2,3-dihydro-benzo[1,4]oxazin-4-ylmethyl)-benzamidine;

2-(4-Methoxy-phenyl)-4-(5-piperidin-1-yl-pentyl)-4H-benzo[1,4]oxazin-3-one;

7-Methyl-2-phenyl-4-(5-piperidin-1-yl-pentyl)-4H-benzo[1,4]oxazin-3-one;

5-Methyl-2-phenyl-4-(5-piperidin-1-yl-pentyl)-4H-benzo[1,4]oxazin-3-one;

6-Methoxy-2-phenyl-4-(5-piperidin-1-yl-pentyl)-4H-benzo[1,4]oxazin-3-one;

N-Hydroxy-4-(3-oxo-2-phenyl-2,3-dihydro-benzo[1,4]oxazin-4-ylmethyl)-benzamidine;

6-Chloro-2-phenyl-4-(5-piperidin-1-yl-pentyl)-4H-benzo[1,4]oxazin-3-one;

2-(4-Methoxy-phenyl)-4-(5-piperazin-1-yl-pentyl)-4H-benzo[1,4]oxazin-3-one;

2-(4-Hydroxy-phenyl)-4-(5-piperidin-1-yl-pentyl)-4H-benzo[1,4]oxazin-3-one;

4-[5-(2,6-Dimethyl-piperidin-1-yl)-pentyl]-2-(4-hydroxy-phenyl)-4H-benzo[1,4]oxazin-3-one;

2-(4-Methoxy-phenyl)-4-[5-(4-methyl-piperazin-1-yl)-pentyl]-4H-benzo[1,4]oxazin-3-one;

4-{4-[5-(2,6-Dimethyl-piperidin-1-yl)-pentyl]-3-oxo-3,4-dihydro-2H-benzo[1,4]oxazin-2-yl}-benzonitrile;

4-{4-[5-(2,6-Dimethyl-piperidin-1-yl)-pentyl]-3-oxo-3,4-dihydro-2H-benzo[1,4]oxazin-2-yl}-benzamidine;

4-{4-[5-(2,6-Dimethyl-piperidin-1-yl)-pentyl]-3-oxo-3,4-dihydro-2H-benzo[1,4]oxazin-2-yl}-thiobenzamide;

[2-(4-Methoxy-phenyl)-3-oxo-2,3-dihydro-benzo[1,4]oxazin-4-yl]-acetic acid;

4-{4-[5-(2,6-Dimethyl-piperidin-1-yl)-pentyl]-3-oxo-3,4-dihydro-2H-benzo[1,4]oxazin-2-yl}-N-hydroxy-benzamidine;

Benzenecarboximidic acid, 4-[3,4-dihydro-4-[5-(2,6-dimethyl-1-piperidinyl)pentyl]-3-oxo-2H-1,4-benzoxazin-2-yl]-, hydrazide;

6-Amino-2-phenyl-4-(5-piperidin-1-yl-pentyl)-4H-benzo[1,4]oxazin-3-one;

4-(5-Bromo-pentyl)-2-(3,4-dimethoxy-phenyl)-4H-benzo[1,4]oxazin-3-one;

4-(5-Bromo-pentyl)-2-(3,4,5-trimethoxy-phenyl)-4H-benzo[1,4]oxazin-3-one;

4-(5-Bromo-pentyl)-2-(4-methoxy-phenyl)-4H-benzo[1,4]oxazin-3-one;

N-[2-(2,6-Dimethyl-piperidin-1-yl)-ethyl]-2-[2-(4-methoxy-phenyl)-3-oxo-2,3-dihydro-benzo[1,4]oxazin-4-yl]-acetamide;

4-[5-(2,6-Dimethyl-piperidin-1-yl)-pentyl]-2-(3,4,5-trimethoxy-phenyl)-4H-benzo[1,4]oxazin-3-one;

2-(3,4-Dimethoxy-phenyl)-4-[5-(2,6-dimethyl-piperidin-1-yl)-pentyl]-4H-benzo[1,4]oxazin-3-one;

2-(4-Bromo-phenyl)-4-[5-(2,6-dimethyl-piperidin-1-yl)-pentyl]-4H-benzo[1,4]oxazin-3-one;

8-Methyl-2-phenyl-4-(5-piperidin-1-yl-pentyl)-4H-benzo[1,4]oxazin-3-one;

2-(4-Benzylamino-phenyl)-4-[5-(2,6-dimethyl-piperidin-1-yl)-pentyl]4H-benzo[1,4]oxazin-3-one;

2-(4-Methoxy-phenyl)-4-[5-(2,2,6,6-tetramethyl-piperidin-1-yl)-pentyl]-4H-benzo[1,4]oxazin-3-one;

4-(2-Bromo-ethyl)-2-(4-methoxy-phenyl)-4H-benzo[1,4]oxazin-3-one;

4-(5-Bromo-pentyl)-2-(3,4-dichloro-phenyl)-4H-benzo[1,4]oxazin-3-one;

4-(2-Hydroxy-ethyl)-2-(4-methoxy-phenyl)-4H-benzo[1,4]oxazin-3-one;

2-(3,4-Dichloro-phenyl)-4-[5-(2,6-dimethyl-piperidin-1-yl)-pentyl]-4H-benzo[1,4]oxazin-3-one;

4-[3-(2,6-Dimethyl-piperidin-1-ylmethyl)-benzyl]-2-(4-methoxy-phenyl)-4H-benzo[1,4]oxazin-3-one;

4-(2-Amino-ethyl)-2-(4-methoxy-phenyl)4H-benzo[1,4]oxazin-3-one;

2-(2,6-Dimethyl-piperidin-1-yl)-N-{2-[2-(4-methoxy-phenyl)-3-oxo-2,3-dihydro-benzo[1,4]oxazin-4-yl]-ethyl}-acetamide;

4-[5-(2,6-Dimethyl-piperidin-1-yl)-5-oxo-pentyl]-2-(4-methoxy-phenyl)-4H-benzo[1,4]oxazin-3-one;

3-{4-[4-(2,6-Dimethyl-piperidin-1-yl)-butyl]-3-oxo-3,4-dihydro-2H-benzo[1,4]oxazin-2-yl}-benzamidine;

3-{4-[6-(2,6-Dimethyl-piperidin-1-yl)-hexyl]-3-oxo-3,4-dihydro-2H-benzo[1,4]oxazin-2-yl}-benzamidine;

2-(5-Aminomethyl-2-hydroxy-phenyl)-4-[5-(2,6-dimethyl-piperidin-1-yl)-pentyl]-4H-benzo[1,4]oxazin-3-one;

2-(3-Aminomethyl-phenyl)-4-[5-(2,6-dimethyl-piperidin-1-yl)-pentyl]4H-benzo[1,4]oxazin-3-one;

3-{4-[5-(2,6-Dimethyl-piperidin-1-yl)-pentyl]-7-methyl-3-oxo-3,4-dihydro-2H-benzo[1,4]oxazin-2-yl}-benzamidine;

3-{4-[5-(2,6-Dimethyl-piperidin-1-yl)-pentyl]-3-oxo-3,4-dihydro-2H-benzo[1,4]oxazin-2-yl}-4-methoxy-benzamidine;

2-(5-Aminomethyl-2-methoxy-phenyl)-4-[5-(2,6-dimethyl-piperidin-1-yl)-pentyl]-4H-benzo[1,4]oxazin-3-one;

3-{4-[5-(2,6-Dimethyl-piperidin-1-yl)-pentyl]-3-oxo-3,4-dihydro-2H-benzo[1,4]oxazin-2-yl}-N-hydroxy-4-methoxy-benzamidine;

3-{4-[5-(2,6-Dimethyl-piperidin-1-yl)-pentyl]-3-oxo-3,4-dihydro-2H-benzo[1,4]oxazin-2-yl}-N-hydroxy-benzamidine;

3-{7-Chloro-4-[5-(2,6-dimethyl-piperidin-1-yl)-pentyl]-3-oxo-3,4-dihydro-2H-benzo[1,4]oxazin-2-yl}-benzamidine;

4-(5-Bromo-pentyl)-2-phenyl-4H-benzo[1,4]oxazin-3-one;

3-[3-Oxo-4-(5-piperidin-1-yl-pentyl)-3,4-dihydro-2H-benzo[1,4]oxazin-2-yl]-benzamidine;

N-{2-(3-Carbamimidoyl-phenyl)-4-[5-(2,6-dimethyl-piperidin-1-yl)-pentyl]-3-oxo-3,4-dihydro-2H-benzo[1,4]oxazin-6-yl}-acetamide;

3-{4-[5-(2,6-Dimethyl-piperidin-1-yl)-pentyl]-2-methyl-3-oxo-3,4-dihydro-2H-benzo[1,4]oxazin-2-yl}-4-hydroxy-benzamidine;

3-[4-(5-Diisopropylamino-pentyl)-3-oxo-3,4-dihydro-2H-benzo[1,4]oxazin-2-yl]-benzamidine;

3-(4-{4-[(Diisopropylamino)-methyl]-benzyl}-3-oxo-3,4-dihydro-2H-benzo[1,4]oxazin-2-yl)-benzamidine;

3-{4-[4-(2,6-Dimethyl-piperidin-1-ylmethyl)-benzyl]-3-oxo-3,4-dihydro-2H-benzo[1,4]oxazin-2-yl}-benzamidine;

3-{4-[5-(2,6-Dimethyl-piperidin-1-yl)-pentyl]-3-oxo-3,4-dihydro-2H-benzo[1,4]oxazin-2-yl}-4-hydroxy-benzamidine;

3-{4-[5-(2,6-Dimethyl-piperidin-1-yl)-pentyl)-3-oxo-3,4-dihydro-2H-benzo[1,4]oxazin-2-yl}-N-methyl-benzamidine;

{2-(3-Carbamimidoyl-phenyl)-4-[5-(2,6-dimethyl-piperidin-1-yl)-pentyl]-3-oxo-3,4-dihydro-2H-benzo[1,4]oxazin-6-yl}-acetic acid;

3-(4-{3-[(Diisopropylamino)-methyl]-benzyl}-3-oxo-3,4-dihydro-2H-benzo[1,4]oxazin-2-yl)-benzamidine;

3-{4-[3-(2,6-Dimethyl-piperidin-1-ylmethyl)-benzyl]-3-oxo-3,4-dihydro-2H-benzo[1,4]oxazin-2-yl}-benzamidine;

2-(3-Carbamimidoyl-phenyl)-4-[5-(2,6-dimethyl-piperidin-1-yl)-pentyl]-3-oxo-3,4-dihydro-2H-benzo[1,4]oxazine-7-carboxylic acid;

3-{-Oxo-4-[4-(pyridin-2-ylmino)-butyl]-3,4-dihydro-benzo[1,4]oxazin-2-yl}-benzamidine;

2-(3-Carbamimidoyl-phenyl)-4-(5-(2,6-dimethyl-piperidin-1-yl)-pentyl]-3-oxo-3,4-dihydro-2H-benzo[1,4]oxazine-7-carboxylic acid methyl ester;

3-[4-(5-Dihexylamino-pentyl)-3-oxo-3,4-dihydro-2H-benzo[1,4]oxazin-2-yl]-benzamidine;

3-{4-[4-(Methyl-pyridin-2-yl-amino)-butyl]-3-oxo-3,4-dihydro-2H-benzo[1,4]oxazin-2-yl}-benzamidine;

4-[5-(2,6-Dimethyl-piperidin-1-yl)-pentyl]-2-[3-(imino-morpholin-4-yl-methyl)-phenyl]-4H-benzo[1,4]oxazin-3-one;

3-{3-Oxo-4-[4-(pyrimidin-2-ylamino)-butyl]-3,4-dihydro-2H-benzo[1,4]oxazin-2-yl}-benzamidine;

3-[4-(4-Cyclohexylamino-butyl)-3-oxo-3,4-dihydro-2H-benzo[1,4]oxazin-2-yl]-benzamidine;

3-{4-[5-(2,5-Dimethyl-pyrrolidin-1-yl)-pentyl]-3-oxo-3,4-dihydro-2H-benzo[1,4]oxazin-2-yl}-benzamidine;

3-[4-(5-Morpholin-4-yl-pentyl)-3-oxo-3,4-dihydro-2H-benzo[1,4]oxazin-2-yl]-benzamidine;

3-{4-[5-(2,6-Dimethyl-piperidin-1-yl)-2,3-dihydroxy-pentyl]-3-oxo-3,4-dihydro-2H-benzo[1,4]oxazin-2-yl}-benzamidine;

4-[2-(3-Carbamimidoyl-phenyl)-3-oxo-2,3-dihydro-benzo[1,4]oxazin-4-ylmethyl]-N,N-dimethyl-benzamide;

2-(3-Carbamimidoyl-phenyl)4-[5-(2,6-dimethyl-piperidin-1-y)-pentyl]-3-oxo-3,4-dihydro-2H-benzo[1,4]oxazine-6-carboxylic acid;

3-[2-(3-Carbamimidoyl-phenyl)-3-oxo-2,3-dihydro-benzo[1,4]oxazin-4-ylmethyl]-N,N-dimethyl-benzamide;

3-{4-[5-(2,6-Dimethyl-piperidin-1-yl)-pent-2-enyl]-3-oxo-3,4-dihydro-2H-benzo[1,4]oxazin-2-yl}-benzamidine;

3-[4-(5-Amino-pentyl)-3-oxo-3,4-dihydro-2H-benzo[1,4]oxazin-2-yl]-benzamidine;

2-(3-Carbamimidoyl-phenyl)-4-[5-(2,6-dimethyl-piperidin-1-yl)-pentyl]-3-oxo-3,4-dihydro-2H-benzo[1,4]oxazine-6-carboxylic acid methyl ester;

4-Methoxy-3-[4-(4-methoxy-benzyl)-3-oxo-3,4-dihydro-2H-benzo[1,4]oxazin-2-yl]-benzonitrile;

3-{4-[5-(2,6-Dimethyl-piperidin-1-yl)-pent-3-enyl]-3-oxo-3,4-dihydro-2H-benzo[1,4]oxazin-2-yl}-benzamidine;

4-[2-(3-Cyano-phenyl)-3-oxo-2,3-dihydro-benzo[1,4]oxazin-4-ylmethyl]-N,N-dimethyl-benzamide;

3-[2-(3-Carbamimidoyl-phenyl)-3-oxo-2,3-dihydro-benzo[1,4]oxazin-4-ylmethyl]-5-(2,6-dimethyl-piperidin-1-ylmethyl)-benzoic acid;

3-{4-[5-(2,6-Dimethyl-piperidin-1-yl)-pentyl]-3-oxo-3,4-dihydro-2H-benzo[1,4]oxazin-2-yl}-4-hydroxy-benzamidine;

3-Acetyl-2-(2-methoxy-phenyl)-thiazolidine4-carboxylic acid 4-cyano-2-{4-[5-(2,6-dimethyl-piperidin-1-yl)-pentyl]-3-oxo-3,4-dihydro-2H-benzo[1,4]oxazin-2-yl}-phenyl ester;

3-[2-(3-Carbamimidoyl-phenyl)-3-oxo-2,3-dihydro-benzo[1,4]oxazin-4-ylmethyl]-5-(2,6-dimethyl-piperidin-1-ylmethyl)-N-hydroxy-benzamide;

4-(2-Dimethylamino-ethyl)-7-nitro-2-phenyl-4H-benzo[1,4]thiazin-3-one;

4-(2-Diethylamino-ethyl)-7-nitro-2-phenyl-4H-benzo[1,4]thiazin-3-one;

2H-1,4-Benzothiazin-3(4H)-one, 4-[2-(dimethylamino)ethyl]-7-nitro-2-phenyl-, monohydrochloride;

2H-1,4-Benzothiazin-3(4H)-one, 4-[2-(diethylamino)ethyl]-7-nitro-2-phenyl-, monohydrochloride;

4-[5-(2,6-Dimethyl-piperidin-1-yl)-pentyl]-2-(4-methoxy-phenyl)-4H-benzo[1,4]thiazin-3-one;

4-{4-[5-(2,6-Dimethyl-piperidin-1-yl)-pentyl]-3-oxo-3,4-dihydro-2H-benzo[1,4]thiazin-2-yl}-benzonitrile;

4-{4-[5-(2,6-Dimethyl-piperidin-1-yl)-pentyl]-3-oxo-3,4-dihydro-2H-benzo[1,4]thiazin-2-yl}-thiobenzamide;
4-[5-(2,6-Dimethyl-piperidin-1-yl)-pentyl)-2-(4-methoxy-phenyl)-4H-benzo[1,4]thiazin-3-one; compound with trifluoro-acetic acid;
3-{4-[5-(2,6-Dimethyl-piperidin-1-yl)-pentyl]-3-oxo-3,4-dihydro-2H-benzo[1,4]thiazin-2-yl}-benzonitrile;
3-{4-[5-(2,6-Dimethyl-piperidin-l-yl)-pentyl]-3-oxo-3,4-dihydro-2H-benzo[1,4]thiazin-2-yl}-benzamide;
4-[5-(2,6-Dimethyl-piperidin-1-yl)-pentyl]-2-(3-methoxy-phenyl)-2-(4-methoxy-phenyl)-4H-benzo[1,4]thiazin-3-one;
4-[5-(2,6-Dimethyl-piperidin-1-yl)-pentyl]-2-(4-methoxy-phenyl)-1,1-dioxo-1,4-dihydro-2H-11>6-benzo[1,4]thiazin-3-one;
2-(4-Benzyloxy-phenyl)-4-[5-(2,6-dimethyl-piperidin-1-yl)-pentyl]4H-benzo[1,4]thiazin-3-one;
2-(4-Butoxy-phenyl)-4-[5-(2,6-dimethyl-piperidin-1-yl)-pentyl]-4H-benzo[1,4]thiazin-3-one;
3-{4-[5-(2,6-Dimethyl-piperidin-1-yl)-pentyl]-3-oxo-3,4-dihydro-2H-benzo[1,4]thiazin-2-yl}-thiobenzamide;
4-{4-[5-(2,6-Dimethyl-piperidin-1-yl)-pentyl]-3-oxo-3,4-dihydro-2H-benzo[1,4]thiazin-2-yl}-benzamidine;
3-{4-(5-(2,6-Dimethyl-piperidin-1-yl)-pentyl]-3-oxo-3,4-dihydro-2H-benzo[1,4]thiazin-2-yl}-N-hydroxy-benzamidine;
3-{4-[5-(2,6-Dimethyl-piperidin-1-yl)-pentyl]-3-oxo-3,4-dihydro-2H-benzo[1,4]thiazin-2-yl}-benzamidine;
3-{4-[5-(2-Hydroxymethyl-pyrrolidin-1-yl)-pentyl]-3-oxo-3,4-dihydro-2H-benzo[1,4]thiazin-2-yl}-benzamidine;
4-Allyl-2,2-diphenyl-4H-benzo[1,4]thiazin-3-one;
4-(2-Diethylamino-ethyl)-7-nitro-2-phenyl-4H-benzo[1,4]thiazin-3-one;
2-(3-Diethylamino-propylamino)-4-methyl-2-phenyl-4H-benzo[1,4]thiazin-3-one;
4-(2-Diethylamino-ethyl)-2,2-diphenyl-4H-benzo[1,4]thiazin-3-one;
2-Benzyl-4-(5-piperidin-1-yl-pentyl)-4H-benzo[1,4]oxazin-3-one;
2-Cyclohexyl-4-[5-(2,6-dimethyl-piperidin-1-yl)-pentyl]-4H-benzo[1,4]thiazin-3-one;
2H-1,4-Benzothiazin-3(4H)-one, 4-methyl-2,2-diphenyl-;
4-Ethyl-2-phenyl-2-piperidin-1-yl-4H-benzo[1,4]thiazin-3-one;
4-Methyl-2-phenyl-2-piperidin-1-yl-4H-benzo[1,4]thiazin-3-one;
3-{4-[5-(2,6-dimethyl-piperidin-1-yl)-pentyl]-3-oxo-3,4-dihydro-2H-benzo[1,4]oxazin-2-yl}-piperidine-1-carboxamidine;
4-[5-(2,6-Dimethyl-piperidin-1-yl)-pentyl]-2-piperidin-3-yl-4H-benzo[1,4]oxazin-3-one;
3-Oxo-2-phenyl-2,4-bis-(5-piperidin-1-yl-pentyl)-3,4-dihydro-2H-benzo[1,4]oxazine-6-carbonitrile;
4-[5-(2,6-Dimethyl-piperidin-1-yl)-pentyl]-2-pyridin-2-yl-4H-benzo[1,4]oxazin-3-one;
N-Hydroxy-3-oxo-2-phenyl-4-(5-piperidin-1-yl-pentyl)-3,4-dihydro-2H-benzo[1,4]oxazine-6-carboxamidine;
3-Oxo-2-phenyl-4-(5-piperidin-1-yl-pentyl)-3,4-dihydro-2H-benzo[1,4]oxazine-6-carboxamidine;
3-{4-[5-(2,6-Dimethyl-piperidin-1-yl)-pentyl]-3-oxo-3,4-dihydro-2H-benzo[1,4]oxazin-2-yl}-thiobenzamide;
3-{4-[5-(Adamantan-1-ylamino)-pentyl]-3-oxo-3,4-dihydro-2H-benzo[1,4]oxazin-2-yl}-benzamidine;
2-(3-Diethylamino-propylamino)-4-methyl-2-phenyl-4H-benzo[1,4]oxazin-3-one;
4-[3-(2,6-Dimethyl-1-piperidinyl)propyl]-2-phenyl-2H/-1,4-benzoxazin-3(4H/)-one; and
4-Methyl-2-phenyl-2H/-1,4-benzoxazin-3(4H/)-one.

DETAILED DESCRIPTION OF THE INVENTION

The term "alkyl" means a straight, branched, saturated or unsaturated carbon chain having from 1 to 20 carbon atoms. Typical alkyl groups include methyl, isobutyl, pentyl, 2-methyl-pentyl, pent-1,4-dienyl, but-1-enyl and the like.

The term "cycloalkyl" means a saturated or unsaturated carbon chain which forms a ring having from 3 to 20 carbon atoms. Typical examples include cyclopropyl, cyclohexyl and the like.

The term "cycloalkylalkyl" means a cycloalkyl group attached to an alkyl group wherein "cycloalkyl" and "alkyl" are as defined above and includes, for example, cyclopropylmethyl, cyclopentylethyl and the like.

The term "heteroalkyl" means a straight, branched, saturated or unsaturated carbon chain having from 1 to 20 carbon atoms wherein one or more carbon atoms is replaced by a heteroatom selected from oxygen, nitrogen, sulfur, sulphoxide or sulphone. Typical "heteroalkyl" groups include methoxymethyl, 3-thiomethylpropyl, and 2-thiomethoxyethoxymethyl and the like.

The term "aryl" represents an unsaturated carbocyclic ring(s) of 6 to 16 carbon atoms which is optionally substituted with, OH, O(alkyl), SH, S(alkyl), amine, halogen, acid, ester, amide, alkyl ketone, aldehyde, nitrile, fluoroalkyl, amidine, nitro, sulphone. sulfoxide or $(C_{1-6})$alkyl, thioamide, Oalkylaryl, benzylamino, C(NH)(NHNH$_2$), N-hydroxyamidine, N-methylamidine. Typical rings include phenyl, naphthyl, phenanthryl, and anthracenyl. Preferred aryl rings are phenyl, substituted phenyl, and naphthyl.

The term "arylalkyl" means an aromatic radical attached to an alkyl radical wherein "aryl" and "alkyl" are as defined above and includes, for example, benzyl, and naphthylmethyl.

The term "heterocycle" means a saturated or unsaturated mono- or polycyclic (i.e. bicyclic) ring incorporating one or more (i.e. 1–4) heteroatoms selected from N, O, and S. It is understood that a heterocycle is optionally substituted with OH, O(alkyl), SH, S(alkyl), amine, halogen, acid, ester, amide, amidine alkyl ketone, aldehyde, nitrile, fluoroalkyl, nitro, sulphone, sulfoxide or $C_{1-6}$ alkyl. Examples of suitable monocyclic heterocycles include, but are not limited to substituted or unsubstituted thienyl, furanyl, pyrrolyl, imidazolyl, pyrazolyl, thiazolyl, isothiazolyl, oxazolyl, isoxazolyl, triazolyl, tetrazolyl, pyridinyl, pyrazinyl, pyrimidinyl, piperidinyl, pyrrolidinyl, piperazinyl, azetidinyl, aziridinyl, morpholinyl, thietanyl, oyetanyl. Preferred monoydicheterocycles include, but are not limited to, 2- or 3- thienyl, 2- or 3-furanyl, 1-, 2-, or 3-pyrrolyl, 1-, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 1, 3-, or 5-triazolyl, 1-, 2-, or 3-tetrazolyl, 2, 3-, or 4-pyridinyl, 2-pyrazinyl, 2-, 4-, or 5-pyrimidinyl, 1-, 2-, 3-, or 4- piperidinyl, 1-, 2-, or 3-pyrrolidinyl, 1- or 2-piperazinyl, 1-, 2-, or 3-azetidinyl, 1- or 2-aziridinyl, 2-, 3-, or 4-morpholinyl, 2- or 3- thietanyl, 2- or 3-oxetanyl. Examples of suitable bicyclic heterocycles include, but are not limited to, indolizinyl, isoindolyl, benzothienyl, benzoxazolyl, benzimidazolyl, quinolinyl, isoquinolinyl, and preferably 1-, 2-, 3-, 4-, 5-, 6-, or 7-indolyl, 1-, 2-, 3-, 5-, 6-, 7-, or 8-indolizinyl, 1-, 2-, 3-, 4-, 5-, 6-, or 7-isoindolyl, 2-, 3-, 4-, 5-, 6-, or 7-benzothienyl, 2-, 4-, 5-, 6-, or 7-benzoxazolyl, 1-, 2-, 4-, 5-, 6-, or 7-benzimidazolyl, 2-, 3-, 4-, 5-, 6-* 7-, or 8-quinolinyl, 1-3-, 4-, 5-, 6-, 7-, or 8-isoquinolinyl.

The term "heteroatom" as used herein represents oxygen, nitrogen, or sulfur (O, N, or S) as well as sulfoxyl or sulfonyl (SO or $SO_2$) unless otherwise indicated. It is understood that alkyl chains interrupted by one or more heteroatoms means that a carbon atom of the chain is replaced with a heteroatom having the appropriate valency. Preferably, an alkyl chain is interrupted by 1 to 4 heteroatoms and that two adjacent carbon atoms are not both replaced. Examples of such groups include methoxymethyl, 3-thiomethylpropyl, and 2-thiomethoxyethoxymethyl.

The term "amine" refers to a group such as $NH_2$, NHalkyl, NH(cycloalkyl), NH(cycloalkylalkyl), NH(aryl), NH(arylalkyl), NH(heteroaryl), NH(heteroarylalkyl), N(alkyl)(alkyl), N(alkyl)(cycloalkyl), N(alkyl)(cycloalkylalkyl), N(alkyl)(aryl), N(alkyl)(arylalkyl), N(alkyl)(heteroaryl), N(alkyl)(heteroarylalkyl), N(cycloalkyl)(cycloalkyl), N(cycloalkyl)(cycloalkylalkyl), N(cycloalkyl)(aryl), N(cycloalkyl)(arylalkyl), N(cycloalkyl)(heteroaryl), N(cycloalkyl)(heteroarylalkyl), N(cycloalkylalkyl)(cycloalkylalkyl), N(cycloalkylalkyl)(aryl), N(cycloalkylalkyl)(arylalkyl), N(cycloalkylalkyl)(heteroaryl), N(cycloalkylalkyl)(heteroarylalkyl), N(aryl)(cycloalkylalkyl), N(aryl)(aryl), N(aryl)(arylalkyl), N(aryl)(heteroaryl), N(aryl)(heteroarylalkyl), N(arylalkyl)(arylalkyl),N(arylalkyl)(heteroaryl), N(arylalkyl)(heteroarylalkyl), N(heteroaryl)(heteroaryl), N(heteroaryl)(heteroarylalkyl), N(heteroarylalkyl)(heteroarylalkyl).

The tem "acid" refers to C(=O)OH.

The term "ketone" refers to C(=O)alkyl, C(=O)cycloalkyl, C(=O)cycloalkylalkyl, C(=O)aryl, C(=O)arylalkyl, C(=O)heteroaryl, C(=O)heteroarylalkyl.

The term "ester" refers to a group such as C(=O)Oalkyl, C(=O)Ocycloalkyl, C(=O)Ocycloalkylalkyl, C(=O)Oaryl, C(=O)Oarylalkyl, C(=O)Oheteroaryl, C(=O)Oheteroarylalkyl.

The term "amide" refers to a group such as, C(=O)$NH_2$, C(=O)NHalkyl, C(=O)NH(cycloalkyl), C(=O)NH(cycloalkylalkyl), C(=O)NH(aryl), C(=O)NH(arylalkyl), C(=O)NH(heteroaryl), C(=O)NH(heteroarylalkyl), C(=O)N(alkyl)(alkyl), C(=O)N(alkyl)(cycloalkyl), C(=O)N(alkyl)(cycloalkylalkyl), C(=O)N(alkyl)(aryl), C(=O)N(alkyl)(arylalkyl), C(=O)N(alkyl)(heteroaryl), C(=O)N(alkyl)(heteroarylalkyl), C(=O)N(cycloalkyl)(cycloalkyl), C(=O)N(cycloalkyl)(cycloalkylalkyl), C(=O)N(cycloalkyl)(aryl), C(=O)N(cycloalkyl)(arylalkyl), C(=O)N(cycloalkyl)(heteroaryl), C(=O)N(cycloalkyl)(heteroarylalkyl), C(=O)N(cycloalkylalkyl)(cycloalkylalkyl), C(=O)N(cycloalkylalkyl)(aryl), C(=O)N(cycloalkylalkyl)(arylalkyl), C(=O)N(cycloalkylalkyl)(heteroaryl), C(=O)N(cycloalkylalkyl)(heteroarylalkyl), C(=O)N(aryl)(cycloalkylalkyl), C(=O)N(aryl)(aryl), C(=O)N(aryl)(arylalkyl), C(=O)N(aryl)(heteroaryl), C(=O)N(aryl)(heteroarylalkyl), C(=O)N(arylalkyl)(arylalkyl), C(=O)N(arylalkyl)(heteroaryl), C(=O)N(arylalkyl)(heteroarylalkyl), C(=O)N(heteroaryl)(heteroaryl), C(=O)N(heteroaryl)(heteroarylalkyl), C(=O)N(heteroarylalkyl)(heteroarylalkyl).

The term "urea" refers to a group such as NHC(=O)N(alkyl)(alkyl), NHC(=O)N(alkyl)(cycloalkyl), NHC(=O)N(alkyl)(cycloalkylalkyl), NHC(=O)N(alkyl)(aryl), NHC(=O)N(alkyl)(arylalkyl), NHC(=O)N(alkyl)(heteroaryl), NHC(=O)N(alkyl)(heteroarylalkyl), NHC(=O)N(cycloalkyl)(cycloalkyl), NHC(=O)N(cycloalkyl)(cycloalkylalkyl), NHC(=O)N(cycloalkyl)(aryl), NHC(=O)N(cycloalkyl)(arylalkyl), NHC(=O)N(cycloalkyl)(heteroaryl), NHC(=O)N(cycloalkyl)(heteroarylalkyl), NHC(=O)N(cycloalkylalkyl)(cycloalkylalkyl), NHC(=O)N(cycloalkylalkyl)(aryl), NHC(=O)N(cycloalkylalkyl)(arylalkyl), NHC(=O)N(cycloalkylalkyl)(heteroaryl), NHC(=O)N(cycloalkylalkyl)(heteroarylalkyl), NHC(=O)N(aryl)(cycloalkylalkyl), NHC(=O)N(aryl)(aryl), NHC(=O)N(aryl)(arylalkyl), NHC(=O)N(aryl)(heteroaryl), NHC(=O)N(aryl)(heteroarylalkyl), NHC(=O)N(arylalkyl)(arylalkyl), NHC(=O)N(arylalkyl)(heteroaryl), NHC(=O)N(arylalkyl)(heteroarylalkyl), NHC(=O)N(heteroaryl)(heteroaryl), NHC(=O)N(heteroaryl)(heteroarylalkyl), NHC(=O)N(heteroarylalkyl)(heteroarylalkyl).

The term "halogen" refers to chlorine, fluorine, bromine, and iodine.

The wedge or hash is only one representation of a stereochemical descriptor. All stereoisomers, including enantiomers and diastereomers, are included within Formulas 1–8 and are provided by this invention. When specific isomers are drawn, they are the preferred isomers.

In some situations, compounds may exist as tautomers. All tautomers are included within Formulas 1–8 and are provided by this invention.

When compounds are administered, some metabolism may occur. All metabolites are included within Formulas 1–8 and are provided by this invention.

When a bond to a substituent is shown to cross the bond connecting 2 atoms in a ring, then such substituent may be bonded to any atom in the ring, provided the atom will accept the substituent without violating its valency. When there appears to be several atoms of the substituent that may bond to the ring atom, then it is the first atom of the listed substituent that is attached to the ring.

When a bond is represented by a line such as "---," this is meant to represent that the bond may be absent or present provided that the resultant compound is stable and of satisfactory valency.

Compounds of the present invention are capable of forming acid addition salts (see for example, Berge S. M., et al., "Pharmaceutical Salts," *Journal of Pharmaceutical Science*, 1977:1–10) with inorganic acids such as, for example, hydrochloric acid, sulfuric acid and the like, as well as salts derived from organic acids such as, for example, aliphatic mono and dicarboxylic acids or aliphatic and aromatic sulphonic acids. The acid addition salts are prepared by contacting the free base form with a sufficient amount of the desired acid to produce the salt. The free base form may be regenerated by contacting the salt form with a base. While the free base more may differ from the salt form in terms of physical properties, such as solubility, the salts are equivalent to their respective free bases for the purposes of the present invention.

Certain compounds of the present invention can exist in unsolvated form as well as solvated form including hydrated form. In general, the solvated form including hydrated form is equivalent to unsolvated form and is intended to be encompassed within the scope of the present invention.

"Prodrugs" are intended to include any covalently bonded carrier which releases the active parent drug according to Formulas 1–8 in vivo. Examples of prodrugs include acetates, formates, benzoate derivatives of alcohols and amines present in compounds of Formulas 1–8. They also include derivatives of the amidine or guanine functionality and would include C(=$NR_3$)$NH_2$ where $R_3$ is selected from OH, $NH_2$, $C_{1-4}$ alkoxy, $C_{6-10}$ aryloxy, $C_{1-10}$ alkoxycarbonyl, $C_{6-10}$ aryloxycarbonyl. Preferred derivatives include examples wherein $R_3$ is OH, $NH_2$, methoxy, and ethoxycarbonyl.

The following table provides a list of abbreviations and definitions thereof used in the present invention.

| Abbreviation | Description |
|---|---|
| AMC | aminomethylcoumarin |
| aPTT | activated partial thromboplastin time |
| BOC | tertiary-butyloxycarbonyl |
| BOP-reagent | benzotriazol-1-yloxy-tris(dimethylamino) phosphonium hexafluorophosphate |
| Bz | benzoate |
| $CDCl_3$ | deuterochloroform |
| DMF | dimethyl formamide |
| DMSO | dimethylsulfoxide |
| $^1$H-NMR | proton nuclear magnetic resonance |
| HCl | hydrogen chloride |
| HF | hydrogen fluoride |
| HMPA | hexamethylphosphoramide |
| HPLC | high pressure liquid chromatography |
| MOT | mean occlusion time |
| MS(APCI) | mass spectrometry (atmospheric pressure CI) |
| MS(CI) | mass spectrometry (chemical ionization) |
| MS(ES) | mass spectrometry (electro spray) |
| NaOH | sodium hydroxide |
| nBuLi | n-butyl lithium |
| $NH_4Cl$ | ammonium chloride |
| Pd/C | palladium on carbon |
| $PtO_2$ | platinum oxide |
| r.t. or RT | room temperature |
| TFA | trifluoroacetic acid |
| THF | tetrahydrofuran |
| TT | thrombin time |
| VAZO-52 | 2,2'-Azobis-2-methylvaleronitrile |

Also provided by this invention is a method for preventing and treating acute, subacute, and chronic thrombotic disorder in a mammal comprising administering to such mammal an effective amount of a compound of Formulas 1–8. The compounds are useful as anticoagulants for the treatment and prophylaxis of disorders such as venous and arterial thrombosis, pulmonary embolism. and ischemic events such as myocardial infarction or cerebral infarction. These compounds also have therapeutic utility for the prevention and treatment of complications of indwelling vascular access ports and arteriovenous shunts and coagulopathies associated with cardiopulmonary bypass or other extracorporeal systems. These compounds are useful for preventing or treating unstable angina, refractory angina, intermittent claudication, disseminated intravascular coagulation, and ocular buildup of fibrin. Since thrombin and serine proteases have also been demonstrated to activate a number of different cell types, these compounds are useful for the treatment or prophylaxis of septic shock and other inflammatory responses such as acute or chronic atherosclerosis. The compounds also have utility in treating neoplasia/metastasis and neurodegenerative diseases such as Alzheimer's and Parkinson's disease. In a preferred method, the thrombotic disorder is selected from venous thrombosis, arterial thrombosis, pulmonary embolism, myocardial infarction, cerebral infarction, angina, cancer, diabetes. A further embodiment of this invention is a pharmaceutical formulation comprising a compound of Formulas 1–8 administered with a diluent, excipient, or carrier thereof.

PREPARATION OF COMPOUNDS OF THE INVENTION

The compounds of Formulas 1–8 can be prepared by any of various methods known to those skilled in the art of organic chemistry. The following general schemes represent preferred routes to provide the compounds of this disclosure. The reactions are typically performed in solvents appropriate to the reagents and substrates employed. It is understood that functionality present in the molecule must be compatible with the reagents and reaction conditions proposed. Not all compounds of Formulas 1–8 falling into a given class may be compatible with some of the reaction conditions described. Such restrictions are readily apparent to those skilled in the art of organic synthesis, and alternative methods must then be used.

Scheme 1

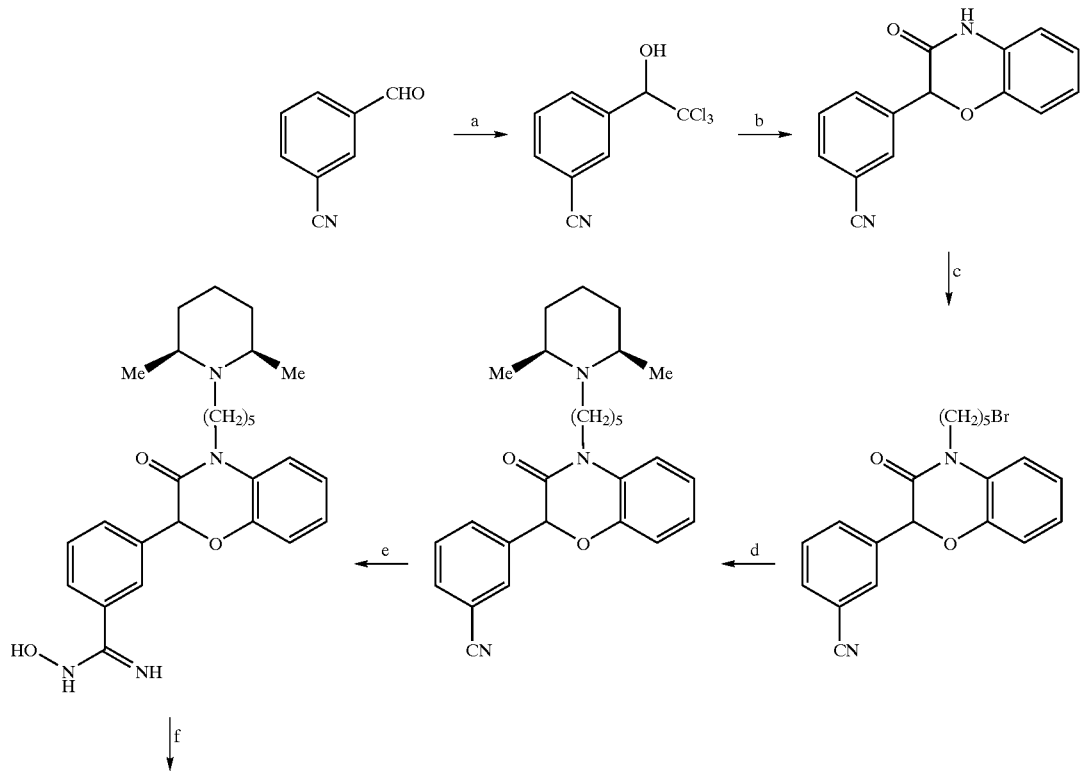

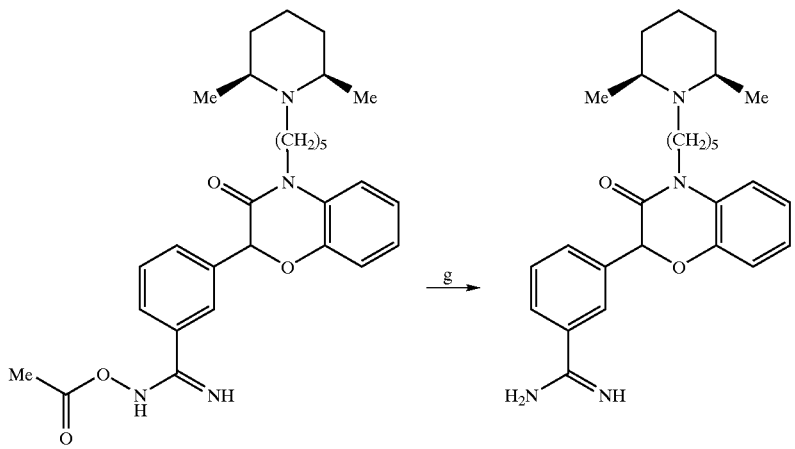

Step a:

The aldehyde is converted to the trichloromethyl carbinol by treatment with carbon tetrachloride and aluminum/lead bromide DMF at room temperature according to the procedure of Tanaka *J., Org. Chem.*, 1989:444. Alternative procedures include the addition of trimethylsilyl trichloromethane and tetrabutylammonium fluoride or more typically chloroform and potassium hydroxide as exemplified by Galun, *Org. Synth. Coll.*, 1973; V:130. It should also be noted that trimethylsilyl trichloroacetate in the presence of potassium fluoride is an effective process for the preparation of trichlormethylcarbinols as exemplified by Weissman, *Org. Proced. Int.*, 1995;27(5):590–592.

Step b:

Addition of o-aminophenol and base affords the benzoxazinone in a manner similar to the procedure of Gukasyan et al., *Arm. Khim. Zh.*, 1988;41(9):572–575. This typically involves treatment of the trichloromethyl carbinol with a suitably substituted ortho-amino phenol in a solvent such as DMF or DMSO in the presence of potassium hydroxide or sodium hydride at room temperature to 100° C. It is apparent that by employing choral trichloromethyl carbinol, the resulting benzoxazinone will be obtained in chiral form.

Step c:

Alkylation is typically achieved by treatment with an appropriate electrophile and by the addition of a base in a dipolar aprotic solvent. Typical conditions include, for example, use of a bis-electrophilic substrate such as 1,5-dibromopentane in a dipolar aprotic solvent such as DMF or DMSO and addition of a base, such as sodium hydride. Alternatively, alkylation can be achieved by the addition of a phase transfer reagent such as an alkylammonium salt, such as benzyltriethylammonium chloride, and employing a base such as sodium ethoxide. Reaction rates are typically improved by the application of heat, and hence, reactions are run at from 0° C. to 70° C.

Step d:

Treatment with an amine, such as cis-2,6-dimethylpiperidine at an elevated temperature such as 50° C. affords the expected N-alkylated piperidine. The amine may be used as solvent, or alternatively, the amine may be added in stoichiometric proportions and the reaction mixture refluxed in a solvent such as ethanol, acetonitrile, or toluene.

The product, as the appropriate acid addition salt, is then neutralized by the addition of base such as aqueous potassium hydroxide. In situations where the amine is volatile, then the reaction mixture is heated, typically from 50° C. to 150° C., in a sealed tube.

Step e:

Conversion of the nitrile to the hydroxyamidine is achieved by allowing the nitrile to react with hydroxylamine in methanol at room temperature. Typically, hydroxylamine hydrochloride is added to the nitrile containing substrate at room temperature, and the reaction is initiated by the addition of base such as potassium carbonate or diisopropylethylamine. The reaction is usually monitored by HPLC to determine the absence of starting material, the nitrile, and are typically complete within a 24-hour period.

Step f:

The amidoxime is activated by the addition of acetic anhydride of trifluoroacetic anhydride intermediate in a solvent such as acetic acid or trifluoroacetic acid to afford the O-acylated intermediate, which may be isolated or alternatively used directly in the subsequent reduction step. This step and the subsequent reduction may be combined, i.e., the reduction with Pd/C is performed in acetic anhydride/acetic acid, or trifluoroacetic anhydride/trifluoroacetic acid.

Step g:

The substrate is dissolved in methanol, or acetic acid, or trifluoroacetic acid, and treated with a transition metal catalyst such as Palladium dispersed on carbon and is then hydrogenated briefly, typically for 1 to 12 hours. The product is then isolated, typically by crystallization or via chromatography such as reverse phase HPLC.

Alternative procedures for the synthesis of the parent benzoxazinone include. for example in scheme 2:

Scheme 2

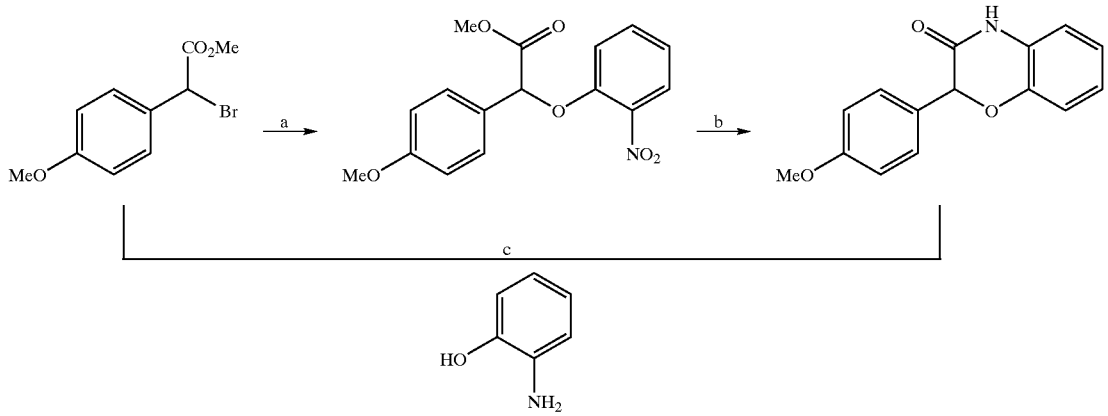

Step a:
Treatment of the methyl alpha-bromo phenylacetate with ortho-nitrophenol and base readily affords the phenolic ether. Of course, it is realized that activation of the benzylic carbon as a chloride or mesylate would also suffice to allow the initial etherification to proceed. Typically, the potassium or sodium salt of ortho-nitrophenol is added to the electrophile in a solvent, such as DMF, and the mixture warmed, typically to 50° C., until the reaction is judged complete by TLC. Use of a chiral alpha-functionalized aryl acetate would afford the chiral adduct.

Step b:
Reduction of the nitro group to the corresponding aniline is readily achieved with a transition metal such as palladium on carbon or Raney nickel and hydrogen or alternatively by treatment with tin in aqueous hydrochloric acid. These anilines readily cyclize to the corresponding benzoxazinone during the reduction or upon warning in a solvent such as methanol.

Step c:
Alternatively upon addition of ortho-aminophenol according to the procedure of *Bull. Soc. Chim. Belg.*, 1987:473–480, the benzoxazine-2-one is isolated directly.

A further alternative procedure for the preparation of the requisite benzoxazinones requires the treatment of the substituted amino phenol with the acid chloride as shown in Scheme 3 in a manner similar to that described by Krapcho, Tawada et al., *Chem. Pharm. Bull.*, 1990:1238–1245.

Scheme 3

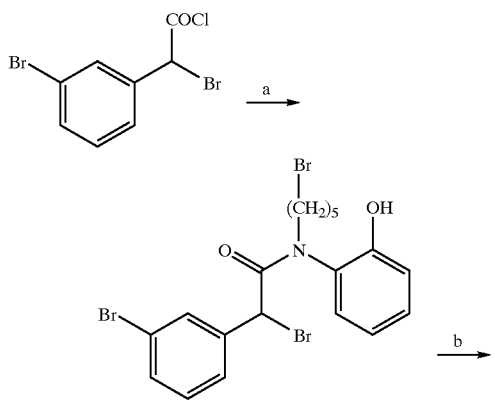

-continued

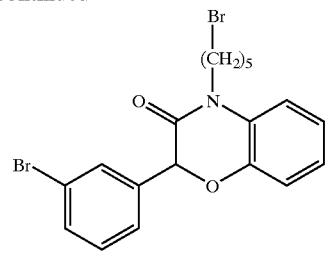

Step a:
The ortho amino phenol is treated with the acid chloride in a solvent such as dichloromethane in the presence of a base such as diisopropylethylamine to afford the N-acylated product.

Step b:
Treatment with a base such as potassium carbonate in a solvent such as DMF then affords the parent benzoxazinone via an intramolecular nucleophilic addition of the phenoxide to the secondary bromide.

A further alternative procedure is outlined in Scheme 4 which is initiated by etherification of an ortho-halo phenol with an alpha-bromo phenylacetamide. Subsequent intramolecular nucleophilic substitution then affords the N-alkylated benzoxazinone (Coutts and Southcott J., *Chem. Soc., Perkin Trans. I*, 1990:767–771).

Scheme 4

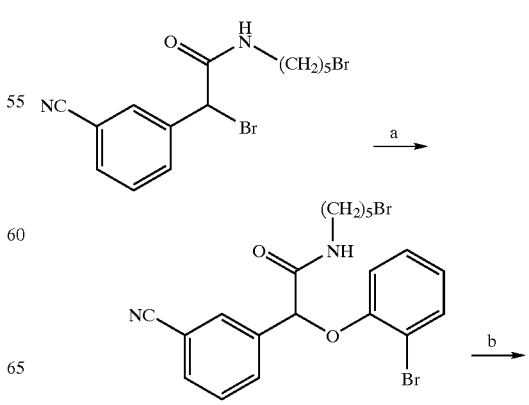

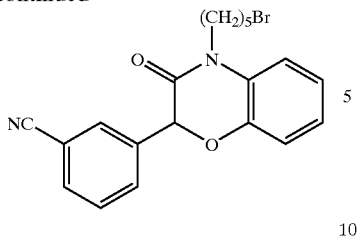
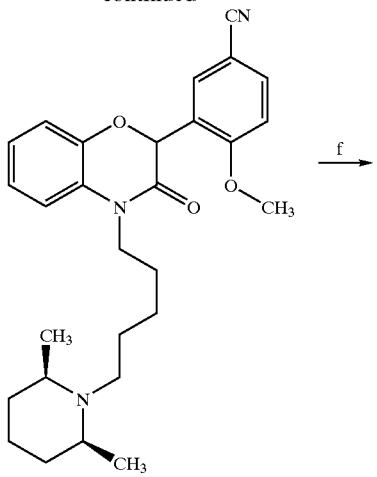

Step a:

The sodium salt of the phenol is treated with the electrophile in a solvent such as methylene chloride or dioxane, and then the reaction mixture is warmed to 100° C. for 4 hours.

Step b:

Addition of sodium hydride in a solvent such as DMPU and warming to 100° C. affords the required benzoxazinone.

Scheme 5 demonstrates another alternative procedure that may be employed.

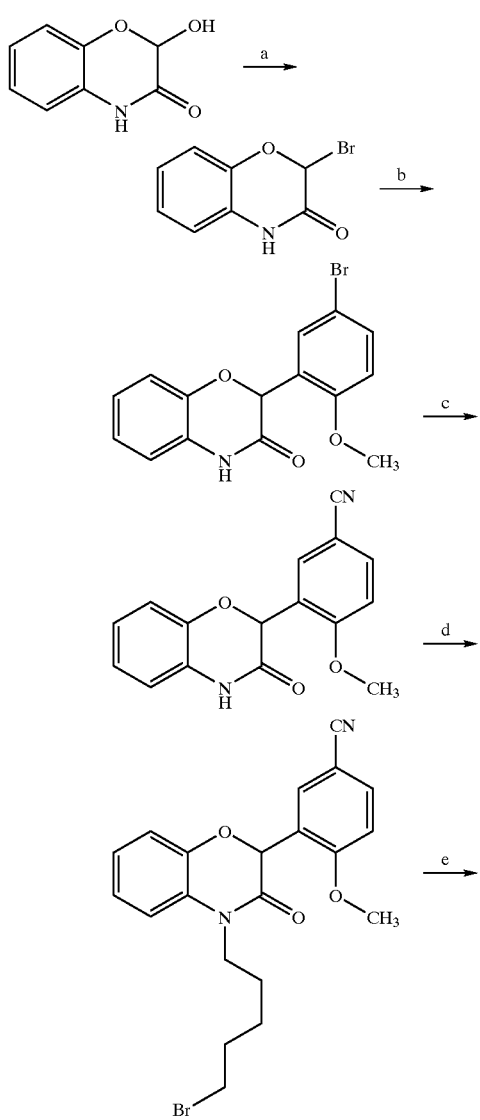

Step a:

2-Hydroxy-2H-1,4-benzoxazin-3(4H)-one is prepared by the procedures of Sahu A. *Indian Journal of Chemistry*, 1990;603–605, or Matlin S A, *JCS Perkin Trans I*, 1979;2481–2487 and is then treated with HBr in acetic acid/acetic anhydride to afford 2-bromo-2H-1,4-benzoxazin-3(4H)-one at room temperature for 24 to 48 hours, according to the procedure of Tietze LF, *Synthesis*, 1991;1118–1120. The product precipitates from the reaction mixture and due to its hydrolytic instability is used directly in the subsequent reaction step. Alternatively the acetate may be prepared by treating the alcohol with acetic anhydride in the presence of pyridine and catalytic DMAP. Addition of HBr in acetic acid to this acetate again affords the corresponding bromide.

Step b:

Addition of a phenol or phenolic ether, such as 4-bromo anisole and a Lewis acid, such as tin (IV) chloride or aluminum (III) chloride. affords after refluxing for several hours the corresponding 2-aryl substituted benzoxazinone.

Steps c–f:

Performed in a manner similar to the previous schemes

The substituted alpha-bromo phenylacetates used in these reactions are prepared by a number of standard procedures such as those shown in Scheme 6.

Scheme 6

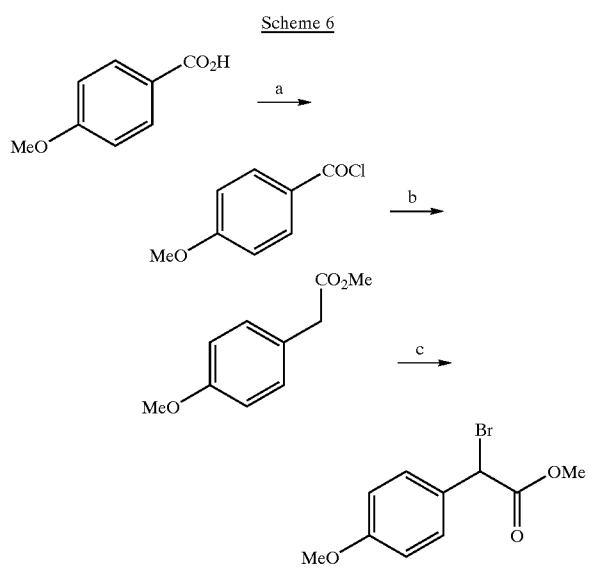

Acetic acid derivatives are prepared by conversion of the substituted benzoic acid to the corresponding acid chloride with. for example, oxalyl chloride and catalytic DMF and is then treated with ethereal diazomethane. Rearrangement with silver oxide in an alcoholic solvent, such as methanol, affords the homologated acetic acid methyl ester. Functionalisation of the alpha position is then achieved by refluxing a solution of the ester in carbon tetrachloride with N-bromosuccinimide in the presence of a radical initiator such as AIBN. It is also readily apparent that treatment of acetic acid derivatives with bromine in the presence of phosphorus tribromide will afford the alpha-bromo phenyl acetate in a manner similar to the named reaction Hell-Volhard-Zelinskii.

Alternatively, the intermediate alpha bromo ester may be prepared by the procedure shown in Scheme 7 according to the procedure of Robert A., Jaguelin S., Guinamant J. L. "Synthesis of esters of α-halo acids from gem dicyano epoxides. *Tetrahedron*, 1986;42(8):2275–2281.

Scheme 7

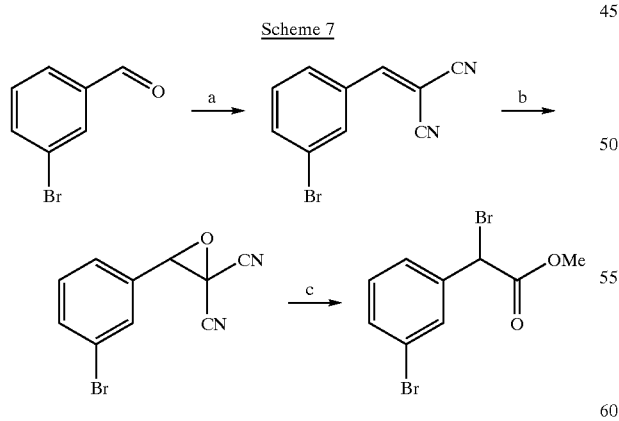

In this situation the aldehyde, such as 3-bromobenzaldehyde as a representative example, is reacted with malononitrile in the presence of catalytic piperidine in a solvent such as dioxane to afford the 2-[(3-bromophenyl)methylene]malononitrile. Epoxide formation proceeds readily with commercial bleach at a pH of 5 to 6. Treatment with hydrobromic acid in methanol then affords the required methyl 2-bromo-2-(3-bromophenyl)acetate. Similarly prepared was methyl 2-bromo-2-(3-cyanophenyl)acetate Alternative procedures for the conversion of nitriles to amidines are also available as shown in Scheme 8. The nitrile in turn are available by, for example, a palladium catalyzed cross-coupling reaction with $Zn(CN)_2$ or via treatment of the aryl bromide at elevated temperatures with copper (I) cyanide. Treatment of the nitrile with hydrogen chloride in an alcoholic solvent affords the corresponding iminoether hydrochloride. These intermediates are then treated with source of ammonia, for example ammonia in methanol, or ammonium chloride, or ammonium acetate, and the mixture is stirred, and warmed if necessary, to afford the amidine.

Scheme 8

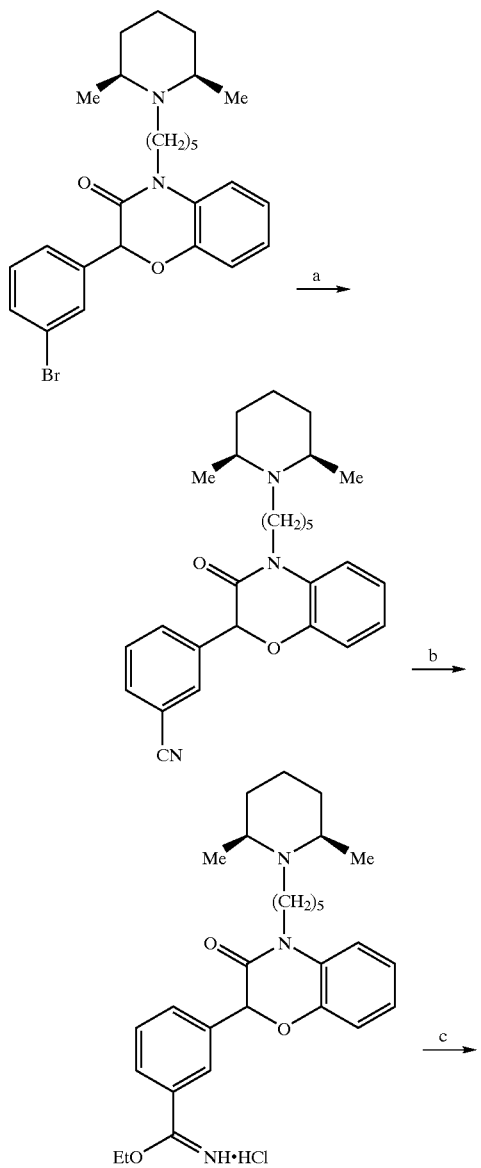

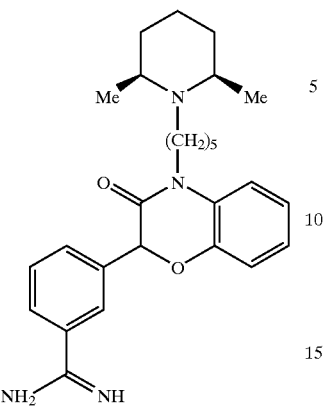

The benzothiazinone of Formula 1 may also be prepared according to Scheme 9.

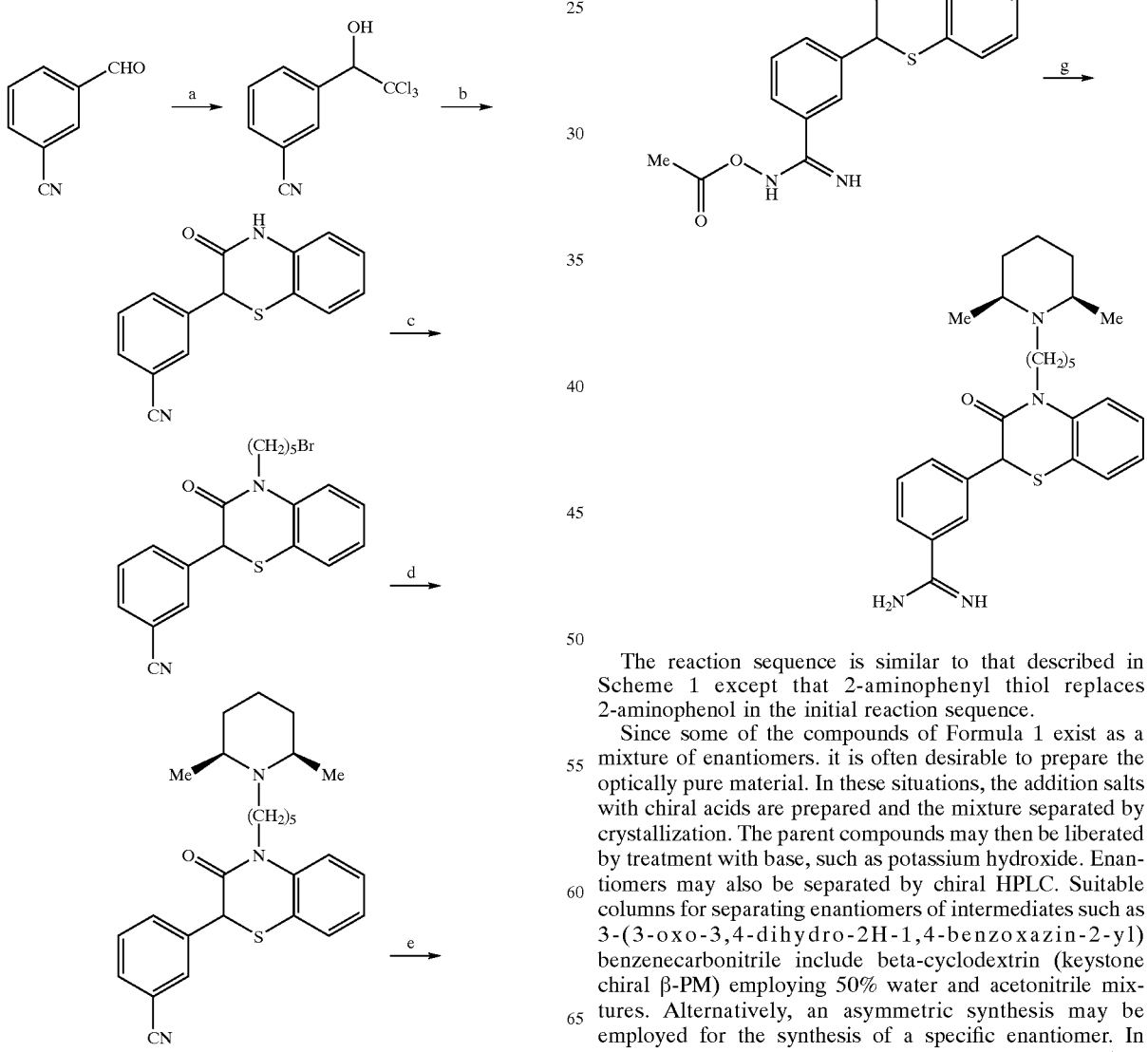

The reaction sequence is similar to that described in Scheme 1 except that 2-aminophenyl thiol replaces 2-aminophenol in the initial reaction sequence.

Since some of the compounds of Formula 1 exist as a mixture of enantiomers. it is often desirable to prepare the optically pure material. In these situations, the addition salts with chiral acids are prepared and the mixture separated by crystallization. The parent compounds may then be liberated by treatment with base, such as potassium hydroxide. Enantiomers may also be separated by chiral HPLC. Suitable columns for separating enantiomers of intermediates such as 3-(3-oxo-3,4-dihydro-2H-1,4-benzoxazin-2-yl)benzenecarbonitrile include beta-cyclodextrin (keystone chiral β-PM) employing 50% water and acetonitrile mixtures. Alternatively, an asymmetric synthesis may be employed for the synthesis of a specific enantiomer. In particular, a suitably substituted phenoxide (for benzoxazinones) or thiophenoxide (for benzothiazinones) may be added to a pentolactone derivative, as described by Koh, *J. Org. Chem.*, 1994;59:4683–4686 and outlined in Scheme 10.

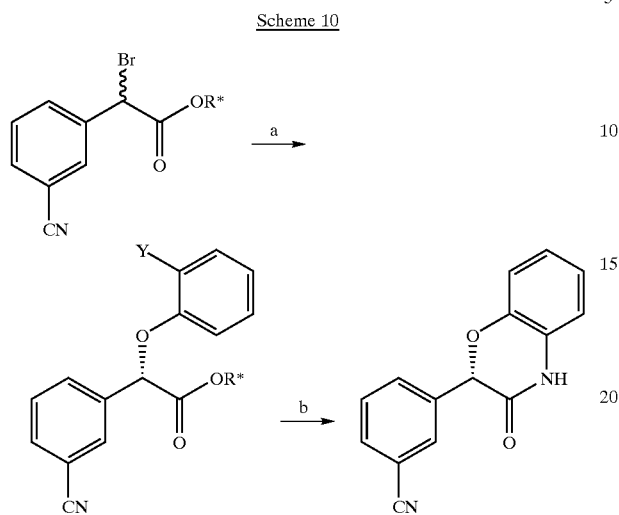

Use of (R) pantolactone esters affords the (S) diastereomer. In this scheme, Y is a substituent that may be elaborated to afford an aniline which undergoes intramolecular cyclization to afford the required chiral benzoxazinone. Examples of such substituents would include a nitro functionality or N-acetyl group.

A further alternative procedure for the generation of chiral benzoxazinone intermediates is available by application of lactamide derived esters of racemic alpha-halo carboxylic acids (Devine, *Tetrahedron Letts.*, 1996:2683–2686) as outlined in Scheme 11.

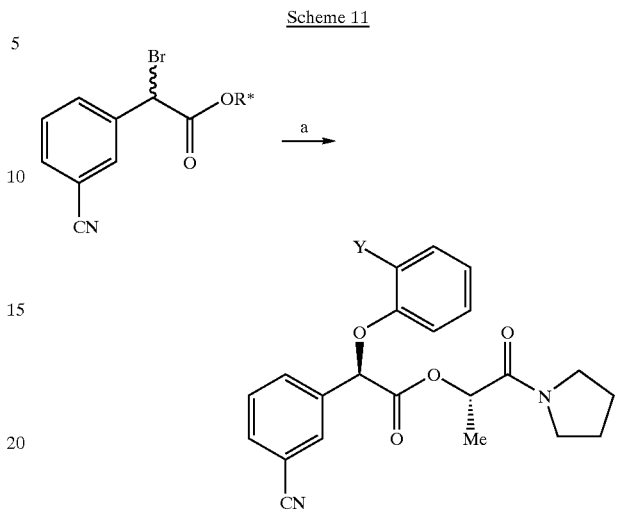

The diastereoselectivity of this reaction is good, and the products are of the (R) stereochemistry providing a complementary approach to that of Scheme 10.

It should be noted that chiral alpha-trichloromethyl carbinols afford optically active alpha-aryloxy acids upon treatment with phenoxide providing yet another alternative method to preparing chiral benzoxazinones or benzothiazinones (Corey, *Tetrahedron Lett.*, 1992:3431).

Another procedure for preparing chiral benzoxazinones is outlined in Scheme 12

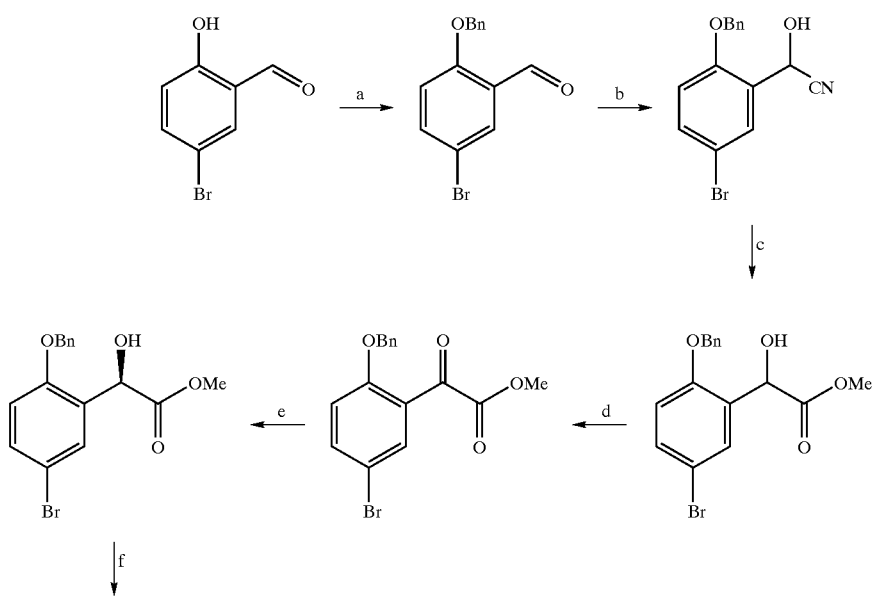

-continued

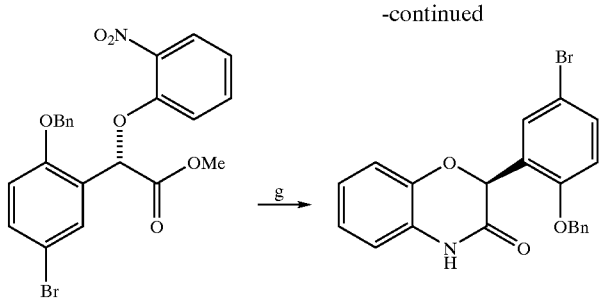

Step a:
The aldehyde is protected via the formation of a suitable protecting group, which in the above scenario is a benzylether, with for example potassium carbonate or sodium hydroxide and benzyl bromide in a solvent such as DMF or ethanol.

Step b:
Addition of cyanide to the aldehyde readily forms the intermediate cyano hydrin in a solvent such as methanol. It is envisioned that this process may also be performed in an assymetric manner by use of any one of the following general procedures Danda, H et al., *Chem Lett* 1991, 731. Poly(quinidine-co-acrylonitrile) Effenberger, F et al., *Tetrahedron Lett* 1990, 31 (9), 1249. (Oxynitrilase) Mori, A. et al., *Chem Lett* 1989(12), 2119. Cyclo-(Leu-His) or Tanaka, K. et al., *J Org Chem* 1990, 55, 181. cyclo((S)-Phe-(S)-His) Minamikawa, H. et al., *Bull Chem Soc Jpn* 1988, 61 (12), 4379. 1,1,4,4-Tetraphenylbutanetetraol-(2R,3R)-O,O-phenylethylidene Ti(i-PrO)2Cl2 Harrington, K. J et al., *Aust J Chem* 1986, 39, 1135.1) beta-Cyclodextrin Steps c:
Conversion of the cyano functional group to a methyl ester is readily achieved by treatment of the nitrile with HCl gas in an alcoholic solvent such as methanol. Addition of water then readily converts the intermediate imino ether to the ester.

Step d:
Oxidation of the alcohol to the keto-ester is readily achieved with an oxidising agent such as oxalyl chloride and dimethylsulfoxide or by heating with manganese dioxide in a solvent such as toluene or methylene chloride.

Step e:
Chiral reduction of the keto-ester is best achieved with a reducing agent like R-alpine borane. This reduction is typically slow and takes several days to complete.

Step f:
A Mitsunobo coupling reaction is then performed on this chiral alcohol employing nitro phenol (or possibly amino phenol), diisopropylazodicarboxalate (or other alkylazodicarboxylate) and triphenylphosphine in a solvent such as ethylacetate at a low temperature such as −40° C.

Step g:
Reduction of the nitro group is best achieved with neutral Raney Nickel and a hydrogen atmosphere in a solvent such as methanol. It is important that the solution does not become basic since a reduction in enantiomeric excess may be observed.

Compounds of the present invention are further characterized by their ability to inhibit the catalytic activity of factor Xa, which is demonstrated in the assay as follows. Compounds of the present invention may be prepared for assay by dissolving them in buffer to give solutions ranging in concentrations from 1 to 100 $\mu$M. In an assay to determine the inhibitory dissociation constant, $K_i$, for a given compound, a chromogenic or fluorogenic substrate of factor Xa would be added to a solution containing a test compound and factor Xa; the resulting catalytic activity of the enzyme is spectrophotometrically determined. This assay is well-known to those skilled in the art and is commonly used to determine antithrombotic activity.

The compounds of the present invention may be used as anti-coagulants in vitro or ex vivo as in the case of contact activation with foreign thrombogenic surfaces such as is found in tubing used in extracorporeal shunts. The compounds of the invention may also be used to coat the surface of such thrombogenic conduits. To this end, the compounds of the invention can be prepared as lyophilized powders, redissolved in isotonic saline or similar diluent, and added in an amount sufficient to maintain blood in an anticoagulated state.

The therapeutic agents of the present invention may be administered alone or in combination with pharmaceutically acceptable carriers. The proportion of each carrier is determined by the solubility and chemical nature of the compound, the route of administration, and standard pharmaceutical practice. For example, the compounds may be injected parenterally; this being intramuscularly, intravenously, or subcutaneously. For parenteral administration, the compound may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may also be administered sublingually in the form of troches or lozenges in which each active ingredient is mixed with sugar or corn syrups, flavoring agents, and dyes, and then dehydrated sufficiently to make the mixture suitable for pressing into solid form. The compounds may be administered orally in the form of solutions which may contain coloring and/or flavoring agents. Typical formulations will contain from about 5% to 95% by weight of an invention compound.

The amount of invention compound to be utilized to prevent and treat thrombotic disorders is that amount which is effective to prevent or treat the condition without causing unacceptable side effects. Such effective amounts will be from about 0.01 mg/Kg to about 500 mg/Kg, preferably from about 1 mg/Kg to about 100 mg/Kg. Physicians will determine the precise dosage of the present therapeutic agents which will be most suitable. Dosages may vary with the mode of administration and the particular compound chosen. In addition, the dosage may vary with the particular patient under treatment.

When the composition is administered orally, a larger quantity of the active agent will typically be required to produce the same effect as caused with a smaller quantity given parenterally.

To further assist in understanding the present invention, the following non-limiting examples of such factor Xa inhibitory compounds are provided. The following examples, of course, should not be construed as specifically limiting the present invention, variations presently known or later developed, which would be within the purview of one skilled in the art and considered to fall within the scope of the present invention as described herein. The preferred compounds as of the present invention are synthesized using conventional preparative steps and recovery methods known to those skilled in the art of organic and bio-organic synthesis, while providing a new and unique combination for the overall synthesis of each compound. Preferred synthetic routes for intermediates involved in the synthesis as well as the resulting anti-thrombotic compounds of the present invention follow.

EXAMPLES

In general, evaporation of reaction mixtures were carried out by rotary evaporation in vacuo at room temperature 18° C. to 25° C. or at elevated temperatures up to 50° C. Chromatography, preferably by medium pressure liquid chromatography, were generally performed on Merck Kieselgel. Reverse phase purification via high pressure liquid chromatography (HPLC), for particular polar compounds, was performed on C-18 reverse phase silica gel employing a gradient elution of water and acetonitrile containing 0.1% trifluoroacetic acid. The final products displayed nuclear magnetic resonance (NMR) spectra and mass spectra consistent with their assigned structure. Intermediates were not typically fully characterized and their purity was routinely assessed by HPLC or thin layer chromatography.

Example 1

4-5-[(2R,6S)-2,6-Dimethylhexahydro-1-pyridinyl] pentyl-2-(4-methoxyphenyl)-3,4-dihydro-2H-1,4-benzoxazin-3-one Step (a): Preparation of Methyl 2-bromo-2-(4-methoxyphenyl)acetate

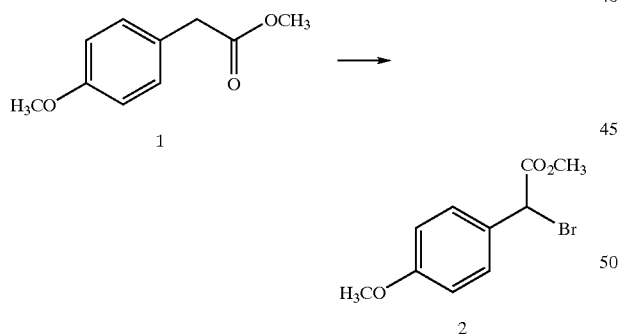

To methyl 4-methoxyphenylacetate (1) (5.0 g, 27.7 mmol) in carbon tetrachloride was added N-bromosuccinimide (5.92 g, 33.3 mmol) and VAZO52 (152 mg, 0.612 mmol). The reaction mixture was stirred and heated at reflux for 3 hours. $^1$H NMR indicated complete bromination of the starting material. The mixture was cooled in an ice-bath. The precipitate was filtered and washed with carbon tetrachloride. The filtrate was evaporated in vacuo to give (2) as a brown oil in quantitative yield, and sufficiently pure for subsequent reactions.

$^1$H NMR (CDCl$_3$, 400 MHz): δ 7.44 (2H, d, J=6.84 Hz), 6.84 (2H, d, J=6.71 Hz), 5.31 (1H, s), 3.77 (3H, s), 3.75 (3H, s).

Step (b): Preparation of Methyl 2-(4-Methoxyphenyl)-2-(2-nitrohenoxy)acetate

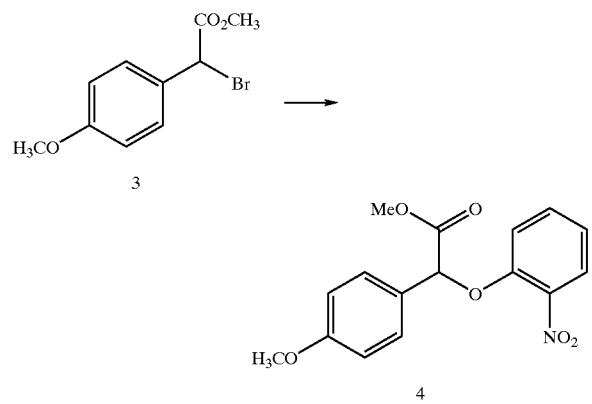

To (3) (7.18 g, 27.7 mmol) in DMSO (20 mL) was added o-nitrophenol sodium salt (7.32 g, 45.5 mmol). The reaction mixture was stirred at 70° C. for 24 hours. The reaction mixture was cooled, diluted with water, and extracted with ethyl acetate (3×300 mL). The combined organic extracts were washed with brine (200 mL), dried with magnesium sulfate, filtered, and evaporated in vacuo. The residue was purified on a silica gel column eluted with 20% ethyl acetate in hexane. The product (4) was isolated 2.90 g (33%) as an orange oily solid.

$^1$H NMR (CDCl$_3$, 300 MHz): δ 7.88 (1H, m), 7.54–7.44 (3H, m), 6.92–7.11 (4H, m), 5.70 (1H, s), 3.82 (3H, s), 3.72 (3H, s).

Step (c): Preparation of 2-(4-Methoxyphenyl)-3,4-dihydro-2H-1,4-benzoxazin-3-one

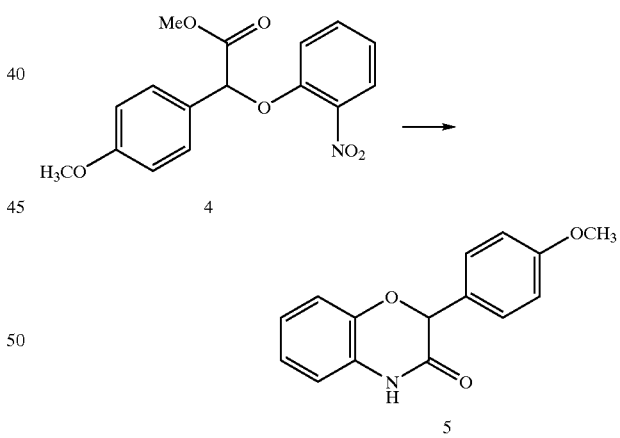

The phenolic ether (4) (2.88 g, 9.08 mmol) was hydrogenated over Raney nickel (1 g) in THF (50 mL) and methanol (50 mL) for 23 hours at room temperature. The mixture was filtered and the filter pad washed with methanol and THF. The combined filtrate and washings were evaporated in vacuo to give the benzoxazinone (5) as an orange solid in quantitative yield.

$^1$H NMR (CDCl$_3$, 300 MHz): δ 7.78 (1H, bs), 7.35 (2H, d, J=8.79 Hz), 7.00–6.76 (6H, m), 5.63 (1H, s), 3.77 (3H, s).

Step (d): Preparation of 4-(5-Bromopentyl)-2-(4-methoxyphenyl)-3,4-dihydro-2H- 1,4-benzoxazin-3-one

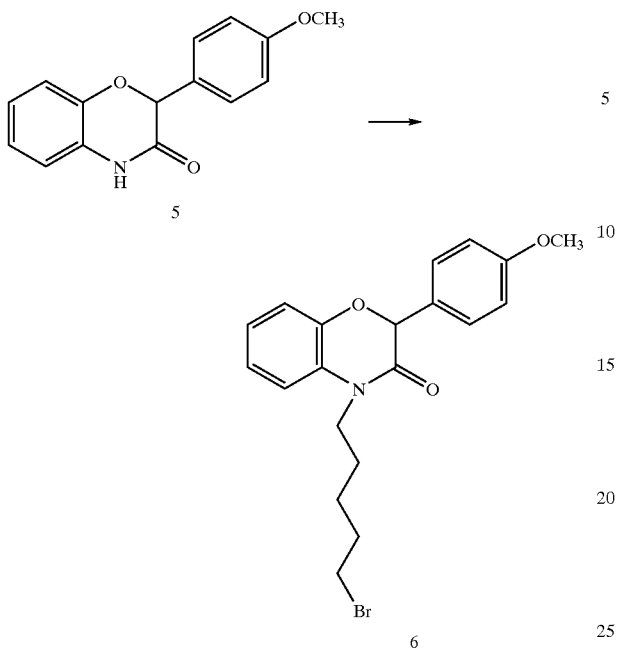

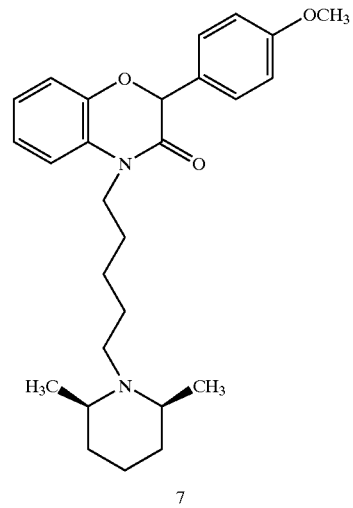

To the benzoxazinone (5) (2.42 g, 9.48 mmol) in DMF (9 mL) was added sodium hydride (0.433 g, 10.82 mmol), and the solution was stirred at 70° C. for 15 minutes until bubbling stopped. To this solution was added 1,5-dibromopentane (8.66 g, 37.7 mmol), and the solution was stirred at 70° C. for additional 5 hours. The solution was cooled, diluted with water, and extracted with ethyl acetate (5×200 mL). The combined organic extracts were washed with brine (2×100 mL), dried with magnesium sulfate, filtered, and evaporated in vacuo. The residue was purified on a silica gel column eluted with 20% ethyl acetate in hexane. The product (6) was isolated 1.85 g (48%) as a yellow oil.

$^1$H NMR (CDCl$_3$, 300 MHz): δ 7.26 (2H, d, J=4.49 Hz), 7.03–6.96 (4H, m), 6.84 (2H, d, J=6.68 Hz), 5.64 (1H, s), 4.12 (2H, m), 3.80 (3H, s), 3.40 (2H, m), 1.96–1.87 (2H, m), 1.75–1.68 (2H, m), 1.61–1.51 (2H, m).

Step (e): Preparation of 4-5-[(2R,6S)-2,6-Dimethylhexahydro-1-pyridinyl]pentyl-2-(4-methoxyphenyl)-3,4-dihydro-2H-1,4-benzoxazin-3-one

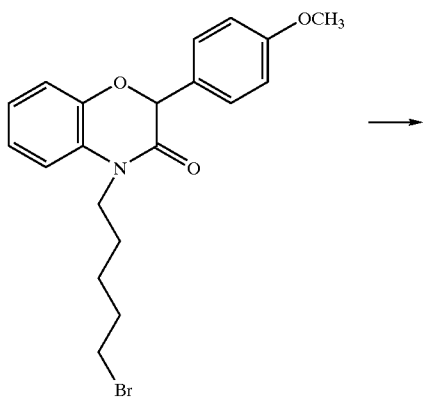

To (6) (0.50 g, 1.23 mmol) was added cis-2,6-dimethylpiperidine (2 mL, 14.8 mmol), and the solution was stirred at 50° C. for 16 hours. The solution was cooled, diluted with water, and extracted with ethyl acetate (3×100 mL). The combined organic extracts were washed with saturated sodium bicarbonate (2×100 mL), washed with brine (2×100 mL), dried with magnesium sulfate, filtered, and evaporated in vacuo. The residue was purified by preparative HPLC (Vydac 218TP 1022 C-18, eluted with a mixture of solvents consisting of (i) 0.1% trifluoroacetic acid in water. and (ii) 0.1% trifluoroacetic acid in acetonitrile, gradient profile 95:5 (i):(ii) to 60:40 (i):(ii) over 90 minutes, flow rate 20 mL/minute, λ=214 nM) and was lyophilized to give 27 mg (12%) of product (7) as a fluffy white solid.

$^1$ H NMR (CDCl$_3$, 400 MHz): δ 7.27 (2H, m), 7.03–6.95 (4H, m), 6.84 (2H, m), 5.63 (1H, s), 4.03 (2H, m), 3.77 (3H, s), 3.25 (2H, m), 3.00 (2H, s), 2.72 (2H, m), 2.41 (2H, bs), 2.04 (2H, m), 1.88–1.66 (6H, m), 1.48–1.32 (6H, m). CI MS M+1=437. HPLC: RT=17.28 min. (Beckman 235328 C-18 5 μm 4.6 mm×25 cm. eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes. flow rate 1.5 mL/minute, λ=214 nM).

Example 2

3-(4-5-[(2R,6S)-2,6-Dimethylhexahydro-1-pyridinyl]pentyl-3-oxo-3,4-dihydro-2H-1,4-benzoxazin-2-yl)-1-benzenecarboximidamide Step (a): Preparation of 3-(2,2,2-Trichloro-1-hydroxyethyl)benzonitrile

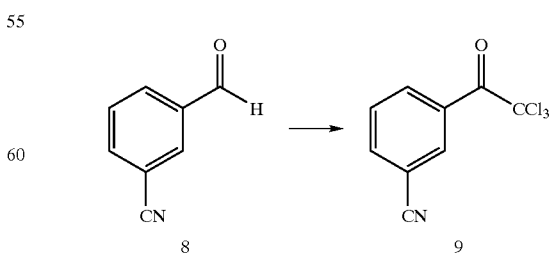

Into a mixture of lead(II) bromide (1.69 g, 4.60 mmol) and finely cut aluminum foil (1.25 g, 45.8 mmol) in DMF (226 mL) was added 3-cyanobenzaldehyde (6.01 g, 45.8 mmol) and carbon tetrachloride (8.84 mL, 91.7 mmol), and the mixture was stirred at ambient temperature 3 hours. The reaction was quenched with aqueous 1N hydrochloric acid (100 mL), and the mixture was extracted with ethyl acetate (3×300 mL). The combined organic extracts were washed with brine (200 mL), dried with magnesium sulfate, filtered, evaporated in vacuo, and dried under high vacuum to give the trichloromethyl carbinol (9) as a brown oil in quantitative yield.

$^1$H NMR (CDCl$_3$, 300 MHz): δ 7.94 (1H, m), 7.86 (1H, m), 7.66 (1H, m), 7.48 (1H, m), 5.24 (1H, s), 4.98 (1H, bs).

Step (b): Preparation of 2-(3-Cyanophenyl)-3,4-dihydro-2H-1,4-benzoxazin-3-one

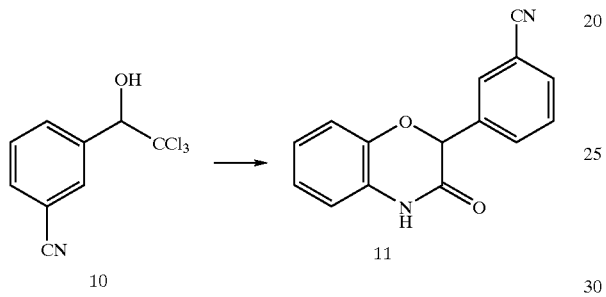

To o-aminophenol hydrochloride (3.29 g, 13.1 mmol) in DMSO (15 mL) was added sodium hydride (2.63 g, 65.8 mmol). After bubbling and evolution of heat ceased, a solution of (10) (3.29 g, 13.1 mmol) in DMSO (10 mL) was added dropwise over 15 minutes. After evolution of heat ceased, the mixture was stirred at 70° C. for 4 hours. The reaction mixture was cooled, diluted with water, and extracted with ethyl acetate (5×500 mL). The combined organic extracts were washed with brine (200 mL), dried with magnesium sulfate, filtered, and evaporated in vacuo. The residue was purified on a silica gel column eluted with 25% ethyl acetate in dichloromethane. The product (11) was isolated 0.55 g (17%) as an orange solid.

$^1$H NMR (CDCl$_3$, 300 MHz): δ 8.47 (1H, s), 7.80–7.72 (2H, m), 7.64 (1H, m), 7.49 (1H, m), 7.15–6.97 (3H, m), 6.82 (1H, m), 5.70 (1H, s).

Step (c): Preparation of 4-(5-Bromopentyl)-2-(3-cyanophenyl)-3,4-dihydro-2H-1,4-benzoxazin-3-one

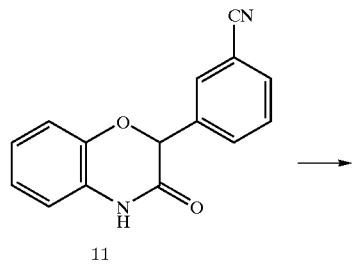

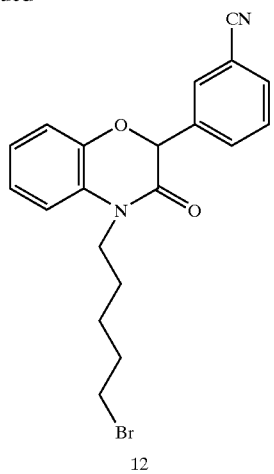

To the benzoxazinone (11) (0.72 g, 2.87 mmol) in DMF (5 mL) was added sodium hydride (0.126 g, 3.15 mmol), and the solution was stirred at 70° C. for 15 minutes until bubbling stopped. To this solution was added 1,5-dibromopentane (1.57 mL, 11.5 mmol) and the solution was stirred at 70° C. for additional 3 hours. The solution was cooled, diluted with water, and extracted with ethyl acetate (5×200 mL). The combined organic extracts were washed with brine (2×100 mL), dried with magnesium sulfate, filtered, and evaporated in vacuo. The residue was purified on a silica gel column eluted with 20% to 40% ethyl acetate in hexane. The product (12) was isolated 0.64 (56%) as a yellow oil.

$^1$H NMR (CDCl$_3$, 300 MHz): δ 7.71 (2H, m), 7.61 (1H, m), 7.46 (1H, m), 7.12–7.03 (3H, m), 6.97 (1H, m), 5.69 (1H, s), 3.98 (2H, m), 3.41 (2H, m), 1.91 (2H, m), 1.71 (2H, m), 1.55 (2H, m).

Step (d): Preparation of 4-5-[(2R,6S)-2,6-Dimethylhexahydro-1-pyridinyl]pentyl-2-(3-cyanophenyl)-3,4-dihydro-2H-1,4-benzoxazin-3-one

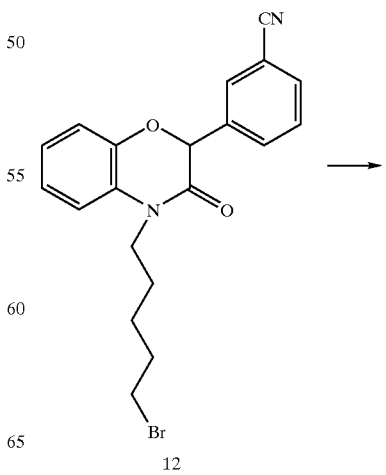

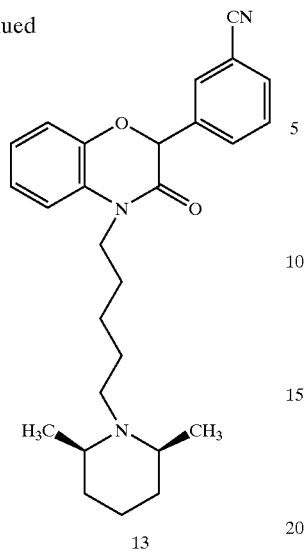

13

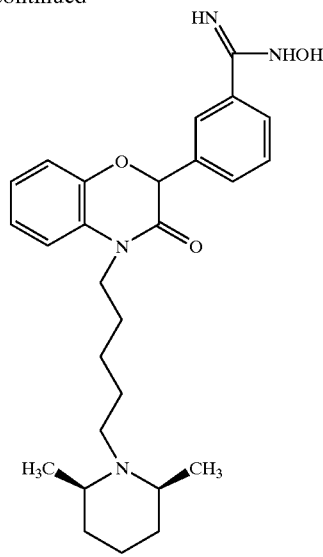

14

To (12) (1.08 g, 2.70 mmol) was added cis-2,6-dimethylpiperidine (8 mL, 60 mmol). The solution was stirred at 70° C. for 16 hours. The solution was cooled, diluted with water, and extracted with ethyl acetate (3×200 mL). The combined organic extracts were washed with saturated sodium bicarbonate (2×100 mL), washed with brine (2×100 mL), dried with magnesium sulfate, filtered, evaporated in vacuo, coevaporated with toluene, and dried under high vacuum to give 1.09 g (94%) of (13) as a yellow oil.

$^1$H NMR (CDCl$_3$, 300 MHz): δ 7.63 (2H, m), 7.54 (1H, m), 7.40 (1H, m), 7.13 (1H, m), 7.03–6.85 (3H, m), 5.63 (1H, s), 3.91 (2H, m), 2.91 (2H, m), 2.70 (2H, m), 2.61–2.06 (4H, m) 1.64–1.18 (8H, bm), 1.06 (6H, m). HPLC: RT=13.88 min. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Step (e): Preparation of 3-(4-5-[(2R,6S)-2,6-Dimethylhexahydro-1-pyridinyl]pentyl-3-oxo-3,4-dihydro-2H-1,4-benzoxazin-2-yl)-1-N-hydroxybenzenecarboximidamide To (13) (1.09 g, 2.53 mmol) in methanol (30 mL) were added hydroxylamine hydrochloride (0.438 g, 6.30 mmol) and diisopropylethylamine (0.44 mL, 2.53 mmol). The solution was stirred at room temperature for 16 hours. The solvent was evaporated in vacuo, and the oil was dried under high vacuum to give (14) in quantitative yield.

HPLC: RT=8.39 min. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Step (f): Preparation of 3-(4-5-[(2R,6S)-2,6-Dimethylhexahydro-1-pyridinyl]pentyl-3-oxo-3,4-dihydro-2H-1,4-benzoxazin-2-yl)-1-N-hydroxytrifluoroacetatebenzenecarboximidamide

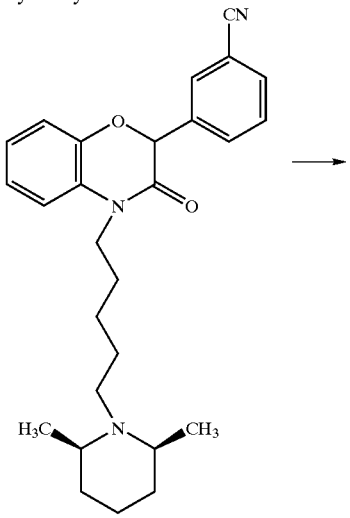

13

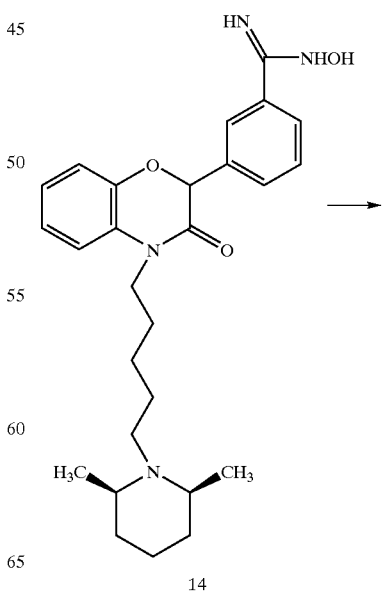

14

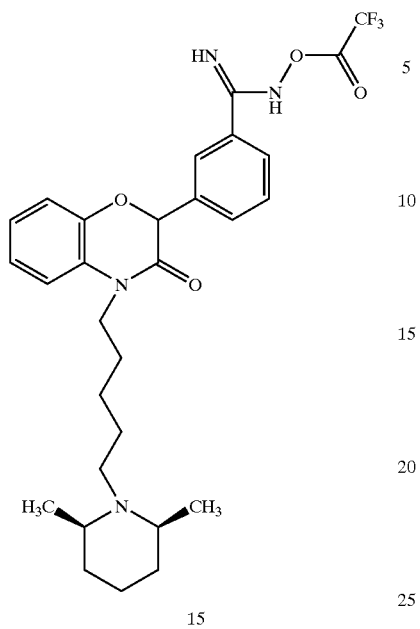

15

To (14) (0.53 g, 1.14 mmol) was added trifluoroacetic anhydride (7 mL), and the solution was stirred at room temperature for 2 hours. The solvent was removed in vacuo to give (15) as a yellow oil in quantitative yield. HPLC: RT=17.44 min. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Step (g): Preparation of 3-(4-5-[(2R,6S)-2,6-Dimethylhexahydro-1-pyridinyl]pentyl-3-oxo-3,4-dihydro-2H-1,4-benzoxazin-2-yl)-1-benzenecarboximidamide

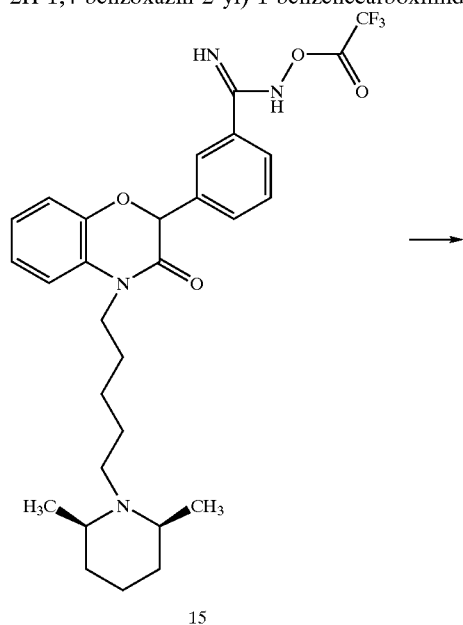

15

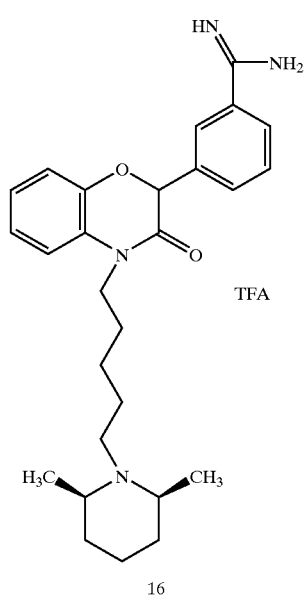

16

To (15) (0.57 g, 1.13 mmol) in trifluoroacetic acid (16 mL) was added 20% palladium on carbon (0.1 g), and the mixture was hydrogenated at 23° C. for 48 hours. The mixture was filtered and the filter pad washed with trifluoroacetic acid. The combined filtrate and washings were evaporated in vacuo, and the residue was purified by preparative HPLC (Vydac 218TP1022 C-18, eluted with a mixture of solvents consisting of (i) 0.1% trifluoroacetic acid in water, and (ii) 0.1% trifluoroacetic acid in acetonitrile, gradient profile 95:5 (i):(ii) to 60:40 (i):(ii) over 90 minutes, flow rate 20 mL/minute, λ=214 nM) and lyophilized to give 251 mg (50%) of the bis TFA salt of (16). To (16) in acetonitrile (2 mL) and water (2 mL) was added Amberlite® IRA-400(Cl) ion exchange resin (3.36 g). The mixture was filtered, and the filtrate was lyophilized to give 155 mg (26%) of the bis hydrochloride salt (16).

$^1$H NMR (CDCl$_3$, 300 MHz): δ 9.44 (1H, s), 9.19 (2H, s), 7.80 (2H, m), 7.64 (2H, m), 7.28 (1H, m), 7.11–7.01 (3H, m), 5.93 (1H, s), 3.97 (2H, m), 3.18 (2H, bs), 3.03 (2H, bs), 1.75–1.36 (12H, bm), 1.23 (6H, m). CI MS M+1=449. HPLC: RT=8.26. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

EXAMPLE 3

3-(4-5-[(2R,6S)-2,6-Dimethylhexahydro-1-pyridinyl]pentyl-3-oxo-3,4-dihydro-2H-1,4-benzothiazin-2-yl)-1-benzenecarboximidamide Step (a): Preparation of 2-(3-Cyanophenyl)-3,4-dihydro-2H-1,4-benzothiazin-3-one

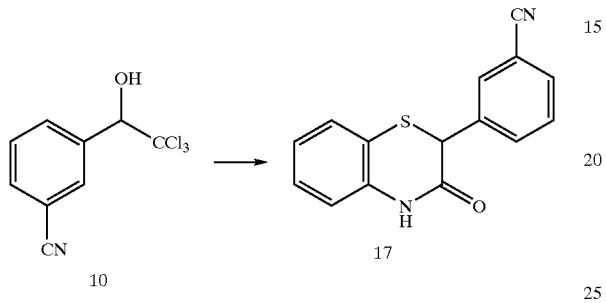

To o-aminothiophenol (2.39 mL, 22.3 mmol) in DMF (60 mL) was added sodium hydride (3.61 g, 90.3 mmol). After bubbling and evolution of heat ceased, a solution of (10) (5.67 g, 22.6 mmol) in DMSO (40 mL) was added dropwise over 15 minutes. After evolution of heat ceased, the mixture was stirred at 50° C. for 6 hours and at room temperature for 16 hours. The reaction mixture was cooled, diluted with water, and extracted with ethyl acetate (5×500 mL). The combined organic extracts were washed with brine (200 mL), dried with magnesium sulfate, filtered, and evaporated in vacuo. The residue was absorbed onto silica gel and purified on a silica gel column eluted with 1% to 4% methanol in dichloromethane. The residue was crystallized from ethyl acetate and hexane to give 1.71 g (29%) of product (17) as a tan solid.

$^1$H NMR (CDCl$_3$, 300 MHz): δ 10.97 (1H, s), 7.75 (1H, m), 7.57 (2H, m), 7.32 (1H, m), 7.20 (1H, m), 7.00 (3H, m), 5.10 (1H, s).

Step (b): Preparation of 4-(5-Bromopentyl)-2-(3-cyanophenyl)-3,4-dihydro-2H-1,4-benzothiazin-3-one

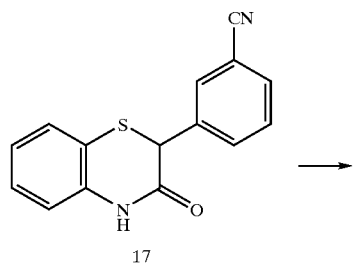

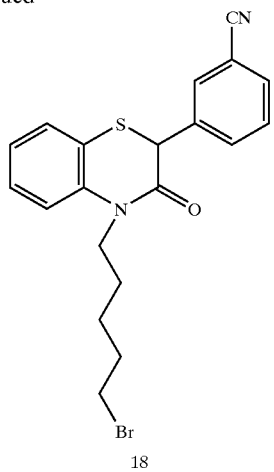

To the benzothiazinone (17) (0.75 g, 2.82 mmol) in DMF (5 mL) was added sodium hydride (0.124 g, 3.09 mmol), and the solution was stirred at 70° C. for 15 minutes until bubbling stopped. To this solution was added 1,5-dibromopentane (1.54 mL, 11.2 mmol), and the solution was stirred at 70° C. for additional 16 hours. The solution was cooled, diluted with water, and extracted with ethyl acetate (3×300 mL). The combined organic extracts were washed with brine (2×100 mL), dried with magnesium sulfate, filtered, and evaporated in vacuo. The residue was purified on a silica gel column eluted with 20% to 30% ethyl acetate in hexane. The product (18) was isolated 0.66 (52%) as a yellow oil.

$^1$H NMR (CDCl$_3$, 300 MHz): δ 7.57 (3H, m), 7.38 (2H, m), 7.25 (1H, m), 7.11–7.01(2H, m), 4.64 (1H, s), 4.09 (2H, m), 3.40 (2H, m), 1.91 (2H, m), 1.70 (2H, m), 1.53 (2H, m).

Step (c): Preparation of 4-5-[(2R,6S)-2,6-Dimethylhexahydro-1-pyridinyl]pentyl-2-(3-cyanophenyl)-3,4-dihydro-2H-1,4-benzothiazin-3-one

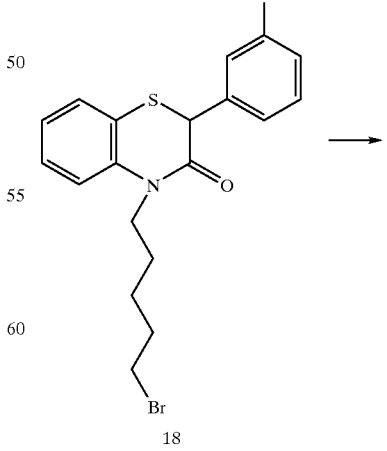

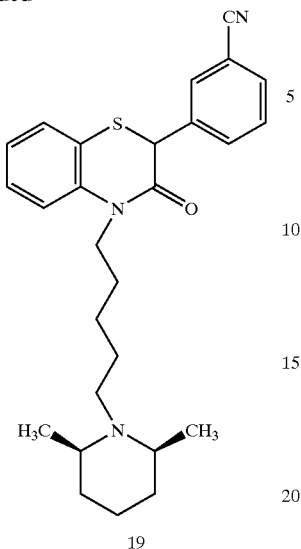

19

To (18) (0.66 g, 1.59 mmol) was added cis-2,6-dimethylpiperidine (6.0 mL, 44 mmol). The solution was stirred at 70° C. for 48 hours. The solution was cooled, diluted with water, and extracted with ethyl acetate (3×200 mL). The combined organic extracts were washed with saturated sodium bicarbonate (2×100 mL), washed with brine (2×100 mL), dried with magnesium sulfate, filtered, evaporated in vacuo, coevaporated with toluene, and dried under high vacuum to give 0.69 g (97%) of (19) as a yellow oil.

$^1$H NMR (CDCl$_3$, 300 MHz): δ 7.55 (3H, m), 7.37 (2H, m), 7.24 (1H, m), 7.10–7.00 (2H, m), 4.63 (1H, s), 4.07 (2H, m), 2.74 (2H, m), 2.47 (2H, m), 1.76–1.22 (12H, bm), 1.08 (6H, m). HPLC: RT=14.16 min. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Step (d): Preparation of 3-(4-5-[(2R,6S)-2,6-Dimethylhexahydro-1-pyridinyl]pentyl-3-oxo-3,4-dihydro-2H-1,4-benzothiazin-2-yl)-1-N-hydroxybenzenecarboximidamide

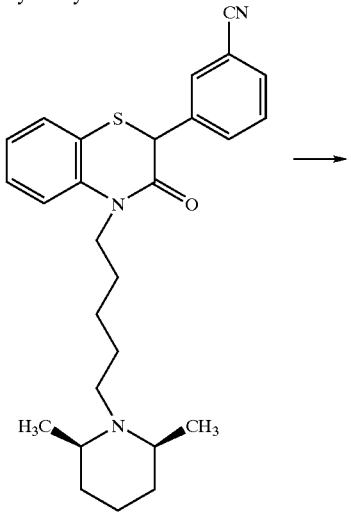

19

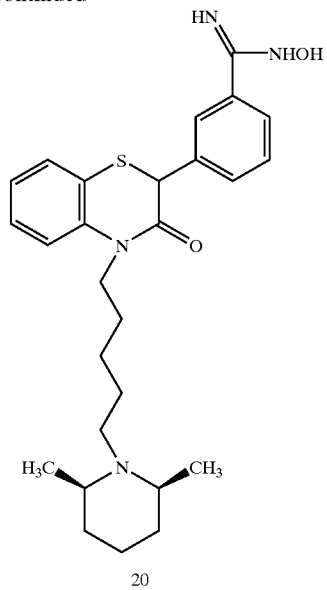

20

To (19) (0.30 g, 0.67 mmol) in methanol (10 mL) were added hydroxylamine hydrochloride (0.1 16 g, 1.67 mmol) and diisopropylethylamine (0.12 mL, 0.67 mmol). The solution was stirred at room temperature for 24 hours. The solvent was evaporated in vacuo, and the oil was dried under high vacuum to give (20) in quantitative yield.

HPLC: RT=8.83 min. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Step (e): Preparation of 3-(4-5-[(2R,6S)-2,6-Dimethylhexahydro-1-pyridinyl]pentyl-3-oxo-3,4-dihydro-2H-1,4-benzothiazin-2-yl)-1-N-hydroxyacetatebenzenecarboximidamide

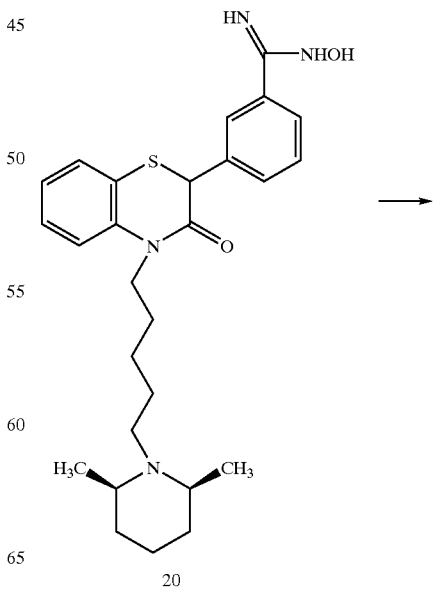

20

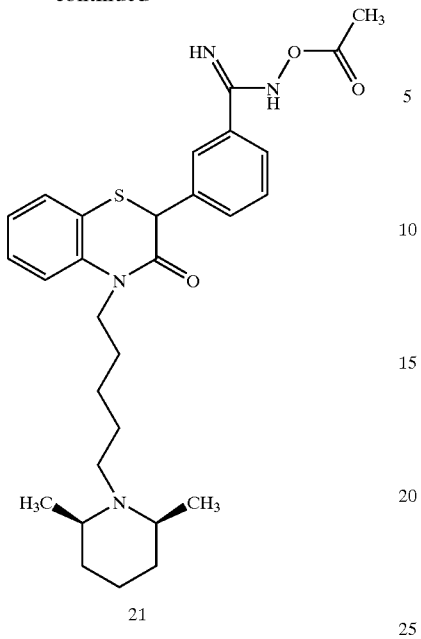

21

To (20) (0.32 g, 0.66 mmol) was added acetic anhydride (2 mL) and the solution was stirred at room temperature for 2 hours. The solution was diluted with acetic acid, and the solvent was evaporated in vacuo to give (21) as a yellow oil in quantitative yield.

HPLC: RT=12.08 min. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Step (f): Preparation of 3-(4-5-[(2R,6S)-2,6-Dimethylhexahydro-1-pyridinyl]pentyl-3-oxo-3,4-dihydro-2H-1,4-benzothiazin-2-yl)-1-benzenecarboximidamide

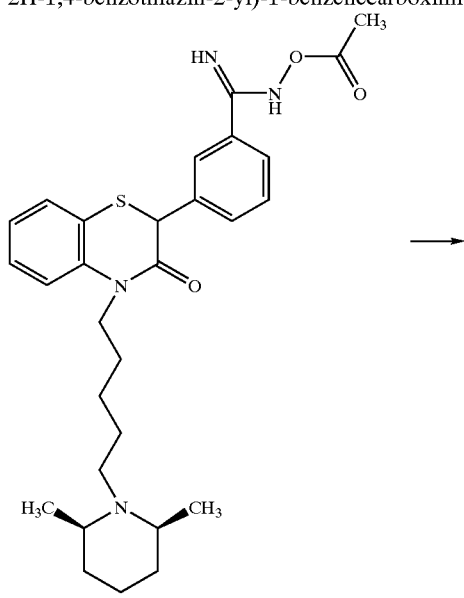

21

→

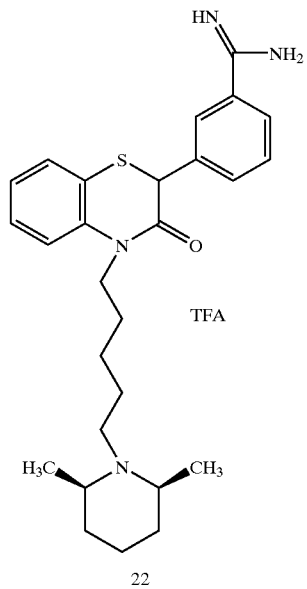

22

To (21) (0.34 g, 0.65 mmol) in acetic acid (2 mL) was added 20% palladium on carbon (45 mg) and hydrogenated at 23° C. for 2 hours. The mixture was filtered through Celite and the filter pad washed with acetic acid. The combined filtrate and washings were evaporated in vacuo, and purified by preparative HPLC (Vydac 218TP1022 C-18, eluted with a mixture of solvents consisting of (i) 0.10% trifluoroacetic acid in water, and (ii) 0.1% trifluoroacetic acid in acetonitrile, gradient profile 95:5 (i):(ii) to 60:40 (i):(ii) over 90 minutes, flow rate 20 mL/minute, λ=214 nM) and lyophilized to give 50 mg (16%) of product (22) as a fluffy off-white solid.

$^1$H NMR (DMSO, 400 MHz): δ 9.33 (1H, s), 9.18 (1H, s), 7.69 (3H, m), 7.55 (1H, m), 7.41 (2H, m), 7.33 (1H, m), 7.07 (1H, m), 5.11 (1H, s), 4.09 (2H, m), 3.38 (2H, m), 3.24 (2H, m), 3.10 (2H, m), 2.91 (2H, m), 1.84 (2H, m), 1.66–1.33 (6H, bm), 1.24 (6H, m). CI MS M+1=465, M−1=464. HPLC: RT=8.92 min. (86%) and 8.19 min. (13%). (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nM).

Example 4

3-(4-5-[(2R,6S)-2,6-Dimethylhexahydro-1-pyridinyl]pentyl-3-oxo-3,4-dihydro-2H-1,4-benzothiazin-2-yl)-1-benzenecarbothioamide

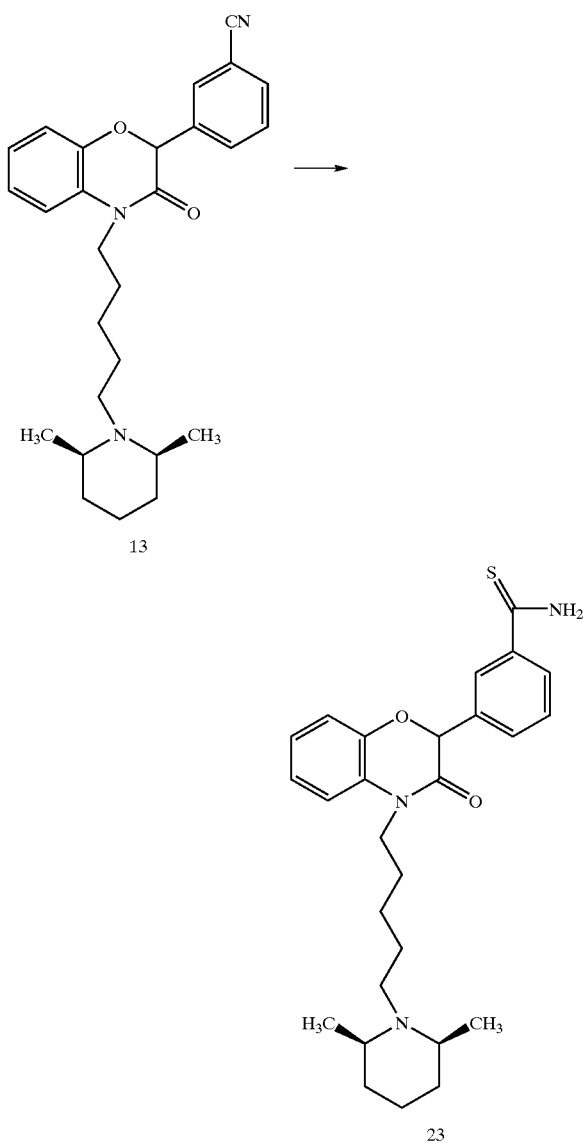

In a three-necked flask, intermediate (13) (0.49 g, 1.14 mmol) was dissolved in pyridine (50 mL). Nitrogen was bubbled through the solution for 30 minutes. Hydrogen sulfide was bubbled through the yellow solution for 20 minutes. The solution turned green and the flask was sealed and stirred for 24 hours at room temperature. HPLC indicated that the reaction was complete. Nitrogen was bubbled through the solution for 30 minutes. The solution was evaporated in vacuo, coevaporated with toluene, and purified by preparative HPLC (Vydac 218TP1022 C-18, eluted with a mixture of solvents consisting of (i) 0.1% trifluoroacetic acid in water, and (ii) 0.1% trifluoroacetic acid in acetonitrile, gradient profile 95:5 (i):(ii) to 60:40 (i):(ii) over 90 minutes, flow rate 20 mL/minute, $\lambda$=214 nM) and lyophilized to give 28 mg (6%) of product (23) as a yellow solid.

$^1$H NMR (DMSO, 400 MHz): δ 9.92 (1H, s), 9.55 (1H, s), 7.97 (1H, s), 7.75 (1H, m), 7.48 (1H, m), 7.41 (1H, m), 7.25 (1H, m), 7.14–6.99 (3H, m), 5.91 (1H, s), 3.99 (2H, m), 3.37 (2H, bs), 3.24 (2H, bs), 3.11 (2H, m), 2.92 (2H, bs), 1.84 (2H, m), 1.70–1.38 (6H, m), 1.23 (6H, m). CI MS M+1=466. HPLC: RT=12.48 min. (Beckman 235328 C-18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, $\lambda$=214 nM).

Example 5

3-(4-5-[(2R,6S)-2,6-Dimethyltetrahydro-1(2H)-pyridinyl]pentyl-3-oxo-3,4-dihydro-2H-1,4-benzoxazin-2-yl)4-hydroxybenzenecarboximidamide Step (a): Preparation of 2-(Benzyloxy)-5-bromobenzenecarbaldehyde

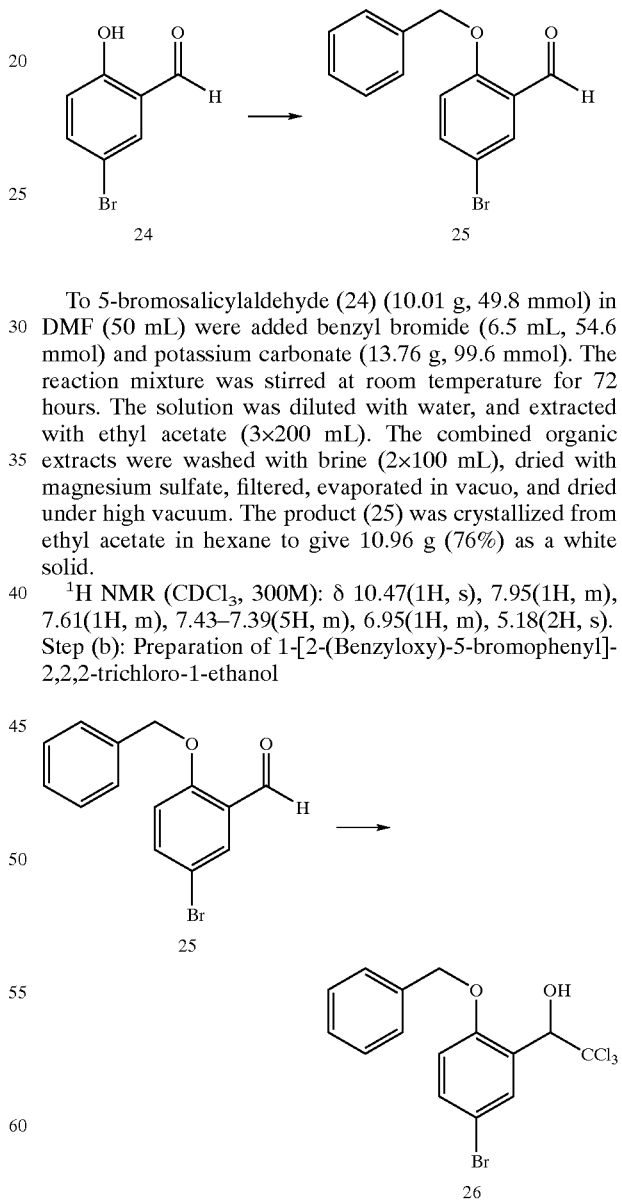

To 5-bromosalicylaldehyde (24) (10.01 g, 49.8 mmol) in DMF (50 mL) were added benzyl bromide (6.5 mL, 54.6 mmol) and potassium carbonate (13.76 g, 99.6 mmol). The reaction mixture was stirred at room temperature for 72 hours. The solution was diluted with water, and extracted with ethyl acetate (3×200 mL). The combined organic extracts were washed with brine (2×100 mL), dried with magnesium sulfate, filtered, evaporated in vacuo, and dried under high vacuum. The product (25) was crystallized from ethyl acetate in hexane to give 10.96 g (76%) as a white solid.

$^1$H NMR (CDCl$_3$, 300M): δ 10.47(1H, s), 7.95(1H, m), 7.61(1H, m), 7.43–7.39(5H, m), 6.95(1H, m), 5.18(2H, s).

Step (b): Preparation of 1-[2-(Benzyloxy)-5-bromophenyl]-2,2,2-trichloro-1-ethanol Into a mixture of lead(II) bromide (1.38 g, 3.76 mmol) and finely cut aluminum foil (1.02 g, 37.8 mmol) in DMF (188 mL) were added (25) (10.96 g, 37.6 mmol) and carbon tetrachloride (7.6 mL, 78.8 mmol), and the mixture was stirred at ambient temperature 3 hours. The reaction was quenched with aqueous 1N hydrochloric acid (100 mL), and the mixture was extracted with ethyl acetate (3×300 mL). The combined organic extracts were washed with brine (200 mL), dried with magnesium sulfate, filtered, evaporated in vacuo, and dried under high vacuum to give the trichloromethyl carbinol (26) as a brown oil in quantitative yield.

$^1$H NMR (CDCl$_3$, 300MHz): δ 7.82(1H, m), 7.46–7.37 (6H, m), 6.87(1H, m), 5.71(1H, s), 5.11(2H, m), 3.85(1H, bs).

Step (c): Preparation of 2-[2-(Benzyloxy)-5-bromophenyl]-2H-1,4-benzoxazin-3(4H)-one

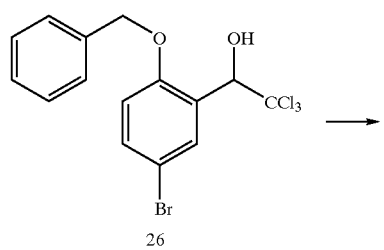

26

To o-aminophenol hydrochloride (0.88 g, 6.04 mmol) in DMSO (15 mL) was added sodium hydride (1.21 g, 30.2 mmol). After bubbling and evolution of heat ceased, a solution of (26) (2.50 g, 6.09 mmol) in DMSO (10 mL) was added dropwise over 30 minutes at room temperature. After evolution of heat ceased, the mixture was stirred at 70° C. for 4 hours. The reaction mixture was cooled, diluted with water, and extracted with ethyl acetate (5×500 mL). The combined organic extracts were washed with brine (200 mL), dried with magnesium sulfate, filtered, and evaporated in vacuo. The residue was purified on a silica gel column eluted with 20% ethyl acetate in hexane. The product (27) was isolated 0.67 g (27%) as a solid.

$^1$H NMR (CDCl$_3$, 300MHz): δ 7.91(1H, bs), 7.51(1H, m), 7.43(1H, m), 7.27(5H, m), 6.97–6.85(4H, m), 6.67(1H, m), 5.83(1H, s), 5.05(2H, m).

Step (d): Preparation of 4-(Benzyloxy)-3-(3-oxo-3,4-dihydro-2H-1,4-benzoxazin-2-yl)benzenecarbonitrile

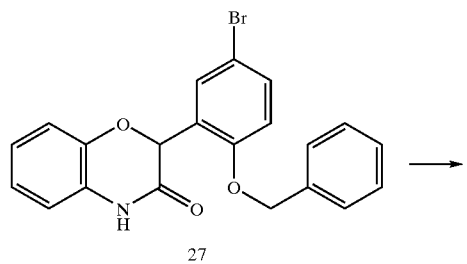

27

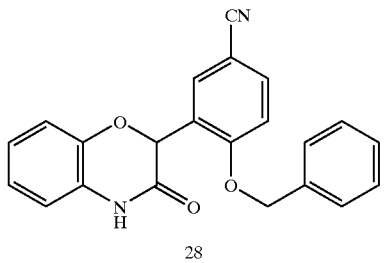

28

A mixture of the benzoxazinone (27) (0.17 g, 0.477 mmol) and cuprous cyanide (0.09 g, 1.00 mmol) in DMF (3 mL) was stirred at 160° C. for 16 hours in a sealed tube. The solution was cooled, diluted with water (50 mL) and ammonium hydroxide (50 mL), and extracted with ethyl acetate (3×100 mL). The combined organic extracts were washed with brine (2×100 mL), dried with magnesium sulfate, filtered, evaporated in vacuo, and dried under high vacuum to give 0.16 g (94%) of product (28) as a solid. $^1$H NMR (CDCl$_3$, 300 MHz): δ 9.82(1H, bs), 7.73–7.64(2H, m), 7.31(5H, m), 7.06–6.96(4H, m), 6.70(1H, m), 5.86(1H, s), 5.15(2H, m). CI MS M+1=357 M−1=356.

Step (e): Preparation of 4-(Benzyloxy-3-[4-(5-bromopentyl)-3-oxo-3,4-dihydro-2H-1,4-benzoxazin-2-yl] benzenecarbonitrile

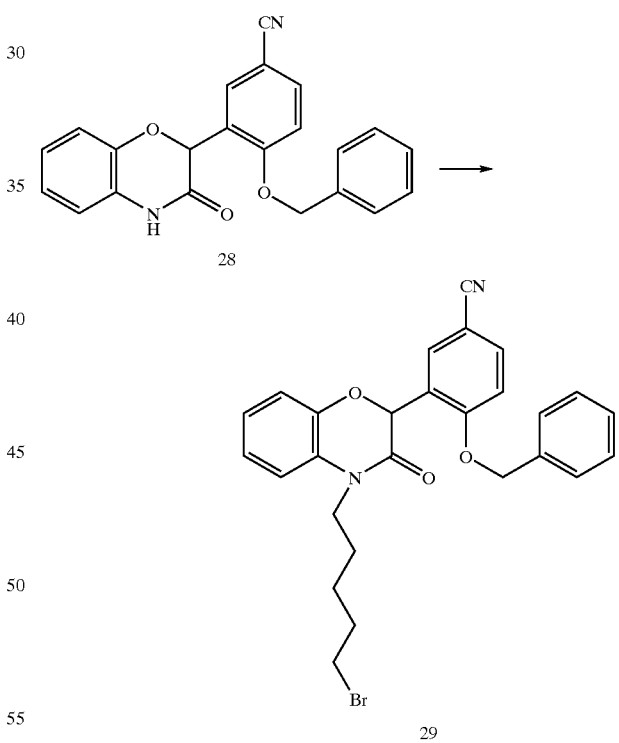

To the benzoxazinone (28) (1.63 g, 4.57 mmol) in DMF (5 mL) was added sodium hydride (0.20 g, 5.00 mmol) and the solution was stirred at 0° C. for 10 minutes until bubbling stopped. To this solution was added 1,5-dibromopentane (2.5 mL, 18.3 mmol) and the solution was stirred at 0° C. for additional 2 hours. The solution was diluted with water, and extracted with ethyl acetate (5×200 mL). The combined organic extracts were washed with brine (2×100 mL), dried with magnesium sulfate. filtered, and evaporated in vacuo. The residue was purified on a silica gel column eluted with 20% ethyl acetate in hexane. The product (29) was isolated 1.14 g (61%) as a foam.

¹H NMR (CDCl₃, 300 MHz): δ 7.63(2H, m), 7.31(5H, m), 7.07–6.94(5H, m), 5.83(1H, s), 5.14(2H, m), 3.89(2H, m), 3.37(2H, m), 1.86(2H, m), 1.55(4H, m). CI MS M+1=507/505 M−1=506/504.

Step (f) Preparation of 4-(Benzyloxy)-3-(4-5-[(2R,6S)-2,6-dimethyltetrahydro-1(2N)-pyridinyl]pentyl-3-oxo-3,4-dihydro-2H-1,4-benzoxazin-2-yl)benzenecarbonitrile

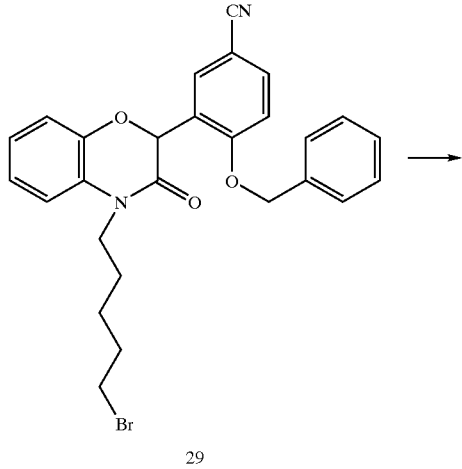

29

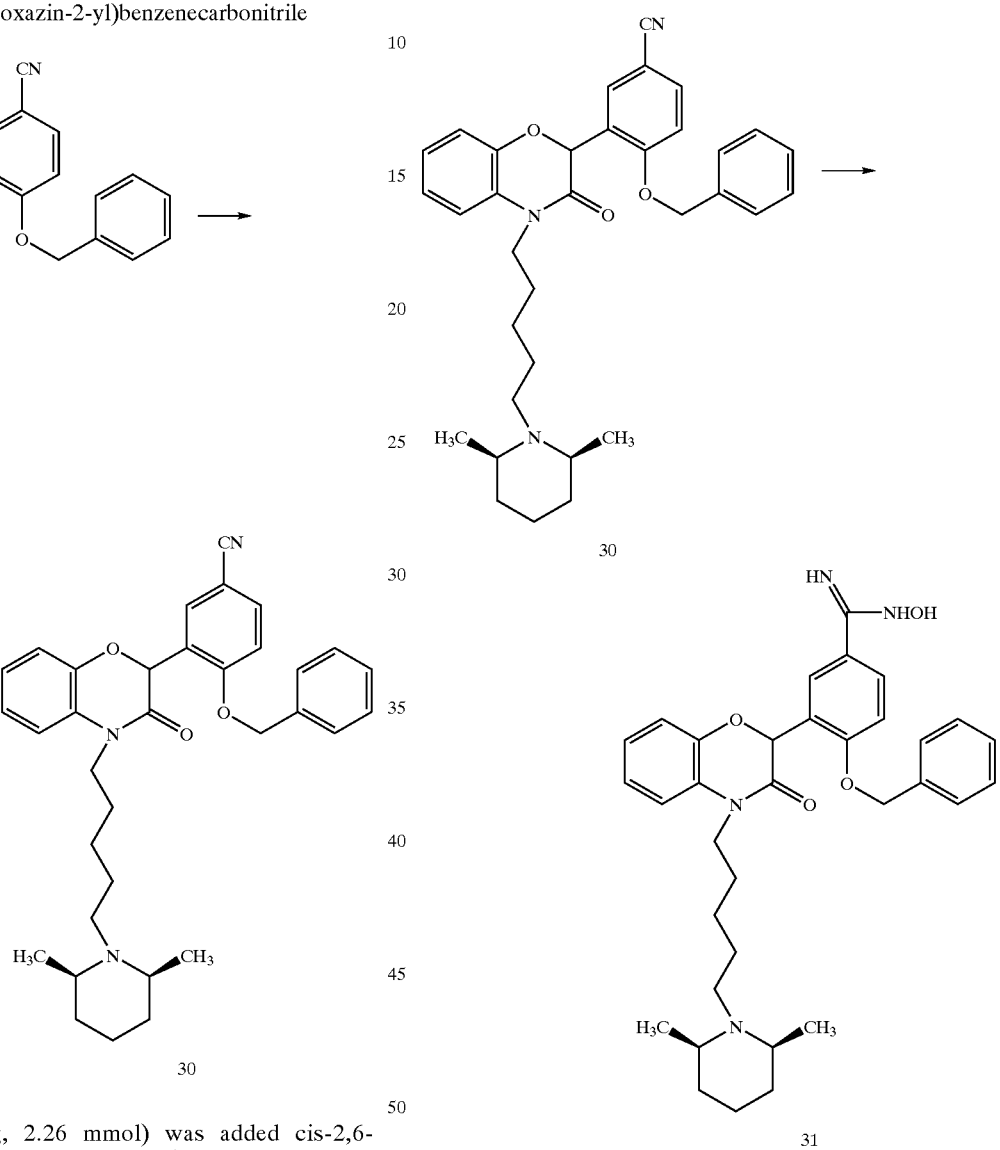

To (29) (1.14 g, 2.26 mmol) was added cis-2,6-dimethylpiperidine (10 mL, 74 mmol). The solution was stirred at 70° C. for 16 hours. The solution was cooled, diluted with water, and extracted with ethyl acetate (3×200 mL). The combined organic extracts were washed with saturated sodium bicarbonate (2×100 mL), washed with brine (2×100 mL), dried with magnesium sulfate, filtered, evaporated in vacuo, coevaporated with toluene, and dried under high vacuum to give (30) as a yellow oil in quantitative yield.

¹H NMR (CDCl₃, 300 MHz): δ 7.56(2H, m), 7.25(5H, m), 7.10(1 H, m), 7.00–6.89(4H, m), 5.78(1H, s), 5.09(2H, m), 3.80(2H, m), 2.64(2H, bs), 2H, bs), 1.59–1.15(12H, bm), 1.00(6H, m). HPLC: RT=16.26 minutes (Beckman 235328 C18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nm).

Step (g): Preparation of 4-(Benzyloxy)-3-(4-5-[(2R,6S)-2,6-dimethyltetrahydro-1(2H-pyridinyl]pentyl-3-oxo-3,4-dihydro-2H-1,4-benzoxazin-2-yl)-N-hydroxybenzenecarboximidamide To (30) (1.21 g, 2.25 mmol) in methanol (25 mL) were added hydroxylamine hydrochloride (0.39 g, 5.61 mmol) and diisopropylethylamine (0.39 mL, 2.24 mmol). The solution was stirred at room temperature for 16 hours. The solvent was evaporated in vacuo and the oil was dried under high vacuum to give (31) in quantitative yield.

HPLC: RT=13.46 minutes (Beckman 235328 C18 5 μm 4.6 mm×25 cm. eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nm).

69

Step (h): Preparation of 4-(Benzyloxy)-3-(4-5-[(2R,6S)-2,6-dimethyltetrahydro-1(2H)-pyridinyl]pentyl-3-oxo-3,4-dihydro-2H-1,4-benzoxazin-2-yl)-N-[(2,2,2-trifluoroacetyl)oxy]benzenecarboximidamide

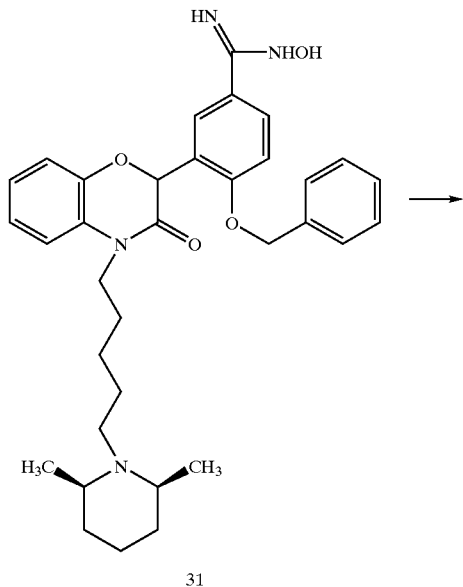

31

To (31) (1.28 g, 2.24 mmol) was added trifluoroacetic anhydride (10 mL) and the solution was stirred at room temperature for 2 hours. The solvent was removed in vacuo to give (32) as a yellow oil in quantitative yield.

HPLC: RT=21.62 minutes (Beckman 235328 C18 5 μm 4.6 mm×25 cm. eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nm).

70

Step (i): Preparation of 3-(4-5-[(2R,6S)-2,6-Dimethyltetrahydro-1(2H)-pyridinyl]pentyl-3-oxo-3,4-dihydro-2H-1,4-benzoxazin-2-yl)-4-hydroxybenzenecarboximidamide

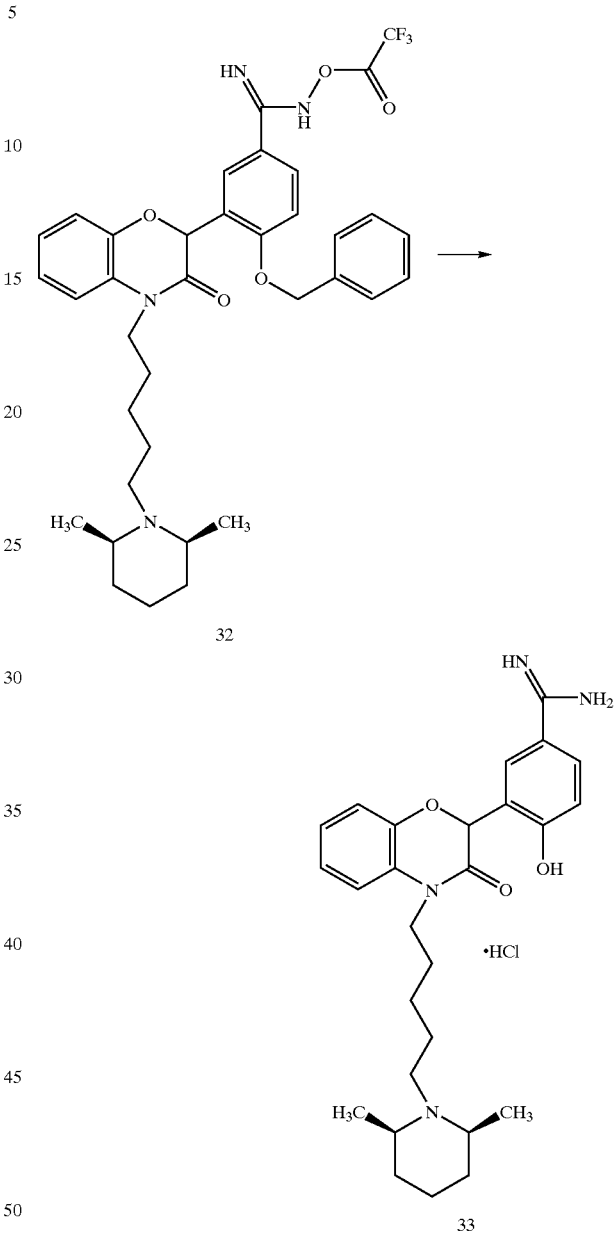

To (32) (0.1.49 g, 2.24 mmol) in trifluoroacetic acid (32 mL) was added 20% palladium on carbon (0.2 g) and hydrogenated at 23° C. for 48 hours. The mixture was filtered and the filter pad washed with trifluoroacetic acid. The combined filtrate and washings were evaporated in vacuo, and the residue was purified by preparative HPLC (Vydac 218TP54 C18, eluted with a mixture of solvents consisting of (i) 0.1% trifluoroacetic acid in water, and (ii) 0.1% trifluoroacetic acid in acetonitrile, gradient profile 95:5 (i):(ii) to 60:40 (i):(ii) over 90 minutes, flow rate 20 mL/minute, λ=214 nm) and lyophilized to afford a white powder. To the white powder in acetonitrile (2 mL) and water (200 mL) was added Amberlite® IRA-400(Cl) ion exchange resin. The mixture was filtered, and the filtrate was lyophilized to give 553 mg (45%) of (33) as a white solid.

¹H NMR (DMSO, 300 MHz): δ 11.22(1H, s), 9.16(1H, s), 8.86(2H, s), 7.74(2H, m), 7.25(1H, m), 7.11–6.95(4H, m), 5.78(1H, s), 4.06–3.93(2H, m), 3.17(2H, m) 3.05(2H, m), 1.79–1.37(12H, m), 1.23(6H, m). CI MS M+1=465 HPLC: RT=8.22 (Beckman 235328 C18 5 μm 4.6 mm×25 cm, eluted with a mixture of solvents consisting of (i) 0.1% trifluoroacetic acid in water, and (ii) 0.1% trifluoroacetic acid in acetonitrile, gradient profile 80:20 (i):(ii) to 10:90 (i):(ii) over 23 minutes, flow rate 1.5 mL/minute, λ=214 nm).

Example 6

3-((2S)-4-5-[(2R,6S)-2,6-Dimethyltetrahydro-1(2H)-pyridinyl]pentyl-3-oxo-3,4-dihydro-2H-1,4-benzoxazin-2-yl)-4-hydroxybenzenecarboximidamide Step (a): Preparation of 2-(Benzyloxy)-5-bromobenzenecarbaldehyde

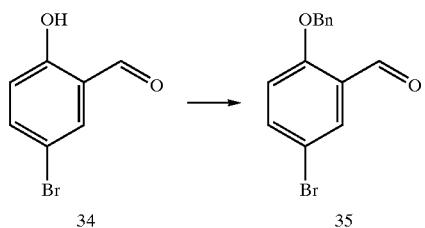

5-bromosalicylaldehyde (34) (50.0 g, 0.249 moles) was suspended in 150 ml EtOH with stirring. KOH (13.97 g, 0.249 moles) was dissolved in 40 ml water and added to the aldehyde suspension. After 30 minutes benzyl bromide (51.05 g, 35.5 ml, 0.298 moles) was added slowly. The mixture was refluxed overnight. After cooling to room temperature water (50 mL) was added and then after 5 minutes an off white solid was collected by filtration. This was dried overnight in vacuum to afford 61.71 g of the desired product (35), 84.6% yield. 1H NMR (CDCl₃) δ 10.46 (1H, s), 7.94 (1H, d), 7.60 (1H, dd), 7.41 (5H, m), 6.95 (1H, d), 5.18 (2H, s). APCI MS: No M+1, M-91 (201). HPLC: 20.91 min. on C-18 column @ 1.5 ml/min. 20% CH3CN(0.1% TFA) in H2O(0.1% TFA)→90% CH3CN (0.1% TFA) in H2O(0.1% TFA) (0→22 min.)

Step (b): Preparation of 2-[2-(Benzyloxy)-5-bromophenyl]-2-hydroxyacetonitrile

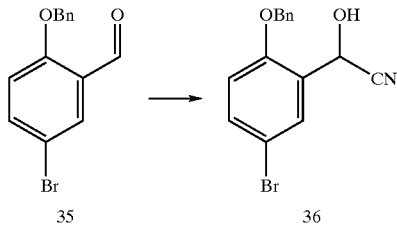

To a suspension of (35) (50 g, 0.172 moles) in MeOH (400 mL) was added KCN (50.31 g, 0.773 moles) which generated a yellow color. Acetic acid (15.72 ml, 0.275 moles) was added dropwise over 10 minutes, and the reaction stirred at room temp. for 2.5 hours. The mixture was. filtered and concentrated by 75%. Ethyl acetate (250 mL) was added and then after washing with water (2×150 ml), sat. NaCl (1×150 ml), the organic phase was dried over MgSO₄, and finally concentrated to a brown oil. Chromatographed on flash silica using 10%→20% ethyl acetate in hexane affords (36) 35.4 g desired product, 64.8% yield. (1H NMR CDCl₃) δ 7.58 (1H, d), 7.35–7.50 (6H, m), 6.95 (1H, d), 5.55 (1H, d), 5.18 (2H, s), 3.30 (1H, d). APCI MS No M+1, M-91 (201): HPLC: 18.04 min. on C-18 column @ 1.5 ml/min. 20% CH3CN(0.1% TFA) in H2O(0.1% TFA) →90% CH3CN(0.1% TFA) in H2O(0.1% TFA) (0→22 min.)

Step (c): Preparation of Methyl 2-[2-(Benzyloxy)-5-bromophenyl]-2-hydroxyacetate

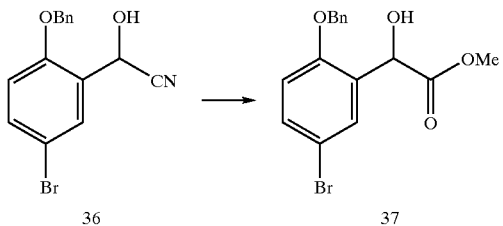

Diethyl ether (45 mL), dioxane (45 mL), MeOH (12 mL) were mixed at room temp. and then HCL gas was bubbled into the solution for 3–4 minutes at a good rate (to make a saturated HCl solution). The HCl solution was added to the (36) (35.2 g, 0.111 moles), which after 15 minutes caused a thick white ppt to form. After an additional 45 minutes of stirring the white solid was filtered and washed with diethyl ether (3×100 ml). This solid was then stirred into 200 ml of 1:1 dioxane:water, and allowed to stir until the mixture became homogenous, approx. 1 hour. Water (100 mL) was added and the solution was extracted with ethyl acetate (2×200 ml). The organic layer was dried over MgSO₄, evaporated to afford a clear oil, which afforded (37) as a waxy white solid after drying overnight under high (31.3 g, 80.4%). (1H NMR CDCl₃) δ 7.42 (1H, d), 7.3–7.4 (6H, m) 6.80 (1H, d),5.32(1H, bd), 5.10(2H, dd,), 3.7(3H, s,), 3.6 (1H, bd). APCI MS M+23, No M+1. HPLC: 17.43 min. on C-18 column @ 1.5 ml/min. 20% CH3CN(0.1% TFA) in H2O(0.1% TFA)→90% CH3CN(0.1% TFA) in H2O(0.1% TFA) (0→22 min.)

Step (d): Preparation of methyl 2-[2-(benzyloxy)-5-bromophenyl]-2-oxoacetate

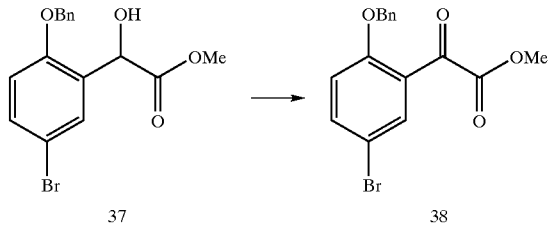

Methylene chloride (30 mL) was cooled to minus 70° C. under N₂ with stirring via dry ice/acetone bath, and then oxalyl chloride (3.07 ml, 0.035 moles) was added. DMSO (4.97 ml, 0.70 moles) was then added as a 1:1 mix with CH₂Cl₂ slowly down the side of the flask, not allowing the temperature to go above −60° C. This was stirred for 15 minutes, and then the alcohol (37) (10.26 g, 0.026 moles) was added as a solution in CH₂Cl₂, dropwise, again not allowing the temp. to climb above −60° C. This mixture was stirred at −65° C. for 30 minutes, then added Et₃N (20.40 ml, 0.145 moles) dropwise, not allowing temp. to reach −60° C. Upon warming to room temp., water (150 ml) was added and the product was extracted into ethylacetate. The organic phase was dried over MgSO₄, and then rotovaped to a pale yellow solid, (38) 10.03 g, 98% yield. (1H NMR CDCl₃) δ 7.99 (1H, d), 7.65 (1H, dd), 7.38–7.42 (5H, m), 6.96 (1H, d), 5.05 (2H, s), 3.35 (3H, s). APCI MS No M+1, M-91 (257). HPLC: 20.95 min. on C-18 column @ 1.5 ml/min. 20% CH3CN(0.1% TFA) in H2O(0.1% TFA)→90% CH3CN (0.1% TFA) in H2O(0.1% TFA) (0→22 min.)

Step (e): Preparation of Methyl (2R)-2-[2-(Benzyloxy)-5-bromophenyl]-2-hydroxyethanoate

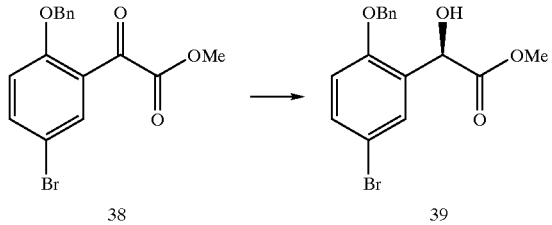

The ketoester (38) (12.9 g, 0.037 moles) was slurried in CH₂Cl₂ (6 mL), then R-Alpine Borane (14.07 ml, 0.052 moles) was added dropwise and the slurry allowed to stir at room temp. After 5 days an additional amount of R-Alpine Borane (10.1 ml, 0.037 moles) was added and the mixture was stirred for another 24 hours. Acetaldehyde (6.0 ml) was added together with CH₂Cl₂ (100 ml) and ethanolamine (4.0 ml), and then the mixture was stirred for 1 hour. The mixture was evaporated by ~50% and then columned directly on flash silica using 15→20% ethyl acetate in hexane to afford the desired product (39), 12.2 g 94% yield. (1H NMR CDCl₃) δ 7.42 (1H, d), 7.3–7.4 (6H, m) 6.80 (1H, d), 5.32 (1H, bd), 5.10 (2H, dd), 3.7(3H, s), 3.6 (1H, bd). APCI MS M+23, No M+1. HPLC: 17.43 min. on C-18 column @ 1.5 ml/min. 20% CH3CN(0.1% TFA) in H2O(0.1% TFA) →90% CH3CN(0.1% TFA) in H2O(0.1% TFA) (0→22 min.) Chiral HPLC 8.07 min. (95%ee) @ 2.0 ml/min. 20% EtOH (0.1% TEA) in Hexane on (Phenomenex) Chirex (R)-NGLY and DNB chiral column.

Step (f): Preparation of Methyl (2S)-2-[2-(Benzyloxy)-5-bromophenyl]-2-(2-nitrophenoxy)ethanoate

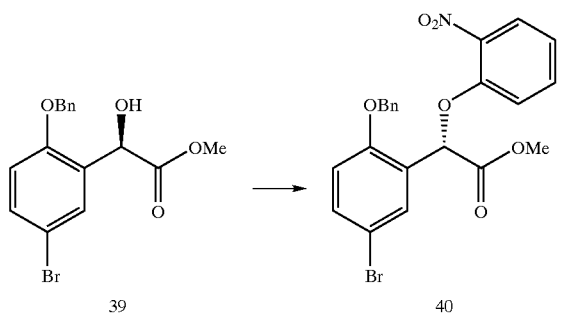

The chiral alcohol (39) (5.0 g, 0.014 moles) was dissolved in ethyl acetate (75 mL), then triphenyl phosphine (4.85 g, 0.018 moles) and o-nitro phenol (2.37 g, 0.017 moles) were added with stirring. The reaction was put under N₂ and cooled to -40° C. via dry ice/acetone bath, and the DIAD (3.63 ml, 0.018 moles) was added dropwise. The reaction was stirred at -40° C. for 2 hours. The volume was reduced by ~50% and the reaction was chromatographed on flash silica using 15%→20% ethyl acetate in hexane to afford desired product (40) (5.6 g, 83.3%). (1H NMR CDCl₃) δ 7.85 (1H, dd), 7.71 (1H, d), 7.3–7.45 (6H, m), 7.07 (1H, t), 7.0 (1H, d), 6.85 (1H, d), 6.20 (1H, s), 5.12 (2H, dd), 3.72 (3H, s). HPLC: 22.07 min. on C-18 column @ 1.5 ml/min. 20% CH3CN(0.1% TFA) in H2O(0.1% TFA)→90% CH3CN (0.1% TFA) in H2O(0.1% TFA) (0→22 min.) No separation of enantiomers on chrial HPLC.

Step (g): Preparation of (2S)-2-[2-(Benzyloxy)-5-bromophenyl]-2H-1,4-benzoxazin-3(4H)-one

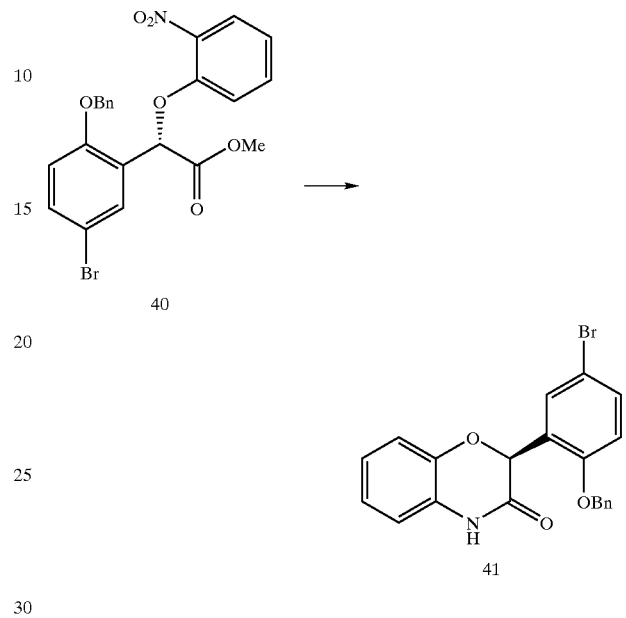

The chiral ether (40) (9.3 g, 0.020 moles) was dissolved in 400 ml MeOH and then 10 g of neutral RaNi was added (washed with water 10x. then MeOH 3x). The mixture was placed under H₂ at 53.8 psi. A pressure drop to 48.0 psi after 15 hrs was noted. The reaction was filtered and evaporated which after chromatography, on flash silica using 20% ethyl acetate in hexane, afforded the desired product (41) (5.17 g, 64%, and 92.8% ee via chiral HPLC). Variable results were obtained on attempts to improve the enantiomeric excess by recrystallisation from EtOAc. The filtrate typically contained material of enriched enantiomeric excess. Thus material was ultimately obtained of 95.5%ee. (1H NMR CDCl₃) δ 8.2 (1H, bs), 7.52 (1H, d), 7.42 (1H, dd), 7.33–7.42 (5H, m), 6.82–6.98 (4H, m), 6.68 (1H, d), 5.82 (1H, s) 5.02 (1H, dd) APCI MS M+1 (411). HPLC: 17.48 min. on C-18 column @ 1.5 ml/min. 20% CH3CN(0.1% TFA) in H2O (0.1% TFA)→90% CH3CN(0.1% TFA) in H2O(0.1% TFA) (0→22 min.). *Chiral HPLC* 6.12 min. (95.5%ee) @ 2.0 ml/min. 20% EtOH (0.1% TEA) in Hexane on (Phenomenex) Chirex (R)-NGLY and DNB chiral column.

Step (h): Preparation of 4-(Benzyloxy)-3-[(2S)-3-oxo-3,4-dihydro-2H-1,4-benzoxazin-2-yl]benzenecarbonitrile

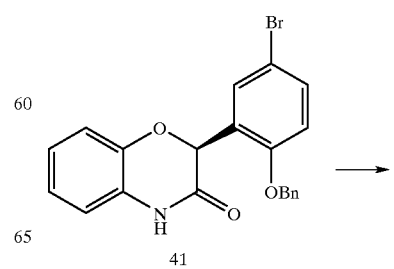

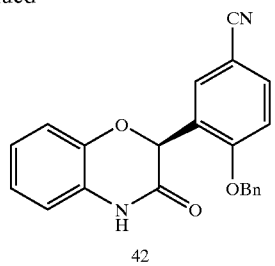

42

To (41) (4.15 g, 0.010 moles) in DMF (6 mL) was added CuCN (1.57 g, 0.18 moles) and the mixture heated to 160° C. with stirring under $N_2$ overnight. The reaction mixture was cooled to R.T. and then ethyl acetate (100 mL) was added. Washing with sat. brine/$NH_4OH$ (9:1) (2×130 ml), drying over $MgSO_4$, and then evaporation afforded a brown solid. A portion was crystallised from ethylacetate to afford (0.76 g) and the remainder was purified by chromatography 25%→50% ethyl acetate in hexane to afford another 1.53 g, (2.29 g, 63.6%). (1H NMR $CDCl_3$) δ 8.26 (1H, bs), 7.72 (1H, d), 7.65 (1H dd), 7.30 (5H, s), 7.03 (1H, d), 6.91–6.98 (3H, m), 6.72 (1H, dd), 5.86 (1H, s), 5.14 (2H, dd). APCI MS M+1 (357). HPLC: 17.80 min. on C-18 column @ 1.5 ml/min. 20% CH3CN(0.1% TFA) in H2O(0.1% TFA) →90% CH3CN(0.1% TFA) in H2O(0.1% TFA) (0→22 min.) Chiral HPLC 6.51 min. @ 2.0 ml/min. 20% EtOH (0.1% TEA) in Hexane on (Phenomenex) Chirex (R)-NGLY and DNB chiral column.

Step (i): Preparation of 4-(Benzyloxy)-3-[(2S)4-(5-bromopentyl)-3-oxo-3,4-dihydro-2H-1,4-benzoxazin-2-yl] benzenecarbonitrile

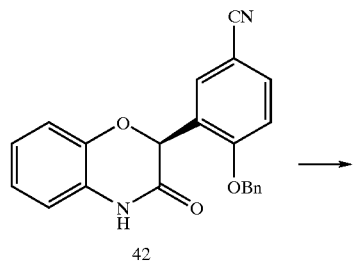

42

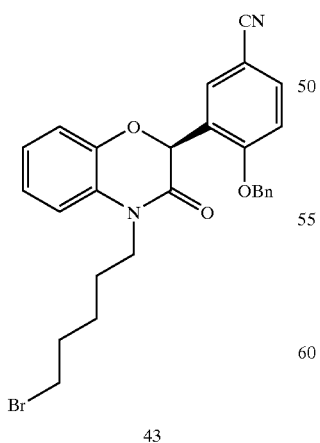

43

To (42) (2.2 g, 0.0062 moles) in dry DMF (15 mL) under $N_2$ with stirring was added dibromopentane (3.76 ml, 0.025 moles) and then the mixture was cooled too 0° C. KN(TMS)2 (11.11 ml 0.5M sol., 0.0055 moles) was added dropwise over ~15 minutes and the mixture was stirred for 1 h at 0° C., then at room temp for 2 hrs. Ethyl acetate (75 mL) was added and the mixture extracted with water (2×50 ml), dried the organic layer over $MgSO_4$ and rotovaped off solvent. Chromatography on flash silica to get afforded the required product (43) (1.51 g, 48%). (1H NMR $CDCl_3$) δ 7.65 (2H, d), 7.31 (5H, s), 6.94–7.07 (5H, m), 5.82 (1H, s), 5.14 (2H, dd), 3.89 (2H, dd), 3.37 (2H, t), 1.87 (2H, m), 1.58 (2H, m), 1.50 (2H, m,). APCI MS M+1 (505). HPLC: 23.01 min. on C-18 column @ 1.5 ml/min. 20% CH3CN(0.1% TFA) in H2O(0.1% TFA)→90% CH3CN(0.1% TFA) in H2O(0.1% TFA) (0→22 min.)

Step (j): Preparation of 4-(Benzyloxy)-3-[(2S)-4-(5-iodopentyl)-3-oxo-3,4-dihydro-2H-1,4-benzoxazin-2-yl] benzenecarbonitrile

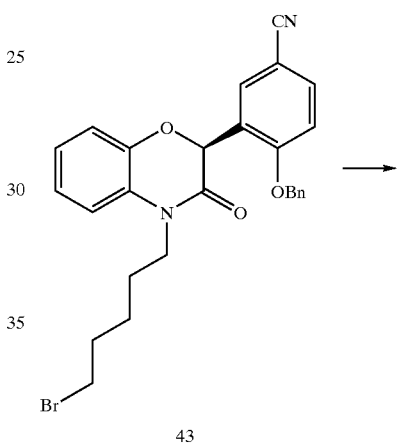

43

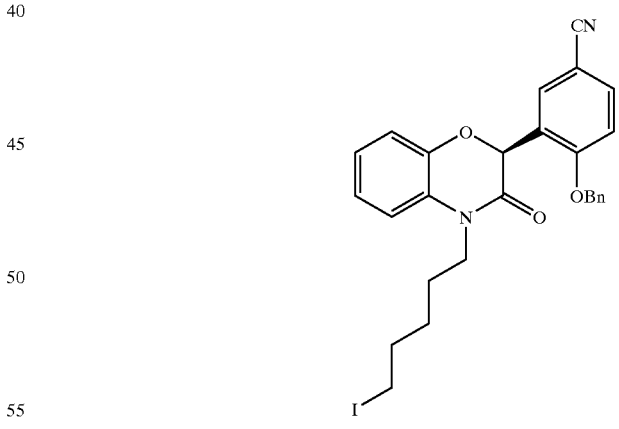

44

To (43) (1.49 g, 0.0029 moles) in acetone (20 ml) and added the NaI (2.21 g, 0.015 moles) and then the mixture was refluxed for 1 hour, filtered, rotovaped off acetone, slurried up in 30 ml ethyl acetate and washed with 30 ml $H_2O$, then 30 ml sat NaCl, dried the organic layer over $MgSO_4$ and rotovaped to a yellow oil (44), 1.48 g crude. (1H NMR $CDCl_3$) δ 7.63 (2H, d), 7.31 (5H, s), 6.93–7.10 (5H, m,) 5.81

(1H, s), 5.15 (2H, dd,), 3.88 (2H, t), 3.15 (2H, t), 1.82 (2H, m), 1.60 (2H, m), 1.45 (2H, m). APCI MS M+1 (553). HPLC: 23.54 min. on C-18 column @ 1.5 ml/min. 20% CH3CN(0.1% TFA) in H2O(0.1% TFA)→90% CH3CN (0.1% TFA) in H2O(0.1% TFA) (0→22 min.)

Step (k): Preparation of 4-(Benzyloxy)-3-((2S)-4-5-[(2R, 6S)-2,6-dimethyltetrahydro-1(2H)-pyridinyl]pentyl-3-oxo-3,4-dihydro-2H-1,4-benzoxazin-2-yl)benzenecarbonitrile

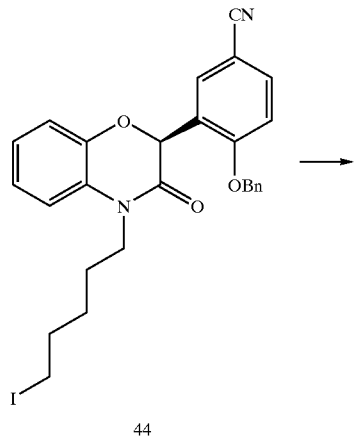

44

Step (1): Preparation of 4-(Benzyloxy)-3-((2S)-4-5-[(2R, 6S)-2,6-dimethyltetrahydro-1(2H)-pyridinyl]pentyl-3-oxo-3,4-dihydro-2H-1,4-benzoxazin-2-yl)-N-hydroxybenzenecarboximidamide

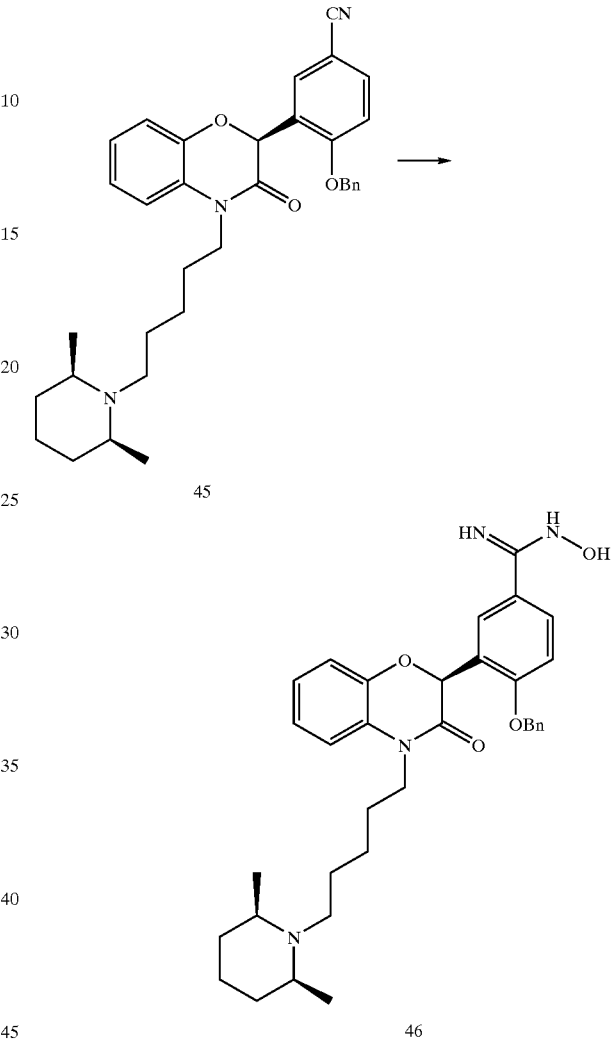

45

46

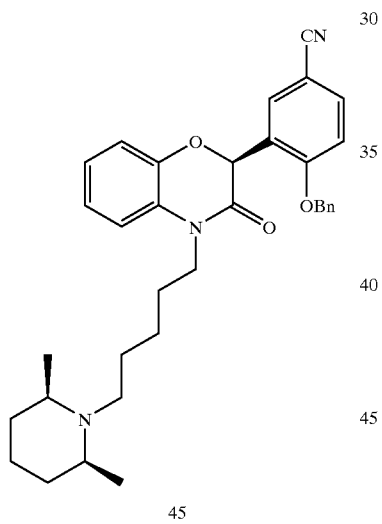

45

To (44) in dry DMF (2 mL) was added cis-2,6 dimethylpiperidine (2 mL) and the mixture stirred at room temp. overnight. Added 30 ml ethyl acetate and washed with H₂O (2×30 ml), dried the organic layer over MgSO₄ and rotovaped to a pale yellow oil, 1.27 g, 80.4% yield over 2 steps. Used without purification in next reaction. (1H NMR) δ 7.61–7.64 (2H, m), 7.31 (5H, s), 6.95–7.06 (5H, m), 5.84 (1H, s), 5.14 (2H, m), 3.88 (2H, m), 2.68–2.73 (2H, m), 2.43 (2H, m), 1.21–1.76 (12H, m), 1.04–1.10 (6H, m) APCI MS M+1 (538). HPLC: 14.95 min. on C-18 column @ 1.5 ml/min. 20% CH3CN(0.1% TFA) in H2O(0.1% TFA) →90% CH3CN(0.1% TFA) in H2O(0.1% TFA) (0→22 min.)

To (45) (0.5 g, 0.001 moles) in 5 ml MeOH was added hydroxylamine HCl (0.208 g, 0.003 moles), then diisopropylethylamine (0.348 ml, 0.002 moles) was added dropwise and the reaction stired overnight at room temp. Rotovaped off MeOH, added 50 ml CH₂Cl₂ and washed with sat. NaHCO₃, dried the organic layer over MgSO4 and rotovaped to a white waxy solid (46), 0.560 mg crude. Used without purification in next reaction. (1H NMR) δ 7.46–7.53 (2H, m), 7.20–7.27 (5H, m), 6.85δ6.94 (5H, m), 5.85 (1H, s), 5.03 (2H, s), 3.87–3.95 (1H, m), 3.71–3.78 (1H, m), 2.71–2.74 (2H, m), 2.47 (2H, bm), 1.19–1,64 (12H, m), 0.98–1.09 (6H, m). APCI MS M+1 (571). HPLC: 11.14 min. on C-18 column @ 1.5 ml/min. 20% CH3CN(0.1% TFA) in H2O(0.1% TFA)→90% CH3CN(0.1% TFA) in H2O(0.1% TFA) (0→22 min.)

79

Step (m): Preparation of 3-((2S)-4-5-[(2R,6S)-2,6-Dimethyltetrahydro-1(2H)-pyridinyl]pentyl-3-oxo-3,4-dihydro-2H-1,4-benzoxazin-2-yl)-4-hydroxybenzenecarboximidamide

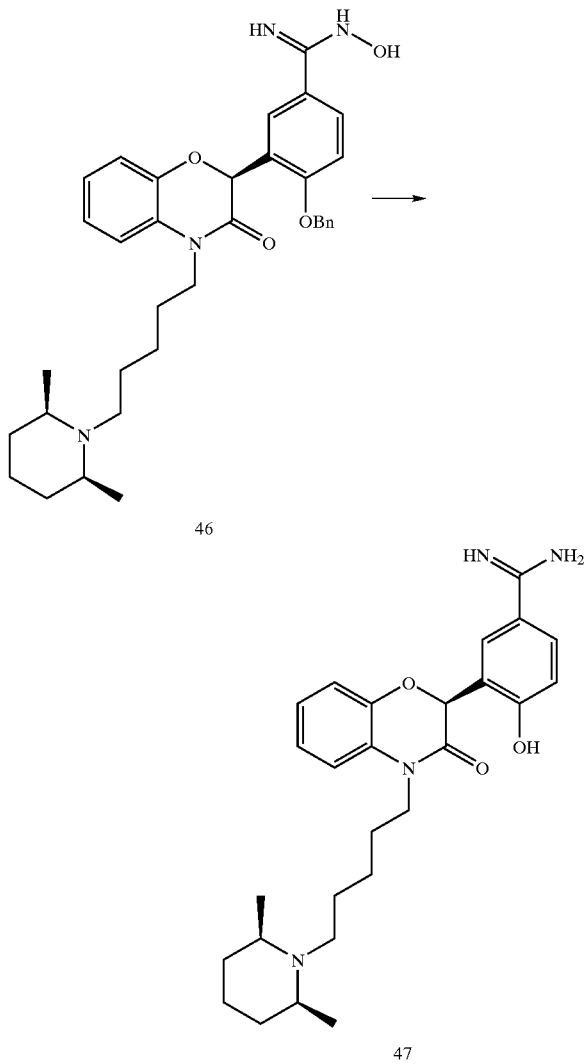

46

47

To (46) (0.50 g, 0.00087 moles) in TFA (2 mL) was added 4 ml TFAA (4 mL) and the mixture stirred at room temperature, under N$_2$, overnight. Rotovaped off the solvent to get a gray oil. Added TFA (5 mL), then added 0.060 g 20% Pd/C, evacuated the flask, filled with H$_2$ (via balloon), repeated, and let stir under an atmosphere of H$_2$ overnight. Filtered the reaction through celite, washed with CH$_2$Cl$_2$ then rotovaped off the solvent. Chromatographed on prep HPLC. Converted the clean fractions to the HCl salt by running through IRA 400(Cl) resin as an aqueous solution. Lyophilized to get 0.060 g desired product (47). (1H NMR-D$_2$O) δ 7.60–7.65 (2H, m,), 7.18 (1H, d), 6.97–7.07 (3H, m), 6.90 (1H, d), 5.70 (1H, s), 4.07–4.12 (1H, m), 3.80–3.85 (1H, m), 1.24–1.77 (12H, m), 1.07–1.14 (6H, m). APCI MS M+1 (465). HPLC: 8.31 min. on C-18 column @ 1.5 ml/min. 20% CH3CN(0.1% TFA) in H2O(0.1% TFA) →90% CH3CN(0.1% TFA) in H2O(0.1% TFA) (0→22 min.) Chiral HPLC 11.10 min. (90% ee) @ 1.0 ml/min. 20% EtOH, 20% MeOH(0.1 mM NH4Ac), 60% hexane on (Phenomenex) Chirex (R)-NGLY and DNB chiral column.

80

Intermediates 2-(3-Cyanophenyl)-3,4-dihydro-2H-1,4-benzoxazin-3-one

Step (a): Preparation of 2-[(3-Cyanophenyl)methylene]malononitrile

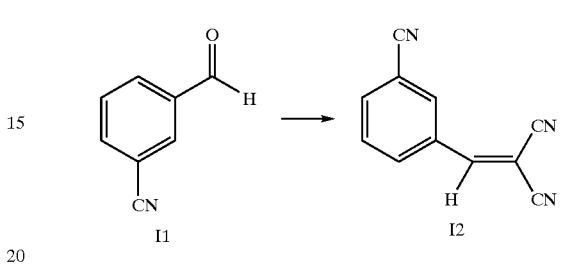

I1          I2

Into a mixture of 3-cyanobenaldehyde (I1) (24.8 g, 0.189 mol) and malononitrile (11.9 mL, 0.189 mol) in dioxane (120 mL) was added piperidine (1.5 mL) slowly. The solution was stirred at room temperature for 1 hour. The precipitate was filtered, washed with water, and dried in the high vacuum oven to give 7.11 g (21%) of product (I2) as yellow solid. To the filtrate was added ethanol and water and 10.29 g (30%) of additional product crystallized as yellow solid.

$^1$H NMR (CDCl$_3$, 300 MHz). δ 8.17 (1H, m), 8.51 (1H, m), 7.87 (2H, m), 7.68 (1H, m).

Step (b): Preparation of 3-(3-Cyanophenyl)-2,2-oxiranedicarbonitrile

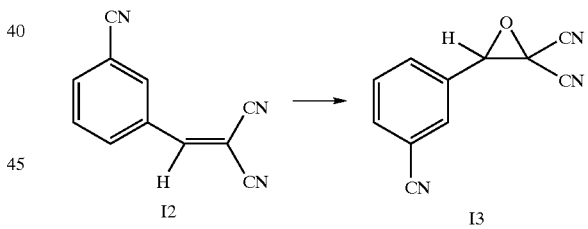

I2          I3

In a three-necked flask, intermediate (I2) (17.38 g, 97.0 mmol) was dissolved in acetonitrile (90 mL) and THF (113 mL) at room temperature with vigorous stirring. Sodium hypochlorite (183 mL) was added dropwise, while the pH of the solution was maintained between 4.5 and 6 throughout the addition by adding 2N sulfuric acid (20 mL). Once the addition was complete, stirring was continued for 20 minutes. Ethyl acetate was added, and the layers were separated. The aqueous layer was extracted with ethyl acetate (3×300 mL). The combined organic extracts were washed with brine (2×100 mL), dried with magnesium sulfate, filtered, and evaporated in vacuo. The residue was flushed through a pad of silica gel eluting with 50% ethyl acetate in hexane. The product (I3) was isolated 11.18 g (58%) as a tan solid.

$^1$H NMR (CDCl$_3$, 300 MHz): δ 7.83 (1H, m), 7.76 (1H, m), 7.67 (2H, m), 4.78 (1H, s).

Step (c): Preparation of 2-Bromo-2-(3-cyanophenyl)acetic Acid

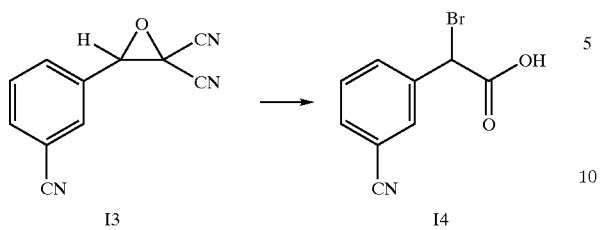

To the epoxide (I3) (5.12 g, 26.2 mmol) in THF (30 mL) was added 48% HBr (4.4 mL), and the solution was refluxed for 3 hours. The THF was removed in vacuo, and the residue was dissolved in ether (200 mL). The acid is extracted from ether with 1N NaOH (100 mL). The aqueous solution was then acidified with HCl, and the acid is extracted with ether (2×200 mL). The combined organic phases were dried over magnesium sulfate, filtered, evaporated in vacuo, and dried under high vacuum to give 4.32 g (69%) of (I4) as a brown oil.

$^1$H NMR (CDCl$_3$, 300 MHz): δ 7.83 (1H, m), 7.73 (1H, m), 7.55 (1H, m), 7.41 (1H, m), 5.26 (1H, s).

Step (d): Preparation of 2-Bromo-2-(3-cyanophenyl)acetyl Chloride

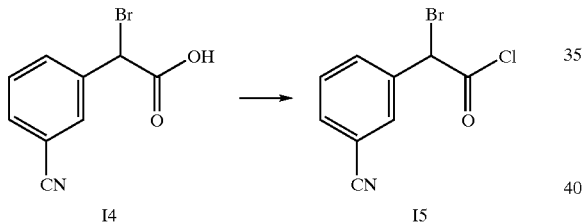

To the acid (I4) (1.01 g, 4.21 mmol) in dichloromethane (12 mL) were added oxalyl chloride (1 equiv.) and a catalytic amount of DMF (0.1 mL). Bubbling occurred and the resulting solution was stirred for 1 hour. The solvent was removed in vacuo to give (I5) in quantitative yield as a brown oil.

$^1$H NMR (CDCl$_3$, 300 MHz): δ 7.80–7.72 (3H, m), 7.592 (1H, m), 5.64 (1H, s).

Step (e): Preparation of N1-(2-Hydroxyphenyl)-2-bromo-2-(3-cyanophenyl)acetamide

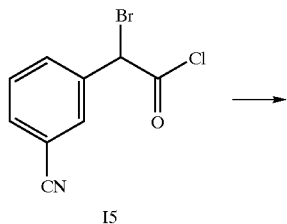

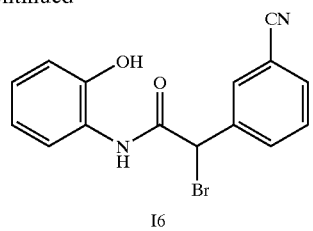

To (I5) (1.08 g, 4.17 mmol) in dichloromethane (10 mL) were added o-aminophenol hydrochloride (0.62 g, 4.26 mmol) and diisopropylethylamine (0.72 mL, 4.11 mmol). The solution was stirred at room temperature for 4 hours. The solution was diluted with water and extracted with ethyl acetate (5×100 mL). The combined organic extracts were washed with brine (200 mL), dried with magnesium sulfate, filtered, and evaporated in vacuo to give (I6) in quantitative yield as a brown oil.

Step (f): Preparation of 2-(3-Cyanophenyl)-3,4-dihydro-2H-1,4-benzoxazin-3-one

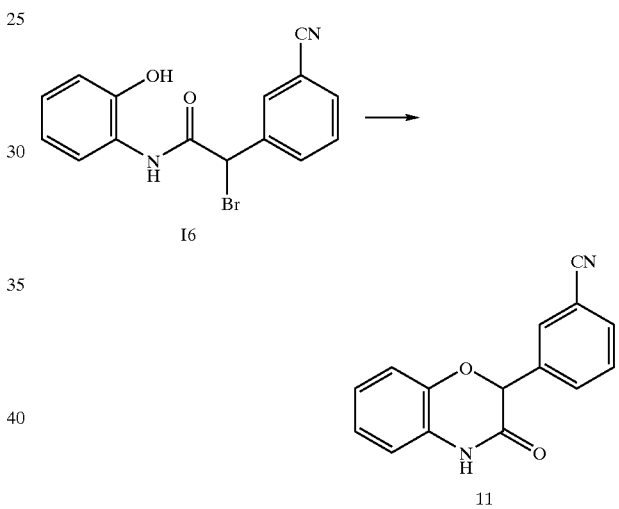

To the benzoxazinone (I6) (1.38 g, 4.17 mmol) in DMF (5 mL) was added potassium carbonate (1.40 g, 10.1 mmol), and the solution was stirred at room temperature for 1 hour. The solution was diluted with water and extracted with ethyl acetate (3×150 mL). The combined organic extracts were washed with brine (2×100 mL), dried with magnesium sulfate filtered, and evaporated in vacuo. The residue was purified on a silica gel column eluted with 25% ethyl acetate in dichloromethane. The product (I1) was isolated 0.48 g (46%) as a light orange solid.

$^1$H NMR (CDCl$_3$, 300 MHz): δ 7.99 (1H, s), 7.75 (2H, m), 7.64 (1H, m), 7.49 (1H, m), 7.11–6.97 (3H, m), 6.80 (1H, m), 5.69 (1H, s).

Alternative Procedure for Preparation of 2-(3-Cyanophenyl)-3,4-dihydro-2H-1,4-benzoxazin-3-one In a similar manner to steps (a) through (f) described above, but starting from 3-bromobenzaldehyde, 2-(3-bromophenyl)-3,4-dihydro-2H-1,4-benzoxazin-3-one may be prepared.

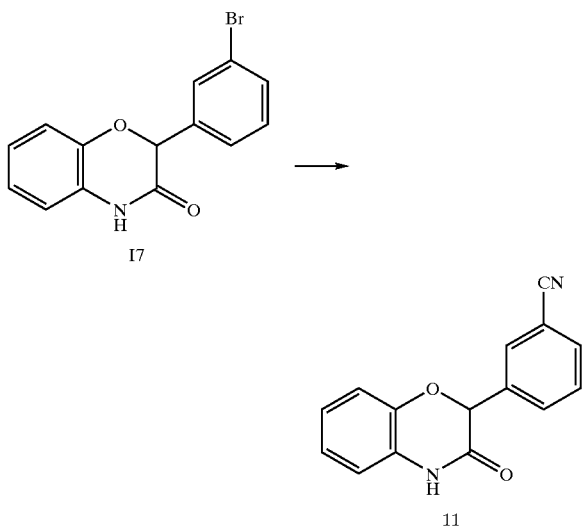

To a solution of 2-(3-bromophenyl)-3,4-dihydro-2H-1,4-benzoxazin-3-one (I7) (3.00 g, 9.87 mmol) in DMF (20 mL) was added Zinc cyanide (0.68 g, 5.79 mmol) and then tetrakistriphenylphosphine palladium (0) (0.96 g, 8 mol %). The degassed solution was heated at 100° C. for 5 hours, cooled to room temperature, and then treated with water (50 mL). The product was extracted into ethyl acetate (2×100 mL), washed with brine (50 mL), dried over MgSO$_4$, and then purified by silica gel chromatography, eluant 50% ethyl acetate in hexane. This process affords the title compound (1.866 g, 76%) that was recrystallized from ethanol/water.

(APCI MS) 251.

Analysis C$_{15}$H$_{10}$N$_2$O$_2$: Required: C, 71.99; H, 4.03; N, 11.19. Found: C, 71.59; H, 4.22; N, 10.96.

Procedure for Preparing Methyl 2-Bromo-2-(3-bromophenyl)acetate

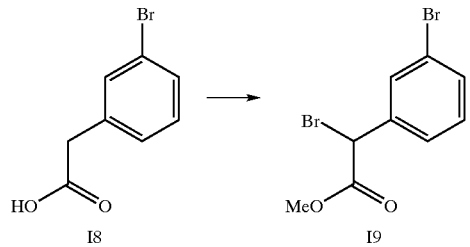

To 3-bromophenylacetic acid (10 g, 47 mmol) under argon was added PBr$_3$ (11.2 mL, 118 mmol) and the suspension stirred at room temperature for 45 minutes. Bromine (11.1 mL, 216 mmol) was added dropwise over 5 minutes. The mixture was stirred at 100° C. for 3 hours and then cooled. Anhydrous methanol (35 mL) was added dropwise over 30 minutes, and then the reaction mixture was diluted with ether (400 mL), washed with 5% NaHCO$_3$ (800 mL), brine (200 mL), and then dried over MgSO$_4$. The mixture was filtered and concentrated in vacuo to afford material of sufficient purity to use directly.

Alternative Procedure for Preparing 2-(5-Bromo-2-methoxyphenyl)-2H-1,4-benzoxazin-3(4H)-one

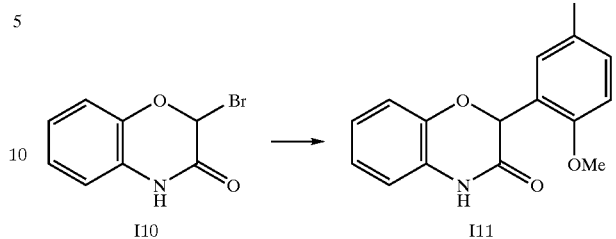

To 2-bromo-2H-1,4-benzoxazin-3(4H)-one (I10) (1.40 g, 6.14 mmoles) in methylene chloride (20 mL) was added 4-bromoanisole and then tin (IV) chloride. Addition of tin (IV) chloride caused a brown solution to form. The solution was refluxed for 5 hours, diluted with methylene chloride (100 mL) and washed with water (2×50 mL). After drying over Magnesium sulphate the mixture was concentrated until the product (I11) precipitated (0.58 g). Concentration of the mother liquors and chromatography on silica gel afforded an additional amount of product (I11) (0.55 g).

(APCI MS) 334

Preparation of 4-Methoxy-3-(3-oxo-3,4-dihydro-2H-1,4-benzoxazin-2-yl)benzenecarbonitrile

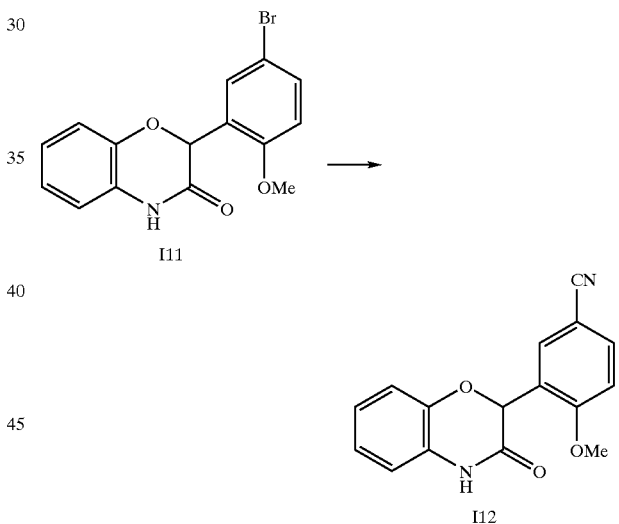

To a solution of 2-(5-bromo-2-methoxyphenyl)-2H-1,4-benzoxazin-3(4H)-one (I11) (0.90 g, 2.70 mmoles) in DMF (10 mL) was added copper (I) cyanide (1.3 g, 5 equiv.) and the mixture heated at 160° C. for 12 hours. The mixture was cooled and methylene chloride (100 mL) and aqueous ammonium hydroxide (10 mL) were added. The methylene chloride layer was separated and dried over MgSO$_4$ which afforded the required product (I12) (0.67 g, 89%) upon evaporation in vacuo.

(APCI MS) 281

The invention compounds have demonstrated factor Xa, thrombin, and factor VIIa inhibitory activity in the standard assays commonly employed by those skilled in the art.

Determination of Factor Xa IC$_{50}$ and K$_i$ Constants

The ability of compounds to act as inhibitors of human factor Xa catalytic activity is assessed by determination of that concentration of test substance that inhibits by 50% (IC$_{50}$) the ability of human factor Xa to cleave the chromogenic substrate S2765 (N-CBz-D-Arg-L-Gly-L-Arg-p-nitroanilide. 2HCl, DiaPharma). Typically, 145 μL human factor Xa (1 nM final, Enzyme Research Laboratories) in 10 mM HEPES, 150 mM NaCl, 0.1% BSA, pH 7.4 (HBSA buffer), and 5 μL of test substance in DMSO (2% final) are incubated for 60 minutes at room temperature. Following preheating to 37° C. for 5 minutes, to this mixture is added 100 μL of S2765 (400 μM final) in HBSA buffer. The velocity of S2765 hydrolysis is determined at 37° C. by measuring the initial rate of change of the optical density at OD$_{405}$ nM every 10 seconds for 5 minutes using a ThermoMax® Kinetic Microplate Reader.

For K$_i$ determinations, the assay conditions were essentially the same as above except for the following. The concentration of factor Xa was 50 pM, and that of the substrate, in this case a fluorogenic S2765 (i.e. S2765 with AMC tag instead of pNA, California Peptide Research), was over the range of 10 to 500 μM. The test compound and substrate in HBSA buffer were incubated as above, and the reaction was initiated with enzyme-buffer. The data (steady-state velocity at various concentrations of the substrate and the inhibitors) of the competitive inhibition was analyzed using the methods described by Segel (Enzyme Kinetics, Wiley Interscience Publications, 1993). A non-linear regression program, Kaleidograph and/or Microsoft Excel, was used to estimate the kinetic parameters (K$_m$, V$_{max}$, and K$_i$) by use of Michaelis-Menten and reciprocal Dixon plot fits.

Determination of Thrombin IC$_{50}$ and K$_i$ Constants

The ability of compounds to act as inhibitors of human thrombin catalytic activity is assessed by determination of that concentration of test substance that inhibits by 50% (IC$_{50}$) the ability of human thrombin to cleave the chromogenic substrate Chromozym TH (Tosyl-Gly-Pro-Arg-pNA*Ac, Boehringer Mannheim). Typically, 145 μL human thrombin (0.75 nM, Enzyme Research Laboratories) in a HPB buffer (10 mM HEPES, 100 mM NaCl, 0.05% BSA, 0.1% PEG-8000, pH 7.4) and 5 μL of test substance in DMSO (2% final) are incubated for 60 minutes at room temperature. Following preheating to 37° C. for 5 minutes, to this mixture is added 100 μL of Chromozym TH (24 μM final) in HPB buffer. The velocity of Chromozym TH hydrolysis is determined at 37° C. by measuring the initial rate of change of the optical density at OD 405 nM every 10 seconds for 5 minutes using a ThermoMax® Kinetic Microplate Reader.

For K$_i$ determinations, the assay conditions were essentially the same as the aforementioned except for the following. The concentration of thrombin used was 50 pM, and that of a fluorogenic Chromozym TH (i.e., Chromozym TH with AMC instead of pNA tag, Novabiochem) was over the range of 1 to 40 μM. The test compound and substrate in HPB buffer were incubated as above, and the reaction was initiated with enzyme-buffer and run at 24° C. Kinetic analysis was performed as for factor Xa K$_i$ determinations.

Determination of Trypsin IC$_{50}$ and K$_i$ Constants.

The ability of compounds to act as inhibitors of human trypsin catalytic activity is assessed by determination of that concentration of test substance that inhibits by 50% (IC$_{50}$) the ability of human trypsin to cleave the chromogenic substrate S2222 (N-Bz-L-Ile-L-Glu-L-Gly-L-Arg-p-nitroanilide. HCl, DiaPharma). Typically, 145 μL human trypsin (0.5 nM final) in 10 mM HEPES, 150 mM NaCl, 0.1% BSA, and 5 μL of the test substance in DMSO (2% final) are incubated for 60 minutes at room temperature. Following preheating to 37° C. for 5 minutes, to this mixture is added 100 μL of S2222 in HBSA buffer (100 μM final), and the velocity of S2222 hydrolysis is determined at 37° C. by measuring the optical density at OD 405 nM every 10 seconds over 5 minutes using a ThermoMax® Kinetic Microplate Reader.

For K$_i$ determinations, the assay conditions were essentially the same as the aforementioned except that the reaction was initiated with enzyme-buffer and run at 24° C. using a substrate range of 10 to 500 μM. Kinetic analysis was performed as for factor Xa K$_i$ determinations.

Determination of Tissue Factor/Factor VIIa IC$_{50}$

The ability of compounds to act as inhibitors of the catalytic activity of human tissue factor/factor VIIa complex is assessed by determination of that concentration of test substance that inhibits by 50% (IC$_{50}$ the ability of a complex of human recombinant tissue factor/factor VIIa to cleave the chromogenic substrate Spectrozyme VIIa (CH$_3$SO$_2$-D-CHA-Arg-pNA*AcOH, American Diagnostica). Typically, 50 μL human factor VIIa (Enzyme Research Laboratories) is incubated for 10 minutes as a 1:1 mixture (5 nM final each) with 95 μL recombinant human tissue factor (American Diagnostica) in a modified HBSA buffer (10 mM Hepes, 5 mM CaCl$_2$, 0.1% BSA, pH 8.0). Then 5 μL of the test substance in DMSO (2% final) is added and incubated for 60 minutes at room temperature. Following preheating to 37° C. for 5 minutes, to this mixture is added 100 μL of Spectrozyme VIIa (500 μM final) in modified HBSA, and the velocity of Spectrozyme VIIa hydrolysis is determined at 37° C. by measuring the optical density at an OD$_{405}$ nM every 10 seconds over 5 minutes using a ThermoMax® Kinetic Microplate Reader.

In Vitro Assay for Human Prothrombinase

This assay demonstrates the ability of test compounds of the invention to inhibit the human prothrombinase (PTase) complex (typically comprising of human factor Va, human factor Xa, Ca$^{2+}$, and phospholipid moiety) and thereby the subsequent cleavage of prothrombin to yield thrombin. For determination of IC$_{50}$ (PTase) of the compounds of the invention, PTase activity was expressed by thrombin activity.

PTase reaction was performed in 100 μL of mixture containing PTase (20 μM) PCPS (Avanti Polar Lipids following a procedure modified from Barenholz et al., Biochemistry, 1977;16:2806–2810) in a 30:70 ratio, 2.5 nM human factor Va (Enzyme Research Laboratories) and 2.5 pM human factor Xa (Enzyme Research Laboratories) in modified HEPES buffer (10 mM Hepes, 150 mM NaCl, 0.1% PEG-8000, 0.05% BSA, 2.5 mM CaCl$_2$, pH 7.4), 3 μM human prothrombin (Enzyme Research Laboratories) and varied concentrations of the test compounds (1 nM to 100 μM in DMSO, 2% final). Reaction was started by co-incubating PTase with test compound for 60 minutes at room temperature, followed by addition of prothrombin for 6 minutes at room temperature. Next, the reaction was quenched by the addition of 100 μL of 20 mM EDTA. Activity of the thrombin (product) is then measured in the presence of 50 μL S2238 (250 μM final, H-D-Phe-Pip-Arg-pNA*Ac, DiaPharma) as substrate by measuring the change at 37° C. in OD$_{405}$ nM for 5 minutes at 10 second intervals using a ThermoMax® Kinetic Microplate Reader.

Example 5 in this assay has an IC50 of 0.00017 uM

Determination of Prothrombin Time (PT)

Rat, rabbit, dog, and human blood (typically 1.8 mL) was collected and added to a sodium citrate solution (3.8%) to afford a 1:10 dilution. After centrifugation (2000 g for 10 minutes), the blood plasma was stored at −70° C. to 0° C. Conventional prothrombin time (PT) tests were carried out in the presence of various concentrations of test compound and the concentration of test compound required to double the clotting time determined. Typically, the test compound (50 μL volume of varying concentrations 0.1 μM to 1000 μM) and blood plasma (100 μL volume) were incubated at 37° C. for 10 minutes, and then tissue thromboplastin, typically Neoplastine from American Bioproducts, with calcium was added. Fibrin formation and the time required for a clot to form were determined using an automated ST4 Clot Detection System in duplicate.

In an ex-vivo modification of this assay, drug was administered intravenously or orally to a group of rats or rabbits. At various times blood samples were collected, and the PT coagulation assay as described above were performed.

Arterio-Venous Shunt Stasis Antithrombotic Model

In vivo measurements of antithrombotic activity were performed according to the procedure of Vogel et al., *Thromb. Res.*, 1989;54:399–410. Briefly, the vena cava was exposed. collateral veins were ligated, and sutures were loosely located around the inferior vena cava. These sutures were tightened after drug administration to induce stasis within the ligated portion of the vena cava. After an appropriate time, the thrombus was isolated and weighed. The effect of varying drug concentrations administered intravenously or orally on thrombus mass reflected antithrombotic activity.

Alternatively, and according to the procedure of Smith et al., *Br. J. Pharmacol.*, 1982;77:29–38, the left jugular and right carotid artery were exposed and cannulated. A shunt, which contains silk threads or preweighed cotton, is then inserted which connects the two cannulated vessels. Once drug has been administered, the shunt is closed, and the thrombus that forms on the foreign surface in the shunt is removed after a period of time. Clot weight then reflects antithrombotic activity.

Arterial Thrombosis Model

FeCl$_3$ Induced Carotid Arterial Injury Model

The FeCl$_3$ induced injury to the carotid artery in rats was induced according to the method described by Kurz K. D., Main R. W., Sandusky G. E., *Thrombosis Research*, 1990;60:269–280 and Schumacher W. A. et al., *J. Pharmacology and Experimental Therapeutics*, 1993;267:1237–1242.

Male, Sprague-Dawley rats (375–410 g) were anesthetized with urethane (1500 mg\kg ip). Animals were laid on a 37° C. heating pad. The carotid artery was exposed through a midline cervical incision. Careful blunt dissection was used to isolate the vessel from the carotid sheath. Using forceps, the artery was lifted to provide sufficient clearance to insert two small pieces of polyethylene tubing (PE-205) underneath it. A temperature probe (Physitemp MT23/3) was placed between one of the pieces of tubing and the artery. Injury was induced by topical application on the carotid artery above the temperature probe of a small disc (3 mm dia.) of Whatman No. 1 filter paper previously dipped in a 35% solution of FeCl$_3$. The incision area was covered with aluminum foil in order to protect the FeCl$_3$ from degradation by light. The vessel temperature was monitored for 60 minutes after application of FeCl$_3$ as an indication of blood flow. Vessel temperature changes were recorded on a thermistor (Cole-Palmer Model 08533-41).

The time between the FeCl$_3$ application and the time at which the vessel temperature decreased abruptly (>2.4° C.) was recorded as the time to occlusion of the vessel. The fold shift in mean occlusion time (MOT), therefore, refers to the time to occlusion in drug treated animal divided by control time to occlusion. Inhibitor compounds were given as an IV bolus (0.75 mg/kg) followed immediately by an IV infusion (50 μg/kg/min via femoral vein).

| Structure | Name | Thrombin IC$_{50}$ μM | Trypsin IC$_{50}$ μM | Xa IC$_{50}$ μM | VIIa % inhib. @ 100 μM |
|---|---|---|---|---|---|
| 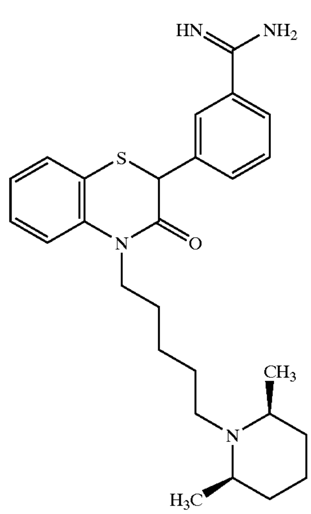 | 3-(4,5-[(2R, 6S)-2,6-Dimethyltetrahydro-1(2H)-pyridinyl]-pentyl-3-oxo-3,4-dihydro-2H-1,4-benzothiazin-2-yl)-benzenecarboximidamide (Example 3) | 1.78 | 0.782 | 0.108 | 31 |

-continued

| Structure | Name | Thrombin IC$_{50}$ μM | Trypsin IC$_{50}$ μM | Xa IC$_{50}$ μM | VIIa % inhib. @ 100 μM |
|---|---|---|---|---|---|
| 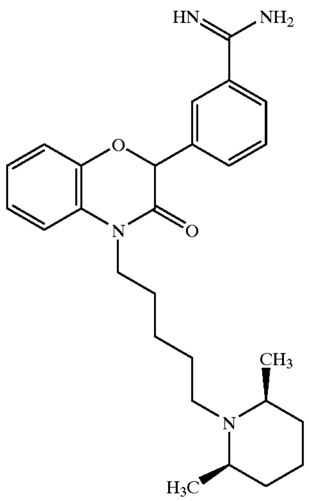 | 3-(4-5-[(2R, 6S)-2,6-Dimethyltetrahydro-1(2H)-pyridinyl]pentyl-3-oxo-3,4-dihydro-2H-1,4-benzoxazin-2-yl)-benzenecarboximidamide (Example 2) | 2.020 | 0.474 | 0.007 | 30 |
| 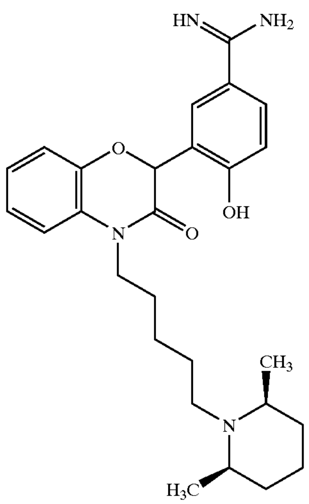 | 3-(4-5-[(2R, 6S)-2,6-dimethyltetrahydro-1(2H)-pyridinyl]pentyl-3-oxo-3,4-dihydro-2H-1,4-benzoxazin-2-yl)-4-hydroxybenzene-carboximidamide (Example 5) | 1.03 | 0.38 | <0.001 | 29 |
| 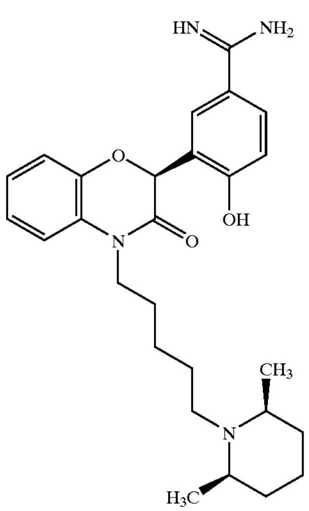 | 3-((2S)-4-5-[(2R, 6S)-2,6-dimethyltetrahydro-1(2H)-pyridinyl]pentyl-3-oxo-3,4-dihydro-2H-1,4-benzoxazin-2-yl)-4-hydroxybenzene-carboximidamide (Example 6) | 1.39 | 0.75 | 0.003 (Ki 0.076 nM) | 37 |

Biological Data of Examples 2 and 5

In Vitro Diluted Prothrombin Time (dPT) Assay

The effects of Examples 2 and 5 on dPT were evaluated using pooled plasma from rabbits, dogs, and human volunteers. Both compounds concentration-dependently prolonged dPT and displayed a similar potency in rabbit and dog plasma. In human plasma, however, Example 5 was more potent than Example 2 by approximately one order of magnitude. The concentrations which caused 5-fold prolongation of dPT for Examples 2 and 5 were 1.1 and 0.97 $\mu$M in rabbit plasma, 1.8 and 1.2 $\mu$M in dog plasma, and 0.53 and 0.063 $\mu$M in human plasma, respectively.

| In Vitro Diluted Prothrombin Time (dPT) Assay | | | |
|---|---|---|---|
| | 2X | 5X | 10X |
| Rabbit | | | |
| DX-9065a ($\mu$M) | 1.4 | 21.8 | 96.8 |
| Example 2 ($\mu$M) | 0.33 | 1.1 | 2.4 |
| Example 5 ($\mu$M) | 0.44 | 0.97 | 1.86 |
| Dog | | | |
| DX-9065a ($\mu$M) | 2.5 | 51.1 | 118.6 |
| Example 2 ($\mu$M) | 0.57 | 1.8 | 4.9 |
| Example 5 ($\mu$M) | 0.84 | 1.2 | 1.81 |
| Human | | | |
| DX-9065a ($\mu$M) | 0.06 | 0.53 | 1.3 |
| Example 2 ($\mu$M) | 0.17 | 0.53 | 1.2 |
| Example 5 ($\mu$M) | 0.0069 | 0.063 | 0.157 |

The data is the concentrations that cause 2-, 5-, and 10-fold prolongation of baseline values of dPT.
DX-9065a is a reference factor Xa inhibitor The effects of Example 2 on thrombosis and hemostasis has been studied in a rabbit veno-venous shunt model of thrombosis. In that model, a plastic shunt which contains cotton thread was inserted into abdominal vena cava and thrombus developed inside the shunt under control conditions. The end points of the experiment are the time to occlusion (TTO) and thrombus weight. Example 2 was given to the rabbit via jugular vein as a single bolus followed by constant infusion for 140 minutes. Three doses have been tested in a total of 15 rabbits (5 rabbits in each group): 30 $\mu$g/kg+1 $\mu$g/kg/min, 60 $\mu$g/kg+2 $\mu$g/kg/min, and 90 $\mu$g/kg+3 $\mu$g/kg/min. Example 2 dose-dependently prolonged the time to occlusion and reduced the net thrombus weight. In the highest dose group, T7o was increased from 16.8±5.4 minutes under control condition to 98.2±21.8 minutes with no occlusive thrombus formation during the 120-minute test period in 4 out of 5 animals. The net thrombus weight was reduced from 56.4±4.3 to 21.3±7.8 mg in that group. Example 2, at the highest dose, prolonged aPTT, TT, PT, and bleeding time by 5.4-, 1.5-, 1.8-, and 2.5-fold, respectively. In contrast, there were only slight increases for ACT in all 3 groups.

The foregoing biological tests have been used to establish the compounds of this invention are useful for preventing and treating thrombotic disorders, for example venous thrombosis, deep vein thrombosis, thrombophlebitis, arterial embolism, coronary and cerebral arterial thrombosis, cerebral embolism, kidney embolism, pulmonary embolism, first or recurrent myocardial infarction, unstable angina, and cerebral infarction, stroke, atherosclerosis.

The compounds of the present invention can be administered alone or in combination with one or more therapeutic agents. These include, for example, other anticoagulant, antiplatelet, or platelet inhibitory agents which include non-steroidal anti-inflammatory agents such as aspirin, ibuprofen, naproxen sodium, indomethacin, piroxicam and ticlopidine, thrombin inhibitors such as argatroban, efegatran, inogatran, factor VIIa inhibitors, thrombolytic or fibrinolytic agents such as tissue plasminogen activator, urokinase or streptokinase, and GP IIIb-IIa antagonists.

The compounds are thus well suited to formulation for convenient administration to mammals for the prevention and treatment of such disorders. The following examples further illustrate typical formulations provided by the invention.

| Formulation 1 | |
|---|---|
| Ingredient | Amount |
| compound of Formulas 1–8 | 200 mg |
| sodium benzoate | 5 mg |
| isotonic saline | 1000 mL |

The above ingredients are mixed and dissolved in the saline for IV administration to a human suffering from, for example, arterial thrombosis.

| Formulation 2 | |
|---|---|
| Ingredient | Amount |
| compound of Formulas 1–8 | 100 mg |
| cellulose, microcrystalline | 400 mg |
| stearic acid | 5 mg |
| silicon dioxide | 10 mg |
| sugar, confectionery | 50 mg |

The ingredients are blended to uniformity and pressed into a tablet that is well suited for oral administration to a human for preventing, for example, cerebral infarction.

| Formulation 3 | |
|---|---|
| Ingredient | Amount |
| compound of Formulas 1–8 | 200 mg |
| starch, dried | 250 mg |
| magnesium stearate | 10 mg |

The ingredients are combined and milled to afford material suitable for filling hard gelatin capsules administered to humans suffering from, for example, venous thrombosis.

| Formulation 4 | |
|---|---|
| Ingredient | Amount % wt./wt. |
| compound of Formulas 1–8 | 1 |
| Polyethylene glycol 1000 | 74.5 |
| Polyethylene glycol 4000 | 24.5 |

The ingredients are combined via melting and then poured into molds containing 2.5 g total weight.

| Formulation 5 | |
|---|---|
| Ingredient | Amount % wt./wt. |
| compound of Formulas 1–8 | 0.1% |
| Propellant 11/12 | 98.9% |
| Oleic acid | 1% |

The ingredients are dispersed in oleic acid with the propellant. The mixture is added to an aerosol container fitted with a metering device.

What is claimed is:

1. A compound according to Formula 8

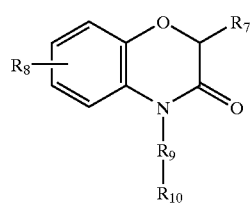

8 or stereoisomers or pharmaceutically acceptable salt forms or prodrugs thereof, wherein $R_7$ is (3-amidino)phenyl, (3-hydroxy)phenyl, [3-hydroxylamino(imino)methyl]-phenyl, [3-hydrazino(imino)methyl]-phenyl, (3-aminomethyl)phenyl, (3-amino)phenyl, (3-methylamino)phenyl, (3-dimethylamino)phenyl, (5-amidino-2-hydroxy)phenyl, (5-amidino-2-methoxy)phenyl, (1-amidino)piperid-3-yl, (1-amidino)pyrrolid-3-yl, (5-amidino)thien-2-yl, (5-amidino)furan-2-yl, (5-amidino)-1,3-oxazol-2-yl, (2-amidino)-1,3-oxazol-5-yl, 1H-pyrazol-5-yl, tetrahydro-1H-pyrazol-3-yl, (1-amidino)tetrahydro-1H-pyrazol-3-yl, (2-amidino)-1H-imidazol-4-yl, (2-amino)-1H-imidazol-4-yl, (5-amidino)-1H-imidazol-2-yl, (5-amino)-1H-imidazol-2-yl, pyridin-3-yl, (4-amino)pyridin-3-yl, (4-dimethylamino)pyridin-3-yl, (6-amino)pyridin-2-yl, (6-amidino)pyridin-2-yl, (2-amino)pyridin-4-yl, (2-amidino)pyridin-4-yl, (2-amidino)pyrimid-4-yl, (2-amino)pyrimidin-4-yl, (4-amidino)pyrimid-2-yl, (4-amino)pyrimidin-2-yl, (6-amidino)pyrazin-2-yl, (6-amino)pyrazin-2-yl, (4-amidino)-1,3,5-triazin-2-yl, (4-amino)-1,3,5-triazin-2-yl, (3-amidino)-1,2,4-triazin-5-yl, (3-amino)-1,2,4-triazin-5-yl, (1-amidino)piperid-3-ylmethyl, (1-amidino)pyrrolid-3-ylmethyl, (5-amidino)thien-2-ylmethyl, (5-amidino)furan-2-ylmethyl, (5-amidino)oxazol-2-ylmethyl, (2-amidino)imidazol-5-ylmethyl, (5-amidino)imidazol-2-ylmethyl, (6-amidino)pyridin-2-ylmethyl, (6-amino)pyridin-2-ylmethyl, (2-amidino)pyrimidin-4-ylmethyl, (2-amino)pyrimidin-4-ylmethyl, (4-amidino)pyrimidin-2-ylmethyl, (4-amino)pyrimidin-2-ylmethyl, (6-amidino)pyrazin-2-ylmethyl, (6-amino)pyrazin-2-ylmethyl, 3-aminocyclohexyl, 3-amidinocyclohexyl, 3-aminocyclohexylmethyl, 3-amidinocyclohexylmethyl, 3-aminocyclopentyl, 3-amidinocyclopentyl, and 3-amidinocyclopentylmethyl;

$R_8$ is Br, I, $C_2H_5$, H, Cl, F, SH, SMe, $CF_3$, $CH_3$, $CO_2H$, $CO_2Me$, CN, C(=NH)$NH_2$, C(=NH)NHOH, C(=NH)$NHNH_2$, C(=O)$NH_2$, $CH_2OH$, $CH_2NH_2$, $NO_2$, OH, OMe, $OCH_2Ph$, $OCH_2CO_2H$, $O(CH_2)_2CO_2H$, $O(CH_2)_3CO_2H$, $NHCH_2CO_2H$, $NH(CH_2)_2CO_2H$, $NH(CH_2)_3CO_2H$, $OCH_2CH_2OH$, $OCH_2$(1H-tetrazol-5-yl), $NH_2$, NHButyl, $NMe_2$, NHPh, $NHCH_2Ph$, NHC(=O)Me, NHC(=O)c-Hexyl, NHC(=O)$CH_2$c-Hexyl, NHC(=O)Ph, NHC(=O)$CH_2Ph$, NHS(=O)$_2$Me, NHS(=O)$_2$c-Hexyl, NHS(=O)$_2CH_2$c-Hexyl, NHS(=O)$_2$Ph, and NHS(=O)$_2CH_2Ph$, $R_9$ is $(CH_2)_5$, $(CH_2)_4$, $(CH_2)_6$, $CH_2C(=O)NHCH_2CH_2$, $CH_2CH_2NHC(=O)CH_2$, $(CH_2)_2NH(CH_2)_2$, $(CH_2)_2O(CH_2)_2$, $C_6H_4$, $CH_2C_6H_4$, $C_6H_4CH_2$, $C_6H_{10}$, $CH_2C_6H_{10}$, $C_6H_{10}CH_2$, $C_5H_8$, $CH_2C_5H_8$, $C_5H_8CH_2$, and $CH_2CH=CHCH_2CH_2$; and $R_{10}$ is 2,6-dimethylpiperidinyl, 2,2,6,6-tetramethylpiperidinyl-4-one, piperidinyl, 2,2,6,6-tetramethylpiperidinyl, (2-carboxy)piperidinyl, (3-carboxy)piperidinyl, (4-carboxy)piperidinyl, 3,5-dimethylpiperidinyl, (4-hydroxy)piperidinyl, (2-imino)piperidinyl, piperidin-4-one-yl, (2-dimethylaminomethyl)-piperidinyl, (4-dimethylamino)-piperidinyl, (4-sulphonyloxy)-piperidinyl, (2-phenyl)piperidinyl, 2,5-dimethylpyrrolidinyl, pyrrolidinyl, (2-carboxy)pyrrolidinyl, (3-N-acetyl-N-methyl)pyrrolidinyl, (3-amino)pyrrolidinyl, (2,5-bis-methoxymethyl)-pyrrolidinyl, 2-hydroxymethyl-pyrrolidinyl, 2-hydroxymethyl-5-methyl-pyrrolidinyl, diisopropylamino, diethylamino, methylamino, 1-methyl-4,5-dihydro-1H-imidazol-2-yl, 2,5-dimethyl-1H-1-imidazolyl, morpholinyl, 2,6-dimethylmorpholinyl, piperazinyl, 2,6-dimethylpiperazinyl, 1H-pyrazolyl, tetrahydro-1H-pyrazolyl, and 2,5-dimethyltetrahydro-1H-1-pyrazolyl.

2. A compound according to claim 1 wherein $R_7$ is (2-hydroxy, 5-amidino)phenyl.

3. A compound according to claim 1 wherein $R_8$ is H.

4. A compound according to claim 1 wherein $R_9$ is $(CH_2)_5$.

5. A compound according to claim 1 wherein $R_{10}$ is 2,6-dimethylpiperidinyl.

6. A compound according to claim 1 wherein $R_8$ is H, $R_9$ is $(CH_2)_5$, and $R_{10}$ is 2,6-dimethylpiperidinyl.

7. A compound according to claim 1 wherein $R_8$ is H, $R_9$ is $(CH_2)_5$, and $R_{10}$ is 2,5-dimethylpyrrolidinyl.

8. A compound which is:
   3-(4-5-[(2R,6S)-2,6-dimethyltetrahydro-1(2H)-pyridinyl]pentyl-3-oxo-3,4-dihydro-2H-1,4-benzoxazin-2-yl)-4-methoxybenzenecarboximidamide;
   3-(4-5-[(2R,6S)-2,6-Dimethyltetrahydro-1(2H)-pyridinyl]pentyl-3-oxo-3,4-dihydro-2H-1,4-benzoxazin-2-yl)benzenecarboximidamide;
   4-5-[(2R,6S)-2,6-Dimethyltetrahydro-1(2H)-pyridinyl]pentyl-2-(3-hydroxyphenyl)-2H-1,4-benzoxazin-3(4H)-one;
   3-(4-5-[(2R,6S)-2,6-Dimethyltetrahydro-1(2H)-pyridinyl]pentyl-3-oxo-3,4-dihydro-2H-1,4-benzoxazin-2-yl)-N-hydroxybenzenecarboximidamide;
   3-(4-5-[(2R,6S)-2,6-Dimethyltetrahydro-1(2H)-pyridinyl]pentyl-3-oxo-3,4-dihydro-2H-1,4-benzoxazin-2-yl)benzenecarboximidohydrazide;
   2-[3-(Aminomethyl)phenyl]-4-5-[(2R,6S)-2,6-dimethyltetrahydro-1(2H)-pyridinyl]pentyl-2H-1,4-benzoxazin-3(4H)-one;
   2-(3-Aminophenyl)-4-5-[(2R,6S)-2,6-dimethyltetrahydro-1(2H)-pyridinyl]pentyl-2H-1,4-benzoxazin-3(4H)-one;
   4-5-[(2R,6S)-2,6-Dimethyltetrahydro-1(2H)-pyridinyl]pentyl-2-[3-(methylamino)phenyl]-2H-1,4-benzoxazin-3(4H)-one;

2-[3-(Dimethylamino)phenyl]-4-5-[(2R,6S)-2,6-dimethyltetrahydro-1(2H)-pyridinyl]pentyl-2H-1,4-benzoxazin-3(4H)-one;

3-(4-5-[(2R,6S)-2,6-Dimethyltetrahydro-1(2H)-pyridinyl]pentyl-3-oxo-3,4-dihydro-2H-1,4-benzoxazin-2-yl)-4-hydroxybenzenecarboximidamide;

3-(4-5-[(2R,6S)-2,6-Dimethyltetrahydro-1(2H)-pyridinyl]pentyl-3-oxo-3,4-dihydro-2H-1,4-benzoxazin-2-yl)tetrahydro-1(2H)-pyridinecarboximidamide;

3-(4-5-[(2R,6S)-2,6-Dimethyltetrahydro-1(2H)-pyridinyl]pentyl-3-oxo-3,4-dihydro-2H-1,4-benzoxazin-2-yl)-1-pyrrolidinecarboximidamide;

5-(4-5-[(2R,6S)-2,6-Dimethyltetrahydro-1(2H)-pyridinyl]pentyl-3-oxo-3,4-dihydro-2H-1,4-benzoxazin-2-yl)-2-thiophenecarboximidamide;

5-(4-5-[(2R,6S)-2,6-Dimethyltetrahydro-1(2H)-pyridinyl]pentyl-3-oxo-3,4-dihydro-2H-1,4-benzoxazin-2-yl)-2-furancarboximidamide;

2-(4-5-[(2R,6S)-2,6-Dimethyltetrahydro-1(2H)-pyridinyl]pentyl-3-oxo-3,4-dihydro-2H-1,4-benzoxazin-2-yl)-1,3-oxazole-5-carboximidamide;

5-(4-5-[(2R,6S)-2,6-Dimethyltetrahydro-1(2H)-pyridinyl]pentyl-3-oxo-3,4-dihydro-2H-1,4-benzoxazin-2-yl)-1,3-oxazole-2-carboximidamide;

4-5-[(2R,6S)-2,6-Dimethyltetrahydro-1(2H)-pyridinyl]pentyl-2-(1H-pyrazol-5-yl)-2H-1,4-benzoxazin-3(4H)-one;

4-5-[(2R,6S)-2,6-Dimethyltetrahydro-1(2H)-pyridinyl]pentyl-2-tetrahydro-1H-pyrazol-3-yl-2H-1,4-benzoxazin-3(4H)-one;

5-(4-5-[(2R,6S)-2,6-Dimethyltetrahydro-1(2H)-pyridinyl]pentyl-3-oxo-3,4-dihydro-2H-1,4-benzoxazin-2-yl)-1-pyrazolidinecarboximidamide;

4-(4-5-[(2R,6S)-2,6-Dimethyltetrahydro-1(2H)-pyridinyl]pentyl-3-oxo-3,4-dihydro-2H-1,4-benzoxazin-2-yl)-1H-imidazole-2-carboximidamide;

2-(2-Amino-1H-imidazol-4-yl)-4-5-[(2R,6S)-2,6-dimethyltetrahydro-1(2H)-pyridinyl]pentyl-2H-1,4-benzoxazin-3(4H)-one;

2-(4-5-[(2R,6S)-2,6-Dimethyltetrahydro-1(2H)-pyridinyl]pentyl-3-oxo-3,4-dihydro-2H-1,4-benzoxazin-2-yl)-1H-imidazole-5-carboximidamide;

2-(5-Amino-1H-imidazol-2-yl)-4-5-[(2R,6S)-2,6-dimethyltetrahydro-1(2H)-pyridinyl]pentyl-2H-1,4-benzoxazin-3(4H)-one;

4-5-[(2R,6S)-2,6-Dimethyltetrahydro-1(2H)-pyridinyl]pentyl-2-(3-pyridinyl)-2H-1,4-benzoxazin-3(4H)-one;

2-(4-Amino-3-pyridinyl)-4-5-[(2R,6S)-2,6-dimethyltetrahydro-1(2H)-pyridinyl]pentyl-2H-1,4-benzoxazin-3(4H)-one;

2-[4-(Dimethylamino)-3-pyridinyl]-4-5-[(2R,6S)-2,6-dimethyltetrahydro-1(2H)-pyridinyl]pentyl-2H-1,4-benzoxazin-3(4H)-one;

2-(6-Amino-2-pyridinyl)-4-5-[(2R,6S)-2,6-dimethyltetrahydro-1(2H)-pyridinyl]pentyl-2H-1,4-benzoxazin-3(4H)-one;

6-(4-5-[(2R,6S)-2,6-Dimethyltetrahydro-1(2H)-pyridinyl]pentyl-3-oxo-3,4-dihydro-2H-1,4-benzoxazin-2-yl)-2-pyridinecarboximidamide;

2-(2-Amino-4-pyridinyl)-4-5-[(2R,6S)-2,6-dimethyltetrahydro-1(2H)-pyridinyl]pentyl-2H-1,4-benzoxazin-3(4H)-one;

4-(4-5-[(2R,6S)-2,6-Dimethyltetrahydro-1(2H)-pyridinyl]pentyl-3-oxo-3,4-dihydro-2H-1,4-benzoxazin-2-yl)-2-pyridinecarboximidamide;

4-(4-5-[(2R,6S)-2,6-Dimethyltetrahydro-1(2H)-pyridinyl]pentyl-3-oxo-3,4-dihydro-2H-1,4-benzoxazin-2-yl)-2-pyrimidinecarboximidamide;

2-(2-Amino-4-pyrimidinyl)-4-5-[(2R,6S)-2,6-dimethyltetrahydro-1(2H)-pyridinyl]pentyl-2H-1,4-benzoxazin-3(4H)-one;

2-(4-5-[(2R,6S)-2,6-Dimethyltetrahydro-1(2H)-pyridinyl]pentyl-3-oxo-3,4-dihydro-2H-1,4-benzoxazin-2-yl)-4-pyrimidinecarboximidamide;

2-(4-Amino-2-pyrimidinyl)-4-5-[(2R,6S)-2,6-dimethyltetrahydro-1(2H)-pyridinyl]pentyl-2H-1,4-benzoxazin-3(4H)-one;

6-(4-5-[(2R,6S)-2,6-Dimethyltetrahydro-1(2H)-pyridinyl]pentyl-3-oxo-3,4-dihydro-2H-1,4-benzoxazin-2-yl)-2-pyrazinecarboximidamide;

2-(6-Amino-2-pyrazinyl)-4-5-[(2R,6S)-2,6-dimethyltetrahydro-1(2H)-pyridinyl]pentyl-2H-1,4-benzoxazin-3(4H)-one;

4-(4-5-[(2R,6S)-2,6-Dimethyltetrahydro-1(2H)-pyridinyl]pentyl-3-oxo-3,4-dihydro-2H-1,4-benzoxazin-2-yl)-1,3,5-triazine-2-carboximidamide;

2-(4-Ainino-1,3,5-triazin-2-yl)-4-5-[(2R,6S)-2,6-dimethyltetrahydro-1(2H)-pyridinyl]pentyl-2H-1,4-benzoxazin-3(4H)-one;

5-(4-5-[(2R,6S)-2,6-Dimethyltetrahydro-1(2H)-pyridinyl]pentyl-3-oxo-3,4-dihydro-2H-1,4-benzoxazin-2-yl)-1,2,4-triazine-3-carboximidamide;

2-(3-Amino-1,2,4-triazin-5-yl)-4-5-[(2R,6S)-2,6-dimethyltetrahydro-1(2H)-pyridinyl]pentyl-2H-1,4-benzoxazin-3(4H)-one;

3-[(4-5-[(2R,6S)-2,6-Dimethyltetrahydro-1(2H)-pyridinyl]pentyl-3-oxo-3,4-dihydro-2H-1,4-benzoxazin-2-yl)methyl]benzenecarboximidamide;

2-(3-Aminobenzyl)-4-5-[(2R,6S)-2,6-dimethyltetrahydro-1(2H)-pyridinyl]pentyl-2H-1,4-benzoxazin-3(4H)-one;

2-[3-(Aminomethyl)benzyl]-4-5-[(2R,6S)-2,6-dimethyltetrahydro-1(2H)-pyridinyl]pentyl-2H-1,4-benzoxazin-3(4H)-one;

3-[(4-5-[(2R,6S)-2,6-Dimethyltetrahydro-1(2H)-pyridinyl]pentyl-3-oxo-3,4-dihydro-2H-1,4-benzoxazin-2-yl)methyl]tetrahydro-1(2H)-pyridinecarboximidamide;

3-[(4-5-[(2R,6S)-2,6-dimethyltetrahydro-1(2H)-pyridinyl]pentyl-3-oxo-3,4-dihydro-2H-1,4-benzoxazin-2-yl)methyl-1-pyrrolidinecarboximidamide;

5-[(4-5-[(2R,6S)-2,6-Dimethyltetrahydro-1(2H)-pyridinyl]pentyl-3-oxo-3,4-dihydro-2H-1,4-benzoxazin-2-yl)methyl]-2-thiophenecarboximidamide;

5-[(4-5-[(2R,6S)-2,6-Dimethyltetrahydro-1(2H)-pyridinyl]pentyl-3-oxo-3,4-dihydro-2H-1,4-benzoxazin-2-yl)methyl]-2-furancarboximidamide;

2-[(4-5-[(2R,6S)-2,6-Dimethyltetrahydro-1(2H)-pyridinyl]pentyl-3-oxo-3,4-dihydro-2H-1,4-benzoxazin-2-yl)methyl]-1,3-oxazole-5-carboximidamide;

5-[(4-5-[(2R,6S)-2,6-Dimethyltetrahydro-1(2H)-pyridinyl]pentyl-3-oxo-3,4-dihydro-2H-1,4-benzoxazin-2-yl)methyl]-1H-imidazole-2-carboximidamide;

2-[(4-5-[(2R,6S)-2,6-Dimethyltetrahydro-1(2H)-pyridinyl]pentyl-3-oxo-3,4-dihydro-2H-1,4-benzoxazin-2-yl)methyl]-1H-imidazole-5-carboximidamide;

6-[(4-5-[(2R,6S)-2,6-Dimethyltetrahydro-1(2H)-pyridinyl]pentyl-3-oxo-3,4-dihydro-2H-1,4-benzoxazin-2-yl)methyl]-2-pyridinecarboximidamide;

2-[(6-Amino-2-pyridinyl)methyl]-4-5-[(2R,6S)-2,6-dimethyltetrahydro-1(2H)-pyridinyl]pentyl-2H-1,4-benzoxazin-3(4H)-one;

4-[(4-5-[(2R,6S)-2,6-Dimethyltetrahydro-1(2H)-pyridinyl]pentyl-3-oxo-3,4-dihydro-2H-1,4-benzoxazin-2-yl)methyl]-2-pyrimidinecarboximidamide;

2-[(2-Amino-4-pyrimidinyl)methyl]-4-5-[(2R,6S)-2,6-dimethyltetrahydro-1(2H)-pyridinyl]pentyl-2H-1,4-benzoxazin-3(4H)-one;

2-[(4-5-[(2R,6S)-2,6-Dimethyltetrahydro-1(2H)-pyridinyl]pentyl-3-oxo-3,4-dihydro-2H-1,4-benzoxazin-2-yl)methyl]-4-pyrimidinecarboximidamide;

2-[(4-Amino-2-pyrimidinyl)methyl]-4-5-[(2R,6S)-2,6-dimethyltetrahydro-1(2H)-pyridinyl]pentyl-2H-1,4-benzoxazin-3(4H)-one;

6-[(4-5-[(2R,6S)-2,6-Dimethyltetrahydro-1(2H)-pyridinyl]pentyl-3-oxo-3,4-dihydro-2H-1,4-benzoxazin-2-yl)methyl]-2-pyrazinecarboximidamide;

2-[(6-Amino-2-pyrazinyl)methyl]-4-5-[(2R,6S)-2,6-dimethyltetrahydro-1(2H)-pyridinyl]pentyl-2H-1,4-benzoxazin-3(4H)-one;

2-(3-Aminocyclohexyl)-4-5-[(2R,6S)-2,6-dimethyltetrahydro-1(2H)-pyridinyl]pentyl-2H-1,4-benzoxazin-3(4H)-one;

3-(4-5-[(2R,6S)-2,6-Dimethyltetrahydro-1(2H)-pyridinyl]pentyl-3-oxo-3,4-dihydro-2H-1,4-benzoxazin-2-yl)cyclohexanecarboximidamide;

2-[(3-Aminocyclohexyl)methyl]-4-5-[(2R,6S)-2,6-dimethyltetrahydro-1(2H)-pyridinyl]pentyl-2H-1,4-benzoxazin-3(4H)-one;

3-[(4-5-[(2R,6S)-2,6-Dimethyltetrahydro-1(2H)-pyridinyl]pentyl-3-oxo-3,4-dihydro-2H-1,4-benzoxazin-2-yl)methyl] cyclohexanecarboximidamide;

2-(3-Aminocyclopentyl)-4-5-[(2R,6S)-2,6-dimethyltetrahydro-1(2H)-pyridinyl]pentyl-2H-1,4-benzoxazin-3(4H)-one;

3-(4-5-[(2R,6S)-2,6-Dimethyltetrahydro-1(2H)-pyridinyl]pentyl-3-oxo-3,4-dihydro-2H-1,4-benzoxazin-2-yl)cyclopentanecarboximidamide;

2-[(3-Aminocyclopentyl)methyl]-4-5-[(2R,6S)-2,6-dimethyltetrahydro-1(2H)-pyridinyl]pentyl-2H-1,4-benzoxazin-3(4H)-one;

3-[(4-5-[(2R,6S)-2,6-Dimethyltetrahydro-1(214)-pyridinyl]pentyl-3-oxo-3,4-dihydro-2H-1,4-benzoxazin-2-yl)methyl] cyclopentanecarboximidamide;

3-(4-4-[(2R,6S)-2,6-Dimethyltetrahydro-1(2H)-pyridinyl]butyl-3-oxo-3,4-dihydro-2H-1,4-benzoxazin-2-yl)benzenecarboximidamide;

3-(4-6-[(2R,6S)-2,6-Dimethyltetrahydro-1(2H)-pyridinyl]hexyl-3-oxo-3,4-dihydro-2H-1,4-benzoxazin-2-yl)benzenecarboximidamide;

2-(2-3-[Amino(imino)methyl]phenyl-3-oxo-2,3-dihydro-4H-1,4-benzoxazin-4-yl)-N-2-[(2R,6S)-2,6-dimethyltetrahydro-1(2H)-pyridinyl]ethylacetamide;

3-(2-3-[Amino(imino)methyl]phenyl-3-oxo-2,3-dihydro-4H-1,4-benzoxazin-4-yl)-N-[(2R,6S)-2,6-dimethyltetrahydro-1(2H)-pyridinyl] methylpropanamide;

3-4-[2-(2-[(2R,6S)-2,6-Dimethyltetrahydro-1(2H)-pyridinyl]ethylamino)ethyl]-3-oxo-3,4-dihydro-2H-1,4-benzoxazin-2-ylbenzenecarboximidamide;

3-[4-(2-2-[(2R,6S)-2,6-Dimethyltetrahydro-1(2H)-pyridinyl]ethoxyethyl)-3-oxo-3,4-dihydro-2H-1,4-benzoxazin-2-yl]benzenecarboximidamide;

3-(4-4-[(2R,6S)-2,6-Dimethyltetrahydro-1(2H)-pyridinyl]phenyl-3-oxo-3,4-dihydro-2H-1,4-benzoxazin-2-yl)benzenecarboximidamide;

3-(4-4-[(2R,6S)-2,6-Dimethyltetrahydro-1(2H)-pyridinyl]benzyl-3-oxo-3,4-dihydro-2H-1,4-benzoxazin-2-yl)benzenecarboximidamide;

3-[4-(4-[(2R,6S)-2,6-Dimethyltetrahydro-1(2H)-pyridinyl]methylphenyl)-3-oxo-3,4-dihydro-2H-1,4-benzoxazin-2-yl]benzenecarboximidamide;

3-(4-4-[(2R,6S)-2,6-Dimethyltetrahydro-1(2H)-pyridinyl]cyclohexyl-3-oxo-3,4-dihydro-2H-1,4-benzoxazin-2-yl)benzenecarboximidamide;

3-[4-(4-[(2R,6S)-2,6-Dimethyltetrahydro-1(2H)-pyridinyl]cyclohexylmethyl)-3-oxo-3,4-dihydro-2H-1,4-benzoxazin-2-yl]benzenecarboximidamide;

3-[4-(4-[(2R,6S)-2,6-Dimethyltetrahydro-1(2H)-pyridinyl]methylcyclohexyl)-3-oxo-3,4-dihydro-2H-1,4-benzoxazin-2-yl]benzenecarboximidamide;

3-(4-3-[(2R,6S)-2,6-Dimethyltetrahydro-1(2H)-pyridinyl]cyclopentyl-3-oxo-3,4-dihydro-2H-1,4-benzoxazin-2-yl)benzenecarboximidamide;

3-[4-(3-[(2R,6S)-2,6-Dimethyltetrahydro-1(2H)-pyridinyl]cyclopentylmethyl)-3-oxo-3,4-dihydro-2H-1,4-benzoxazin-2-yl]benzenecarboximidamide;

3-[4-(3-[(2R,6S)-2,6-Dimethyltetrahydro-1(2H)-pyridinyl]methylcyclopentyl)-3-oxo-3,4-dihydro-2H-1,4-benzoxazin-2-yl]benzenecarboximidamide;

3-(4-(E)-5-[(2R,6S)-2,6-Dimethyltetrahydro-1(2H)-pyridinyl]-2-pentenyl-3-oxo-3,4-dihydro-2H-1,4-benzoxazin-2-yl)benzenecarboximidamide;

3-[3-Oxo-4-(5-piperidinopentyl)-3,4-dihydro-2H-1,4-benzoxazin-2-yl]benzenecarboximidamide;

3-3-Oxo-4-[5-(2,2,6,6-tetramethylpiperidino)pentyl]-3,4-dihydro-2H-1,4-benzoxazin-2-ylbenzenecarboximidamide;

1-[5-(2-3-[Amino(imino)methyl]phenyl-3-oxo-2,3-dihydro-4H-1,4-benzoxazin-4-yl)pentyl]-2-piperidinecarboxylic acid;

1-[5-(2-3-[Amino(imino)methyl]phenyl-3-oxo-2,3-dihydro-4H-1,4-benzoxazin-4-yl)pentyl]-3-piperidinecarboxylic acid;

1-[5-(2-3-[Amino(imino)methyl]phenyl-3-oxo-2,3-dihydro-4H-1,4-benzoxazin-4-yl)pentyl]-4-piperidinecarboxylic acid;

3-4-[5-(3,5-Dimethylpiperidino)pentyl]-3-oxo-3,4-dihydro-2H-1,4-benzoxazin-2-ylbenzenecarboximidamide;

3-4-[5-(4-Hydroxypiperidino)pentyl]-3-oxo-3,4-dihydro-2H-1,4-benzoxazin-2-ylbenzenecarboximidamide;

3-4-[5-(2-Iminopiperidino)pentyl]-3-oxo-3,4-dihydro-2H-1,4-benzoxazin-2-ylbenzenecarboximidamide;

3-3-Oxo-4-[5-(4-oxopiperidino)pentyl]-3,4-dihydro-2H-1,4-benzoxazin-2-ylbenzenecarboximidamide;

3-[4-(5-2-[(Dimethylamino)methyl]piperidinopentyl)-3-oxo-3,4-dihydro-2H-1,4-benzoxazin-2-yl]benzenecarboximidamide;

3-(4-5-[4-(Dimethylamino)piperidino]pentyl-3-oxo-3,4-dihydro-2H-1,4-benzoxazin-2-yl)benzenecarboximidamide;

1-[5-(2-3-[Amino(imino)methyl]phenyl-3-oxo-2,3-dihydro-4H-1,4-benzoxazin-4-yl)pentyl]-4-piperidinesulfonic acid;

3-3-Oxo-4-[5-(2-phenylpiperidino)pentyl]-3,4-dihydro-2H-1,4-benzoxazin-2-ylbenzenecarboximidamide;

3-4-[5-(2,5-Dimethyl-1-pyrrolidinyl)pentyl]-3-oxo-3,4-dihydro-2H-1,4-benzoxazin-2-ylbenzenecarboximidamide;

3-3-Oxo-4-[5-(1-pyrrolidinyl)pentyl]-3,4-dihydro-2H-1,4-benzoxazin-2-ylbenzenecarboximidamide;

1-[5-(2-3-[Amino(imino)methyl]phenyl-3-oxo-2,3-dihydro-4H-1,4-benzoxazin-4-yl)pentyl]-2-pyrrolidinecarboxylic acid;

N-1-[5-(2-3-[Amino(imino)methyl]phenyl-3-oxo-2,3-dihydro-4H-1,4-benzoxazin-4-yl)pentyl]tetrahydro-1H-pyrrol-3-yl-N-methylacetamide;

3-4-[5-(3-Amino-1-pyrrolidinyl)pentyl]-3-oxo-3,4-dihydro-2H-1,4-benzoxazin-2-ylbenzenecarboximidamide;

3-(4-5-[2,5-Bis(methoxymethyl)-1-pyrrolidinyl]pentyl-3-oxo-3,4-dihydro-2H-1,4-benzoxazin-2-yl)benzenecarboximidamide;

3-(4-5-[2-(Hydroxymethyl)-1-pyrrolidinyl]pentyl-3-oxo-3,4-dihydro-2H-1,4-benzoxazin-2-yl)benzenecarboximidamide;

3-(4-5-12-(Hydroxymethyl)-5-methyl-1-pyrrolidinyl]pentyl-3-oxo-3,4-dihydro-2H-1,4-benzoxazin-2-yl)benzenecarboximidamide;

3-4-[5-(Diisopropylamino)pentyl]-3-oxo-3,4-dihydro-2H-1,4-benzoxazin-2-ylbenzenecarboximidamide;

3-4-[5-(Diethylamino)pentyl]-3-oxo-3,4-dihydro-2H-1,4-benzoxazin-2-ylbenzenecarboximidamide;

3-4-[5-(Methylamino)pentyl]-3-oxo-3,4-dihydro-2H-1,4-benzoxazin-2-ylbenzenecarboximidamide;

3-4-[5-(1-Methyl-1H-imidazol-2-yl)pentyl]-3-oxo-3,4-dihydro-2H-1,4-benzoxazin-2-ylbenzenecarboximidamide;

3-4-[5-(2,5-Dimethyl-1H-imidazol-1-yl)pentyl]-3-oxo-3,4-dihydro-2H-1,4-benzoxazin-2-ylbenzenecarboximidamide;

3-[4-(5-Morpholinopentyl)-3-oxo-3,4-dihydro-2H-1,4-benzoxazin-2-yl]benzenecarboximidamide;

3-4-[5-(3,5-Dimethylmorpholino)pentyl]-3-oxo-3,4-dihydro-2H-1,4-benzoxazin-2-ylbenzenecarboximidamide;

3-[3-Oxo-4-(5-piperazinopentyl)-3,4-dihydro-2H-1,4-benzoxazin-2-yl]benzenecarboximidamide;

3-4-[5-(2,6-Dimethylpiperazino)pentyl]-3-oxo-3,4-dihydro-2H-1,4-benzoxazin-2-ylbenzenecarboximidamide;

3-3-Oxo-4-[5-(1H-pyrazol-1-yl)pentyl]-3,4-dihydro-2H-1,4-benzoxazin-2-ylbenzenecarboximidamide;

3-[3-Oxo-4-(5-tetrahydro-1H-pyrazol-1-ylpentyl)-3,4-dihydro-2H-1,4-benzoxazin-2-yl]benzenecarboximidamide;

3-4-[5-(2,5-Dimethyltetrahydro-1H-pyrazol-1-yl)pentyl]-3-oxo-3,4-dihydro-2H-1,4-benzoxazin-2-ylbenzenecarboximidamide;

3-(6-Chloro-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(4-5-[(2R,6S)-2,6-Dimethyltetrahydro-1(2H)-pyridinyl]pentyl-6-fluoro-3-oxo-3,4-dihydro-2H-1,4-benzoxazin-2-yl)benzenecarboximidamide;

3-(4-5-[(2R,6S)-2,6-Dimethyltetrahydro-1(2H)-pyridinyl]pentyl-3-oxo-6-sulfanyl-3,4-dihydro-2H-1,4-benzoxazin-2-yl)benzenecarboximidamide;

3-[4-5-[(2R,6S)-2,6-Dimethyltetrahydro-1(2H)-pyridinyl]pentyl-6-(methylsulfanyl)-3-oxo-3,4-dihydro-2H-1,4-benzoxazin-2-yl]benzenecarboximidamide;

3-[4-5-[(2R,6S)-2,6-Dimethyltetrahydro-1(2H)-pyridinyl]pentyl-3-oxo-6-(trifluoromethyl)-3,4-dihydro-2H-1,4-benzoxazin-2-yl]benzenecarboximidamide;

3-(4-5-[(2R,6S)-2,6-Dimethyltetrahydro-1(2H)-pyridinyl]pentyl-6-methyl-3-oxo-3,4-dihydro-2H-1,4-benzoxazin-2-yl)benzenecarboximidamide;

2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazine-6-carboxylic acid;

Methyl 2-3-[amino(imino)methyl]phenyl-4-5-[(2R,6S)-2,6-dimethyltetrahydro-1(2H)-pyridinyl]pentyl-3-oxo-3,4-dihydro-2H-1,4-benzoxazine-6-carboxylate;

3-(6-Cyano-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazine-6-carboximidamide;

2-3-[Amino(imino)methyl]phenyl-4-5-[(2R,6S)-2,6-dimethyltetrahydro-1(2H)-pyridinyl]pentyl-N-hydroxy-3-oxo-3,4-dihydro-2H-1,4-benzoxazine-6-carboximidamide;

3-4-5-[(2R,6S)-2,6-Dimethyltetrahydro-1(2H)-pyridinyl]pentyl-6-[hydrazino(imino)methyl]-3-oxo-3,4-dihydro-2H-1,4-benzoxazin-2-ylbenzenecarboximidamide;

2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazine-6-carboxamide;

3-[4-5-[(2R,6S)-2,6-Dimethyltetrahydro-1(2H)-pyridinyl]pentyl-6-(hydroxymethyl)-3-oxo-3,4-dihydro-2H-1,4-benzoxazin-2-yl]benzenecarboximidamide;

3-(6-(Aminomethyl)-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(4-5-[(2R,6S)-2,6-Dimethyltetrahydro-1(2H)-pyridinyl]pentyl-6-nitro-3-oxo-3,4-dihydro-2H-1,4-benzoxazin-2-yl)benzenecarboximidamide;

3-(4-5-[(2R,6S)-2,6-Dimethyltetrahydro-1(2H)-pyridinyl]pentyl-6-hydroxy-3-oxo-3,4-dihydro-2H-1,4-benzoxazin-2-yl)benzenecarboximidamide;

3-(4-5-[(2R,6S)-2,6-Dimethyltetrahydro-1(2H)-pyridinyl]pentyl-6-methoxy-3-oxo-3,4-dihydro-2H-1,4-benzoxazin-2-yl)benzenecarboximidamide;

3-(6-(Benzyloxy)-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

2-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)oxy]acetic acid 3-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)oxy]propanoic acid;

4-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)oxy]butanoic acid;

2-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)amino]acetic acid;

3-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)amino]propanoic acid;

4-[(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)amino]butanoic acid;

3-[4-5-[(2R,6S)-2,6-Dimethyltetrahydro-1(2H)-pyridinyl]pentyl-6-(2-hydroxyethoxy)-3-oxo-3,4-dihydro-2H-1,4-benzoxazin-2-yl]benzenecarboximidamide;

3-[4-5-[(2R,6S)-2,6-Dimethyltetrahydro-1(2H)-pyridinyl]pentyl-3-oxo-6-(2H-1,2,3,4-tetraazol-5-ylmethoxy)-3,4-dihydro-2H-1,4-benzoxazin-2-yl]benzenecarboximidamide;

3-(6-Amino-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(6-(Butylamino)-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(6-(Dimethylamino)-4-5-[(2R,6S)-2,6-dimethyltetrahydto-1(2H)-pyridinyl]pentyl-3-oxo-3,4-dihydro-2H-1,4-benzoxazin-2-yl)benzenecarboximidamnide;

3-(6-Anilino-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(6-(Benzylamino)-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)acetamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)cyclohexanecarboxamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)-2-cyclohexylacetamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)benzenecarboxamide;

N-(2-3-[Amino(imino)methyl]phenyl-4-5-[(2R,6S)-2,6-dimethyltetrahydro-1(2H)-pyridinyl]pentyl-3-oxo-3,4-dihydro-2H-1,4-benzoxazin-6-yl)-2-phenylacetamide;

3-4-5-[(2R,6S)-2,6-Dimethyltetrahydro-1(2H)-pyridinyl]pentyl-6-[(methylsulfonyl)amino]-3-oxo-3,4-dihydro-2H-1,4-benzoxazin-2-ylbenzenecarboximidamide;

3-(6-[(Cyclohexylsulfonyl)amino]-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-(6-[((Cyclohexylmethyl)sulfonyl]amino-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide;

3-4-5-[(2R,6S)-2,6-Dimethyltetrahydro-1(2H)-pyridinyl]pentyl-3-oxo-6-[(phenylsulfonyl)amino]-3,4-dihydro-2H-1,4-benzoxazin-2-ylbenzenecarboximidamide; or 3-(6-[(Benzylsulfonyl)amino]-4-5-[(2R,6S)-2,6-dimethyltetrahydro-1(2H)-pyridinyl]pentyl-3-oxo-3,4-dihydro-2H-1,4-benzoxazin-2-yl)benzenecarboximidamide.

9. A compound which is:

3-((2R)-4-5-[(2R,6S)-2,6-Dimethyltetrahydro-1(2H)-pyridinyl]pentyl-3-oxo-3,4-dihydro-2H-1,4-benzoxazin-2-yl)-4-methoxybenzenecarboximidamide;

3-((2S)-4-5-[(2R,6S)-2,6-Dimethyltetrahydro-1(2H)-pyridinyl]pentyl-3-oxo-3,4-dihydro-2H-1,4-benzoxazin-2-yl)-4-methoxybenzenecarboximidamide;

3-((2R)-4-5-[(2R,6S)-2,6-Dimethyltetrahydro-1(2H)-pyridinyl]pentyl-3-oxo-3,4-dihydro-2H-1,4-benzoxazin-2-yl)-4-hydroxybenzenecarboximidamide;

3-((2S)-4-5-[(2R,6S)-2,6-Dimethyltetrahydro-1(2H)-pyridinyl]pentyl-3-oxo-3,4-dihydro-2H-1,4-benzoxazin-2-yl)-4-hydroxybenzenecarboximidamide;

3-((2R)-4-5-[(2R,6S)-2,6-Dimethyltetrahydro-1(2H)-pyridinyl]pentyl-3-oxo-3,4-dihydro-2H-1,4-benzoxazin-2-yl)benzenecarboximidamide; or 3-((2S)-4-5-[(2R,6S)-2,6-Dimethyltetrahydro-1(2H)-pyridinyl]pentyl-3-oxo-3,4-dihydro-2H-1,4-benzoxazin-2-yl)benzenecarboximidamide.

10. A compound which is:

3-((2S)-4-5-[(2R,6S)-2,6-Dimethyltetrahydro-1(2H)-pyridinyl]pentyl-3-oxo-3,4-dihydro-2H-1,4-benzoxazin-2-yl)-4-hydroxybenzenecarboximidamide.

11. A compound of which is:

2H-1,4-Benzoxazin-3(4H)-one, 4-[3-(2,6-dimethyl-1-piperidinyl)propyl]-2-phenyl-;

4-[5-(2,5-Dimethyl-pyrrolidin-1-yl)-pentyl]-2-phenyl-4H-benzo[1,4]oxazin-3-one;

2H-1,4-Benzoxazin-3(4H)-one, 4-[5-[bis(1-methylethyl)amino]pentyl]-2-phenyl-;

2H-1,4-Benzoxazin-3(4H)-one, 4-[3-(2,5-dimethyl-1-pyrrolidinyl)propyl]-2-phenyl-;

2H-1,4-Benzoxazin-3(4H)-one, 4-[3-[bis(1-methylethyl)amino]propyl]-2-phenyl-;

4-[5-(2,6-Dimethyl-piperidin-1-yl)-pentyl]-2-phenyl-4H-benzo[1,4]oxazin-3-one;

4-(5-Diethylamino-pentyl)-2-phenyl-4H-benzo[1,4]oxazin-3-one;

2-Phenyl-4-(5-pyrrolidin-1-yl-pentyl)-4H-benzo[1,4]oxazin-3-one;

2-[5-(3-Oxo-2-phenyl-2,3-dihydro-benzo[1,4]oxazin-4-yl)-pentyl]-isoindole-1,3-dione;

4-(5-Imidazol-1-yl-pentyl)-2-phenyl-4H-benzo[1,4]oxazin-3-one;

2-(4-Chloro-phenyl)-4-[5-(2,6-dimethyl-piperidin-1-yl)-pentyl]-4H-benzo[1,4]oxazin-3-one;

2-(2-Chloro-phenyl)-4-[5-(2,5-dimethyl-pyrrolidin-1-yl)-pentyl]-4H-benzo[1,4]oxazin-3-one;

2-(2-Chloro-phenyl)-4-[5-(2,6-dimethyl-piperidin-1-yl)-pentyl]-4H-benzo[1,4]oxazin-3-one;

5-(3-Oxo-2-phenyl-2,3-dihydro-benzo[1,4]oxazin-4-yl)-pentanamidine;

2-Phenyl-4-(5-piperidin-1-yl-pentyl)-4H-benzo[1,4]oxazin-3-one;

2-(4-Chloro-phenyl)-4-[5-(2,5-dimethyl-pyrrolidin-1-yl)-pentyl]-4H-benzo[1,4]oxazin-3-one;

2-Phenyl-4-(5-pyrrolidin-1-yl-pentyl)-4H-benzo[1,4]oxazin-3-one; compound with trifluoro-acetic acid;

3-(3-Oxo-2-phenyl-2,3-dihydro-benzo[1,4]oxazin-4-ylmethyl)-benzonitrile;

4-[6-(2,5-Dimethyl-pyrrolidin-1-yl)-hexyl]-2-phenyl-4H-benzo[1,4]oxazin-3-one;

3-(3-Oxo-2-phenyl-2,3-dihydro-benzo[1,4]oxazin-4-ylmethyl)-benzamidine;

2-Naphthalen-2-yl-4-(5-piperidin-1-yl-pentyl)-4H-benzo[1,4]oxazin-3-one;

4-(5-Amino-pentyl)-2-phenyl-4H-benzo[1,4]oxazin-3-one;

4-[5-(2,6-Dimethyl-piperidin-1-yl)-pentyl]-2-phenyl-4H-benzo[1,4]oxazin-3-one;

6-Methyl-2-phenyl-4-(5-piperidin-1-yl-pentyl)-4H-benzo[1,4]oxazin-3-one;

7-Methoxy-2-phenyl-4-(5-piperidin-1-yl-pentyl)-4H-benzo[1,4]oxazin-3-one;

8-Chloro-2-phenyl-4-(5-piperidin-1-yl-pentyl)-4H-benzo[1,4]oxazin-3-one;

3-Oxo-2-phenyl-4-(5-piperidin-1-yl-pentyl)-3,4-dihydro-2H-benzo[1,4]oxazine-6-carbonitrile;

4-(3-Oxo-2-phenyl-2,3-dihydro-benzo[1,4]oxazin-4-ylmethyl)-benzamidine;

1-[5-(3-Oxo-2-phenyl-2,3-dihydro-benzo[1,4]oxazin-4-yl)-pentyl]-piperidine-2,6-dione;

3-(3-Oxo-2-phenyl-2,3-dihydro-benzo[1,4]oxazin-4-yl)-propionitrile;

4-(3-Oxo-2-phenyl-2,3-dihydro-benzo[1,4]oxazin-4-yl)-butyronitrile;

5-(3-Oxo-2-phenyl-2,3-dihydro-benzo[1,4]oxazin-4-yl)-pentanenitrile;

N-[3-(3-Oxo-2-phenyl-2,3-dihydro-benzo[1,4]oxazin-4-yl)-propyl]-guanidine;

N-[5-(3-Oxo-2-phenyl-2,3-dihydro-benzo[1,4]oxazin-4-yl)-pentyl]-guanidine;

4-(3-Oxo-2-phenyl-2,3-dihydro-benzo[1,4]oxazin-4-ylmethyl)-benzamidine;

2-(4-Methoxy-phenyl)-4-(5-piperidin-1-yl-pentyl)-4H-benzo[1,4]oxazin-3-one;

7-Methyl-2-phenyl-4-(5-piperidin-1-yl-pentyl)-4H-benzo[1,4]oxazin-3-one;

5-Methyl-2-phenyl-4-(5-piperidin-1-yl-pentyl)-4H-benzo[1,4]oxazin-3-one;

6-Methoxy-2-phenyl-4-(5-piperidin-1-yl-pentyl)-4H-benzo[1,4]oxazin-3-one;

N-Hydroxy-4-(3-oxo-2-phenyl-2,3-dihydro-benzo[1,4]oxazin-4-ylmethyl)-benzamidine;

6-Chloro-2-phenyl-4-(5-piperidin-1-yl-pentyl)-4H-benzo[1,4]oxazin-3-one;

2-(4-Methoxy-phenyl)-4-(5-piperazin-1-yl-pentyl)-4H-benzo[1,4]oxazin-3-one;

2-(4-Hydroxy-phenyl)-4-(5-piperidin-1-yl-pentyl)-4H-benzo[1,4]oxazin-3-one;

4-[5-(2,6-Dimethyl-piperidin-1-yl)-pentyl]-2-(4-hydroxy-phenyl)-4H-benzo[1,4]oxazin-3-one;

2-(4-Methoxy-phenyl)-4-[5-(4-methyl-piperazin-1-yl)-pentyl]-4H-benzo[1,4]oxazin-3-one;

4-{4-[5-(2,6-Dimethyl-piperidin-1-yl)-pentyl]-3-oxo-3,4-dihydro-2H-benzo[1,4]oxazin-2-yl}-benzonitrile;

4-{(4-[5-(2,6-Dimethyl-piperidin-1-yl)-pentyl]-3-oxo-3,4-dihydro-2H-benzo[1,4]oxazin-2-yl}-benzamidine;

4-{4-[5-(2,6-Dimethyl-piperidin-1-yl)-pentyl]-3-oxo-3,4-dihydro-2H-benzo[1,4]oxazin-2-yl}-thiobenzamide;

[2-(4-Methoxy-phenyl)-3-oxo-2,3-dihydro-benzo[1,4]oxazin-4-yl]-acetic acid;

4-{4-[5-(2,6-Dimethyl-piperidin-1-yl)-pentyl]-3-oxo-3,4-dihydro-2H-benzo[1,4]oxazin-2-yl}-N-hydroxy-benzamidine;

Benzenecarboximidic acid, 4-[3,4-dihydro-4-[5-(2,6-dimethyl-1-piperidinyl)pentyl]-3-oxo-2H-1,4-benzoxazin-2-yl]-, hydrazide;

6-Amino-2-phenyl-4-(5-piperidin-1-yl-pentyl)-4H-benzo[1,4]oxazin-3-one;

4-(5-Bromo-pentyl)-2-(3,4-dimethoxy-phenyl)-4H-benzo[1,4]oxazin-3-one;

4-(5-Bromo-pentyl)-2-(3,4,5-trimethoxy-phenyl)-4H-benzo[1,4]oxazin-3-one;

4-(5-Bromo-pentyl)-2-(4-methoxy-phenyl)-4H-benzo[1,4]oxazin-3-one;

N-[2-(2,6-Dimethyl-piperidin-1-yl)-ethyl]-2-[2-(4-methoxy-phenyl)-3-oxo-2,3-dihydro-benzo[1,4]oxazin-4-yl]-acetamide;

4-[5-(2,6-Dimethyl-piperidin-1-yl)-pentyl]-2-(3,4,5-trimethoxy-phenyl)-4H-benzo[1,4]oxazin-3-one;

2-(3,4-Dimethoxy-phenyl)-4-[5-(2,6-dimethyl-piperidin-1-yl)-pentyl]-4H-benzo[1,4]oxazin-3-one;

2-(4-Bromo-phenyl)-4-[5-(2,6-dimethyl-piperidin-1-yl)-pentyl]-4H-benzo[1,4]oxazin-3-one;

8-Methyl-2-phenyl-4-(5-piperidin-1-yl-pentyl)-4H-benzo[1,4]oxazin-3-one;

2-(4-Benzylamino-phenyl)-4-[5-(2,6-dimethyl-piperidin-1-yl)-pentyl]-4H-benzo[1,4]oxazin-3-one;

2-(4-Methoxy-phenyl)-4-[5-(2,2,6,6-tetramethyl-piperidin-1-yl)-pentyl]-4H-benzo[1,4]oxazin-3-one;

4-(2-Bromo-ethyl)-2-(4-methoxy-phenyl)-4H-benzo[1,4]oxazin-3-one;

4-(5-Bromo-pentyl)-2-(3,4-dichloro-phenyl)-4H-benzo[1,4]oxazin-3-one;

4-(2-Hydroxy-ethyl)-2-(4-methoxy-phenyl)-4H-benzo[1,4]oxazin-3-one;

2-(3,4-Dichloro-phenyl)-4-[5-(2,6-dimethyl-piperidin-1-yl)-pentyl]-4H-benzo[1,4]oxazin-3-one;

4-[3-(2,6-Dimethyl-piperidin-1-ylmethyl)-benzyl]-2-(4-methoxy-phenyl)-4H-benzo[1,4]oxazin-3-one;

4-(2-Amino-ethyl)-2-(4-methoxy-phenyl)-4H-benzo[1,4]oxazin-3-one;

2-(2,6-Dimethyl-piperidin-1-yl)-N-{2-[2-(4-methoxy-phenyl)-3-oxo-2,3-dihydro-benzo[1,4]oxazin-4-yl]-ethyl}-acetamide;

4-[5-(2,6-Dimethyl-piperidin-1-yl)-5-oxo-pentyl]-2-(4-methoxy-phenyl)-4H-benzo[1,4]oxazin-3-one;

3-{4-[4-(2,6-Dimethyl-piperidin-1-yl)-butyl]-3-oxo-3,4-dihydro-2H-benzo[1,4]oxazin-2-yl}-benzamidine;

3-{4-[6-(2,6-Dimethyl-piperidin-1-yl)-hexyl]-3-oxo-3,4-dihydro-2H-benzo[1,4]oxazin-2-yl}-benzamidine;

2-(5-Aminomethyl-2-hydroxy-phenyl)-4-[5-(2,6-dimethyl-piperidin-1-yl)-pentyl]-4H-benzo[1,4]oxazin-3-one;

2-(3-Aminomethyl-phenyl)-4-[5-(2,6-dimethyl-piperidin-1-yl)-pentyl]-4H-benzo[1,4]oxazin-3-one;

3-{4-[5-(2,6-Dimethyl-piperidin-1-yl)-pentyl]-7-methyl-3-oxo-3,4-dihydro-2H-benzo[1,4]oxazin-2-yl}-benzamidine;

3-{4-[5-(2,6-Dimethyl-piperidin-1-yl)-pentyl]-3-oxo-3,4-dihydro-2H-benzo[1,4]oxazin-2-yl}-4-methoxy-benzamidine;

2-(5-Aminomethyl-2-methoxy-phenyl)-4-[5-(2,6-dimethyl-piperidin-1-yl)-pentyl]-4H-benzo[1,4]oxazin-3-one;

3-{4-[5-(2,6-Dimethyl-piperidin-1-yl)-pentyl]-3-oxo-3,4-dihydro-2H-benzo[1,4]oxazin-2-yl}-N-hydroxy-4-methoxy-benzamidine;

3-{4-[5-(2,6-Dimethyl-piperidin-1-yl)-pentyl]-3-oxo-3,4-dihydro-2H-benzo[1,4]oxazin-2-yl}-N-hydroxy-benzamidine;

3-{7-Chloro-4-[5-(2,6-dimethyl-piperidin-1-yl)-pentyl]-3-oxo-3,4-dihydro-2H-benzo[1,4]oxazin-2-yl}-benzamidine;

4-(5-Bromo-pentyl)-2-phenyl-4H-benzo[1,4]oxazin-3-one;

3-[3-Oxo-4-(5-piperidin-1-yl-pentyl)-3,4-dihydro-2H-benzo[1,4]oxazin-2-yl]-benzamidine;

N-{2-(3-Carbamimidoyl-phenyl)-4-[5-(2,6-dimethyl-piperidin-1-yl)-pentyl]-3-oxo-3,4-dihydro-2H-benzo[1,4]oxazin-6-yl}-acetamide;

3-{4-[5-(2,6-Dimethyl-piperidin-1-yl)-pentyl]-2-methyl-3-oxo-3,4-dihydro-2H-benzo[1,4]oxazin-2-yl}-4-hydroxy-benzamidine;

3-[4-(5-Diisopropylamino-pentyl)-3-oxo-3,4-dihydro-2H-benzo[1,4]oxazin-2-yl]-benzamidine;

3-(4-{4-[(Diisopropylamino)-methyl]-benzyl}-3-oxo-3,4-dihydro-2H-benzo[1,4]oxazin-2-yl)-benzamidine;

3-{4-[4-(2,6-Dimethyl-piperidin-1-ylmethyl)-benzyl]-3-oxo-3,4-dihydro-2H-benzo[1,4]oxazin-2-yl}-benzamidine;

3-{4-[5-(2,6-Dimethyl-piperidin-1-yl)-pentyl]-3-oxo-3,4-dihydro-2H-benzo[1,4]oxazin-2-yl}-4-hydroxy-benzamidine;

3-{4-[5-(2,6-Dimethyl-piperidin-1-yl)-pentyl]-3-oxo-3,4-dihydro-2H-benzo[1,4]oxazin-2-yl}-N-methyl-benzamidine;

{2-(3-Carbamimidoyl-phenyl)-4-[5-(2,6-dimethyl-piperidin-1-yl)-pentyl]-3-oxo-3,4-dihydro-2H-benzo[1,4]oxazin-6-yl}-acetic acid;

3-(4-{3-[(Diisopropylamino)-methyl]-benzyl}-3-oxo-3,4-dihydro-2H-benzo[1,4]oxazin-2-yl)-benzamidine;

3-{4-[3-(2,6-Dimethyl-piperidin-1-ylmethyl)-benzyl]-3-oxo-3,4-dihydro-2H-benzo[1,4]oxazin-2-yl}-benzamidine;

2-(3-Carbamimidoyl-phenyl)-4-[5-(2,6-dimethyl-piperidin-1-yl)-pentyl]-3-oxo-3,4-dihydro-2H-benzo[1,4]oxazine-7-carboxylic acid;

3-{3-Oxo-4-[4-(pyridin-2-ylamino)-butyl]-3,4-dihydro-2H-benzo[1,4]oxoazin-2-yl}-benzamidine;

2-(3-Carbamimidoyl-phenyl)-4-[5-(2,6-dimethyl-piperidin-1-yl)-pentyl]-3-oxo-3,4-dihydro-2H-benzo[1,4]oxazine-7-carboxylic acid methyl ester;

3-[4-(5-Dihexylamino-pentyl)-3-oxo-3,4-dihydro-2H-benzo[1,4]oxazin-2-yl]-benzamidine;

3-{4-[4-(Methyl-pyridin-2-yl-amino)-butyl]-3-oxo-3,4-dihydro-2H-benzo[1,4]oxazin-2-yl}-benzamidine;

4-[5-(2,6-Dimethyl-piperidin-1-yl)-pentyl]-2-[3-(imino-morpholin-4-yl-methyl)-phenyl]-4H-benzo[1,4]oxazin-3-one;

3-{3-Oxo-4-[4-(pyrimidin-2-ylamino)-butyl]-3,4-dihydro-2H-benzo[1,4]oxazin-2-yl}-benzamidine;

3-[4-(4-Cyclohexylamino-butyl)-3-oxo-3,4-dihydro-2H-benzo[1,4]oxazin-2-yl]-benzamidine;

3-{4-[5-(2,5-Dimethyl-pyrrolidin-1-yl)-pentyl]-3-oxo-3,4-dihydro-2H-benzo[1,4]oxazin-2-yl}-benzamidine;

3-[4-(5-Morpholin-4-yl-pentyl)-3-oxo-3,4-dihydro-2H-benzo[1,4]oxazin-2-yl]-benzamidine;

3-{4-[5-(2,6-Dimethyl-piperidin-1-yl)-2,3-dihydroxy-pentyl]-3-oxo-3,4-dihydro-2H-benzo[1,4]oxazin-2-yl}-benzamidine;

4-[2-(3-Carbamimidoyl-phenyl)-3-oxo-2,3-dihydro-benzo[1,4]oxazin-4-ylmethyl]-N,N-dimethyl-benzamide;

2-(3-Carbamimidoyl-phenyl)-4-[5-(2,6-dimethyl-piperidin-1-yl)-pentyl]-3-oxo-3,4-dihydro-2H-benzo[1,4]oxazine-6-carboxylic acid;

3-[2-(3-Carbamimidoyl-phenyl)-3-oxo-2,3-dihydro-benzo[1,4]oxazin-4-ylmethyl]-N,N-dimethyl-benzamide;

3-{4-[5-(2,6-Dimethyl-piperidin-1-yl)-pent-2-enyl]-3-oxo-3,4-dihydro-2H-benzo[1,4]oxazin-2-yl}-benzamidine;

3-[4-(5-Amino-pentyl)-3-oxo-3,4-dihydro-2H-benzo[1,4]oxazin-2-yl]-benzamidine;

2-(3-Carbamimidoyl-phenyl)-4-[5-(2,6-dimethyl-piperidin-1-yl)-pentyl]-3-oxo-3,4-dihydro-2H-benzo[1,4]oxazine-6-carboxylic acid methyl ester;

4-Methoxy-3-[4-(4-methoxy-benzyl)-3-oxo-3,4-dihydro-2H-benzo[1,4]oxazin-2-yl]-benzonitrile;

3-{4-[5-(2,6-Dimethyl-piperidin-1-yl)-pent-3-enyl]-3-oxo-3,4-dihydro-2H-benzo[1,4]oxazin-2-yl}-benzamidine;

4-[2-(3-Cyano-phenyl)-3-oxo-2,3-dihydro-benzo[1,4]oxazin-4-ylmethyl]-N,N-dimethyl-benzamide;

3-[2-(3-Carbamimidoyl-phenyl)-3-oxo-2,3-dihydro-benzo[1,4]oxazin-4-ylmethyl]-5-(2,6-dimethyl-piperidin-1-ylmethyl)-benzoic acid;

3-{4-[5-(2,6-Dimethyl-piperidin-1-yl)-pentyl]-3-oxo-3,4-dihydro-2H-benzo[1,4]oxazin-2-yl}-4-hydroxy-benzamidine;

3-Acetyl-2-(2-methoxy-phenyl)-thiazolidine-4-carboxylic acid 4-cyano-2-{4-[5-(2,6-dimethyl-piperidin-1-yl)-pentyl]-3-oxo-3,4-dihydro-2H-benzo[1,4]oxazin-2-yl}-phenyl ester;

3-[2-(3-Carbamimidoyl-phenyl)-3-oxo-2,3-dihydro-benzo[1,4]oxazin-4-ylmethyl]-5-(2,6-dimethyl-piperidin-1-ylmethyl)-N-hydroxy-benzamide;

3-{4-[5-(2,6-dimethyl-piperidin-1-yl)-pentyl]-3-oxo-3,4-dihydro-2H-benzo[1,4]oxazin-2-yl}-piperidine-1-carboxamidine;

4-[5-(2,6-Dimethyl-piperidin-1-yl)-pentyl]-2-piperidin-3-yl-4H-benzo[1,4]oxazin-3-one;

3-Oxo-2-phenyl-2,4-bis-(5-piperidin-1-yl-pentyl)-3,4-dihydro-2H-benzo[1,4]oxazine-6-carbonitrile;

4-[5-(2,6-Dimethyl-piperidin-1-yl)-pentyl]-2-pyridin-2-yl-4H-benzo[1,4]oxazin-3-one;

N-Hydroxy-3-oxo-2-phenyl-4-(5-piperidin-1-yl-pentyl)-3,4-dihydro-2H-benzo[1,4]oxazine-6-carboxamidine;

3-Oxo-2-phenyl-4-(5-piperidin-1-yl-pentyl)-3,4-dihydro-2H-benzo[1,4]oxazine-6-carboxamidine;

3-{4-[5-(2,6-Dimethyl-piperidin-1-yl)-pentyl]-3-oxo-3,4-dihydro-2H-benzo[1,4]oxazin-2-yl}-thiobenzamide;

3-{4-[5-(Adamantan-1-ylamino)-pentyl]-3-oxo-3,4-dihydro-2H-benzo[1,4]oxazin-2-yl}-benzamidine;

2-(3-Diethylamino-propylamino)-4-methyl-2-phenyl-4H-benzo[1,4]oxazin-3-one;

4-[3-(2,6-Dimethyl-1-piperidinyl)propyl]-2-phenyl-2H/-1,4-benzoxazin-3(4H/)-one; or 4-Methyl-2-phenyl-2H/-1,4-benzoxazin-3(4H/)-one.

12. A pharmaceutical formulation comprising a compound of claim 1 admixed with a carrier, diluent or excipient.

13. A pharmaceutical formulation comprising a compound of claim 8 together with a carrier, diluent or excipient.

14. A pharmaceutical formulation comprising a compound of claim 9 together with a carrier, diluent or excipient.

15. A method for the treatment or prophylaxis of thrombotic disorders in a mammal comprising administering to said mammal an effective amount of a compound according to claim 7.

16. A method according to claim 15, wherein said disorder is venous thrombosis.

17. A method according to claim 15, wherein said disorder is arterial thrombosis.

18. A method according to claim 15, wherein said disorder is pulmonary embolism.

19. A method according to claim 15, wherein said disorder is myocardial infarction.

20. A method according to claim 15, wherein said disorder is cerebral infarction.

21. A method according to claim 15, wherein said disorder is restenosis.

22. A method according to claim 15, wherein said disorder is cancer.

23. A method according to claim 15, wherein said disorder is angina.

24. A method according to claim 15, wherein said disorder is diabetes.

25. A method according to claim 15, wherein said disorder is atrial fibrillation.

26. A method according to claim 15, wherein said disorder is heart failure.

27. A method for inhibiting serine proteases comprising administering to a mammal an effective amount of serine protease inhibitor of claim 1.

28. A method according to claim 27, wherein said serine protease is factor Xa.

* * * * *

UNITED STATES PATENT AND TRADEMARK OFFICE
CERTIFICATE OF CORRECTION

PATENT NO.    : 6,509,335 B1
DATED         : January 21, 2003
INVENTOR(S)   : Kent Alan Berryman et al.

It is certified that error appears in the above-identified patent and that said Letters Patent is hereby corrected as shown below:

<u>Column 94,</u>
Line 40, "A compound according to claim 1 wherei n $R_8$ is H, $R_9$" should read
-- A compound according to claim 1 wherein $R_8$ is H, $R_9$ --

<u>Column 97,</u>
Line 53, "3-[(4-5[(2R,6S)-2,6-Dimethyltetrahydro-1(214)-" should read
-- 3-[(4-5[(2R,6S)-2,6-Dimethyltetrahydro-1(2H)- --

<u>Column 99,</u>
Line 32, "3-(4-5-12-(Hydroxymethyl)-5-methyl-1-pyrrolidinyl]" should read
-- 3-(4-5-[2-(Hydroxymethyl)-5-methyl-1-pyrrolidinyl] --

<u>Column 107,</u>
Line 22, "to claim 7." should read -- to claim 1. --

Signed and Sealed this

Nineteenth Day of August, 2003

JAMES E. ROGAN
*Director of the United States Patent and Trademark Office*